(12) United States Patent
Konofagou et al.

(10) Patent No.: US 10,687,785 B2
(45) Date of Patent: Jun. 23, 2020

(54) SYSTEM AND METHOD FOR ELECTROMECHANICAL ACTIVATION OF ARRHYTHMIAS

(71) Applicant: THE TRUSTEES OF COLUMBIA UNIVERSITY IN THE CITY OF NEW YORK, New York, NY (US)

(72) Inventors: Elisa E. Konofagou, New York, NY (US); Jean Provost, Paris (FR)

(73) Assignee: THE TRUSTEES OF COLUMBIA UNIVERISTY IN THE CITY OF NEW YORK, New York, NY (US)

(*) Notice: Subject to any disclaimer, the term of this patent is extended or adjusted under 35 U.S.C. 154(b) by 1161 days.

(21) Appl. No.: 15/048,761

(22) Filed: Feb. 19, 2016

(65) Prior Publication Data

US 2016/0249880 A1 Sep. 1, 2016

Related U.S. Application Data

(63) Continuation-in-part of application No. 14/449,820, filed on Aug. 1, 2014, now abandoned, which is a
(Continued)

(51) Int. Cl.
*A61B 8/08* (2006.01)
*G01S 15/89* (2006.01)
(Continued)

(52) U.S. Cl.
CPC .............. *A61B 8/0883* (2013.01); *A61B 8/08* (2013.01); *A61B 8/485* (2013.01); *A61B 8/5223* (2013.01);
(Continued)

(58) Field of Classification Search
CPC .............................. A61B 8/0883; A61B 8/485
See application file for complete search history.

(56) References Cited

U.S. PATENT DOCUMENTS 3,598,111 A 8/1971 Kahn
4,463,608 A 8/1984 Takeuchi et al.
(Continued)

FOREIGN PATENT DOCUMENTS

CN 102608212 7/2012
EP 0 221 409 A2 5/1987
(Continued)

OTHER PUBLICATIONS

U.S. Appl. No. 14/449,820, Mar. 2, 2017, Non-Final Office Action.
(Continued)

*Primary Examiner* — Rochelle D Turchen
(74) *Attorney, Agent, or Firm* — Baker Botts L.L.P.

(57) ABSTRACT

Systems and methods for detecting electromechanical wave propagation within a body structure of a patient in a series of image frames representing movement the body structure are provided. Image data is acquired comprising a series of image frames corresponding to the movement of a body structure. A correlation calculation is performed on the image frames to generate a displacement map representing the relative displacement between the first and second image frames. A video is generated comprising a series of displacement maps. The parameters of movement of the body structure are detected by analysis of the displacement maps. The image acquisition can detect the movement of the body structure without inducing such movement.

16 Claims, 29 Drawing Sheets

Related U.S. Application Data continuation of application No. 11/433,510, filed on May 12, 2006, now Pat. No. 8,858,441.

(60) Provisional application No. 60/680,081, filed on May 12, 2005, provisional application No. 62/118,402, filed on Feb. 19, 2015.

(51) Int. Cl.
  *G01S 7/52* (2006.01)
  *A61B 8/00* (2006.01)

(52) U.S. Cl.
  CPC ...... *G01S 7/52042* (2013.01); *G01S 7/52087* (2013.01); *G01S 15/8956* (2013.01); *G01S 15/8977* (2013.01); *A61B 8/463* (2013.01); *G01S 15/8925* (2013.01)

(56) References Cited

U.S. PATENT DOCUMENTS

| | | |
|---|---|---|
| 4,777,599 A | 10/1988 | Dorogi et al. |
| 4,832,941 A | 5/1989 | Berwing et al. |
| 4,858,613 A | 8/1989 | Fry et al. |
| 4,822,679 A | 11/1989 | Tuy et al. |
| 4,926,675 A | 5/1990 | Schohl et al. |
| 5,038,787 A | 8/1991 | Antich et al. |
| 5,107,837 A | 4/1992 | Ophir et al. |
| 5,178,147 A | 1/1993 | Ophir et al. |
| 5,309,914 A | 5/1994 | Ilnuma |
| 5,433,708 A | 7/1995 | Nichols et al. |
| 5,435,310 A | 7/1995 | Sheehan et al. |
| 5,457,754 A | 10/1995 | Han et al. |
| 5,601,084 A | 2/1997 | Sheehan et al. |
| 5,606,971 A | 3/1997 | Sarvazyan |
| 5,662,113 A | 9/1997 | Liu |
| 5,718,241 A | 2/1998 | Ben-Haim et al. |
| 5,722,411 A | 3/1998 | Suzuki et al. |
| 5,741,522 A | 4/1998 | Violante et al. |
| 5,752,515 A | 5/1998 | Jolesz et al. |
| 5,769,790 A | 6/1998 | Watkins et al. |
| 5,810,731 A | 9/1998 | Sarvazyan et al. |
| 5,840,028 A | 11/1998 | Chubachi et al. |
| 5,928,151 A | 7/1999 | Hossack et al. |
| 6,026,173 A | 2/2000 | Svenson et al. |
| 6,028,066 A | 2/2000 | Unger |
| 6,102,864 A | 8/2000 | Hatfield et al. |
| 6,102,865 A | 8/2000 | Hossack et al. |
| 6,106,465 A | 8/2000 | Napolitano et al. |
| 6,123,669 A | 9/2000 | Kanda et al. |
| 6,152,878 A | 11/2000 | Nachtomy et al. |
| 6,193,951 B1 | 2/2001 | Ottoboni et al. |
| 6,200,266 B1 | 3/2001 | Shokrollahi et al. |
| 6,241,675 B1 | 6/2001 | Smith et al. |
| 6,246,895 B1 | 6/2001 | Plews |
| 6,259,943 B1 | 7/2001 | Cosman et al. |
| 6,270,459 B1 | 8/2001 | Konofagou et al. |
| 6,309,355 B1 | 10/2001 | Cain et al. |
| 6,312,382 B1 | 11/2001 | Mucci et al. |
| 6,352,507 B1 | 3/2002 | Torp et al. |
| 6,413,216 B1 | 7/2002 | Cain et al. |
| 6,425,865 B1 | 7/2002 | Salcudean et al. |
| 6,425,867 B1 | 7/2002 | Vaezy et al. |
| 6,447,450 B1 | 9/2002 | Oldstad |
| 6,488,629 B1 | 12/2002 | Saetre et al. |
| 6,491,636 B2 | 12/2002 | Chenal et al. |
| 6,508,768 B1 | 1/2003 | Hall et al. |
| 6,514,221 B2 | 2/2003 | Hynynen et al. |
| 6,529,770 B1 | 3/2003 | Grimblatov |
| 6,537,217 B1 | 3/2003 | Bjærum et al. |
| 6,537,221 B2 | 3/2003 | Criton et al. |
| 6,671,541 B2 | 12/2003 | Bishop et al. |
| 6,683,454 B2 | 1/2004 | Rehwald et al. |
| 6,685,641 B2 | 2/2004 | Liu et al. |
| 6,689,060 B2 | 2/2004 | Phelps et al. |
| 6,701,341 B1 | 3/2004 | Wu et al. |
| 6,770,033 B1 | 8/2004 | Fink et al. |
| 6,775,400 B1 | 8/2004 | Zhao et al. |
| 6,875,176 B2 | 4/2005 | Mourad et al. |
| 6,936,151 B1 | 8/2005 | Lock et al. |
| 6,984,209 B2 | 1/2006 | Hynynen et al. |
| 6,994,673 B2 | 2/2006 | Lysyansky et al. |
| 7,016,719 B2 | 3/2006 | Rudy et al. |
| 7,055,378 B2 | 6/2006 | Su et al. |
| 7,136,518 B2 | 11/2006 | Griffin et al. |
| 7,257,244 B2 | 8/2007 | Miga |
| 7,331,926 B2 | 2/2008 | Varghese et al. |
| 7,344,509 B2 | 3/2008 | Hynynen et al. |
| 7,421,101 B2 | 9/2008 | Georgescu et al. |
| 7,429,249 B1 | 9/2008 | Winder et al. |
| 7,449,306 B2 | 11/2008 | Elson |
| 7,601,122 B2 | 10/2009 | Zagzebski et al. |
| 7,753,847 B2 | 7/2010 | Greenleaf et al. |
| 7,809,426 B2 | 10/2010 | Kim et al. |
| 7,896,821 B1 | 3/2011 | Magnin et al. |
| 8,029,444 B2 | 10/2011 | Pedrizzetti et al. |
| 8,150,128 B2 | 4/2012 | Konofagou et al. |
| 8,208,709 B2 | 6/2012 | Ding et al. |
| 8,257,338 B2 | 9/2012 | Keenan et al. |
| 9,063,220 B2 | 6/2015 | Yoda et al. |
| 9,358,023 B2 | 6/2016 | Konofagou et al. |
| 2002/0034757 A1 | 3/2002 | Cubicciotti |
| 2002/0038086 A1 | 3/2002 | Hynynen et al. |
| 2002/0039594 A1 | 4/2002 | Unger |
| 2002/0065461 A1 | 5/2002 | Cosman |
| 2002/0095081 A1 | 7/2002 | Vilsmeier |
| 2002/0151792 A1 | 10/2002 | Conston et al. |
| 2002/0169394 A1 | 11/2002 | Eppstein et al. |
| 2002/0169484 A1 | 11/2002 | Mathis et al. |
| 2002/0193784 A1 | 12/2002 | Mchale et al. |
| 2003/0040675 A1 | 2/2003 | Sharrock |
| 2003/0097068 A1 | 5/2003 | Hossack et al. |
| 2003/0125621 A1 | 7/2003 | Drukker et al. |
| 2003/0135124 A1 | 7/2003 | Russell |
| 2003/0171672 A1 | 9/2003 | Varghese et al. |
| 2003/0174890 A1 | 9/2003 | Yamauchi |
| 2003/0220556 A1 | 11/2003 | Porat et al. |
| 2003/0236466 A1 | 12/2003 | Tarjan et al. |
| 2004/0006266 A1 | 1/2004 | Ustuner et al. |
| 2004/0049134 A1 | 3/2004 | Tosaya |
| 2004/0049232 A1 | 3/2004 | Ideker et al. |
| 2004/0054357 A1 | 3/2004 | O'Donnell |
| 2004/0059220 A1 | 3/2004 | Mourad et al. |
| 2004/0059224 A1 | 3/2004 | Varghese et al. |
| 2004/0092816 A1 | 5/2004 | Ossmann et al. |
| 2004/0097805 A1 | 5/2004 | Verard et al. |
| 2004/0116812 A1 | 6/2004 | Selzer et al. |
| 2004/0122320 A1 | 6/2004 | Murashita |
| 2004/0143189 A1 | 7/2004 | Lysyansky et al. |
| 2004/0167403 A1 | 8/2004 | Nightingale et al. |
| 2004/0172081 A1 | 9/2004 | Wang |
| 2004/0249580 A1 | 9/2004 | Pourcelot et al. |
| 2004/0210134 A1 | 10/2004 | Hynynen et al. |
| 2004/0210135 A1 | 10/2004 | Hynynen |
| 2004/0234113 A1 | 11/2004 | Miga |
| 2004/0236219 A1 | 11/2004 | Liu et al. |
| 2004/0258760 A1 | 12/2004 | Wheatley et al. |
| 2005/0004466 A1 | 1/2005 | Hynynen et al. |
| 2005/0267695 A1 | 1/2005 | German |
| 2005/0026262 A1 | 2/2005 | Yoshitani et al. |
| 2005/0054930 A1 | 3/2005 | Rickets et al. |
| 2005/0059876 A1 | 3/2005 | Krishnan et al. |
| 2005/0080336 A1 | 4/2005 | Byrd et al. |
| 2005/0080469 A1 | 4/2005 | Larson et al. |
| 2005/0084538 A1 | 4/2005 | Dayton et al. |
| 2005/0124892 A1 | 6/2005 | Weitzel et al. |
| 2005/0175541 A1 | 8/2005 | Lanza et al. |
| 2005/0201942 A1 | 9/2005 | Dugstad et al. |
| 2005/0203395 A1 | 9/2005 | Sui et al. |
| 2005/0233399 A1 | 9/2005 | Vaezy et al. |
| 2005/0259864 A1 | 11/2005 | Dickinson et al. |
| 2005/0277824 A1 | 12/2005 | Aubry et al. |
| 2005/0277835 A1 | 12/2005 | Angelsen et al. |
| 2006/0034904 A1 | 2/2006 | Weimann |

(56) References Cited

U.S. PATENT DOCUMENTS

| | | |
|---|---|---|
| 2006/0058651 A1 | 3/2006 | Chiao et al. |
| 2006/0058671 A1 | 3/2006 | Vitek et al. |
| 2006/0058673 A1 | 3/2006 | Aase et al. |
| 2006/0074315 A1 | 4/2006 | Liang et al. |
| 2006/0078501 A1 | 4/2006 | Goertz et al. |
| 2006/0173320 A1 | 8/2006 | Radulescu |
| 2006/0241462 A1 | 10/2006 | Chou et al. |
| 2006/0241529 A1 | 10/2006 | Hynynen et al. |
| 2007/0049824 A1 | 3/2007 | Konofagou et al. |
| 2007/0055179 A1 | 3/2007 | Deem et al. |
| 2007/0059247 A1 | 3/2007 | Lindner et al. |
| 2007/0071683 A1 | 3/2007 | Dayton et al. |
| 2007/0129652 A1 | 6/2007 | Nita |
| 2007/0207194 A1 | 9/2007 | Grayburn et al. |
| 2007/0219447 A1 | 9/2007 | Kanai et al. |
| 2007/0232962 A1 | 10/2007 | Zumeris et al. |
| 2007/0239001 A1 | 10/2007 | Mehi et al. |
| 2007/0276242 A1 | 11/2007 | Konofagou |
| 2007/0276245 A1 | 11/2007 | Konofagou |
| 2007/0276254 A1 | 11/2007 | Konofagou |
| 2008/0081990 A1* | 4/2008 | Berenfeld ............ A61B 1/042 600/420 |
| 2008/0194957 A1 | 8/2008 | Hoctor et al. |
| 2008/0200417 A1 | 8/2008 | Semple et al. |
| 2008/0243214 A1 | 10/2008 | Koblish |
| 2008/0260802 A1 | 10/2008 | Sawhney et al. |
| 2008/0269606 A1 | 10/2008 | Matsumura |
| 2008/0269668 A1 | 10/2008 | Keenan et al. |
| 2008/0285819 A1 | 11/2008 | Konofagou et al. |
| 2008/0319355 A1 | 12/2008 | Nita |
| 2008/0319375 A1 | 12/2008 | Hardy |
| 2009/0005711 A1 | 1/2009 | Konofagou et al. |
| 2009/0191244 A1 | 7/2009 | Kheir et al. |
| 2009/0221916 A1 | 9/2009 | Konofagou et al. |
| 2009/0247911 A1 | 10/2009 | Novak et al. |
| 2009/0270790 A1 | 10/2009 | Raghavan |
| 2010/0049036 A1 | 2/2010 | Kimh |
| 2010/0056924 A1 | 3/2010 | Powers |
| 2010/0143241 A1 | 6/2010 | Johnson et al. |
| 2010/0286527 A1 | 11/2010 | Cannon et al. |
| 2011/0028854 A1 | 2/2011 | Addison et al. |
| 2011/0098562 A1 | 4/2011 | Salgo et al. |
| 2011/0177005 A1 | 7/2011 | Rapoport et al. |
| 2011/0208038 A1* | 8/2011 | Konofagou ............ A61B 5/055 600/410 |
| 2011/0245701 A1* | 10/2011 | Bjorling ............ A61B 5/0031 600/516 |
| 2011/0295105 A1 | 12/2011 | Konofagou et al. |
| 2011/0313328 A1 | 12/2011 | Nita |
| 2012/0004693 A1 | 1/2012 | Lo et al. |
| 2012/0179073 A1 | 7/2012 | Nita |
| 2013/0038479 A1 | 2/2013 | Eldar et al. |
| 2013/0046229 A1 | 2/2013 | Konofagou et al. |
| 2013/0066211 A1 | 3/2013 | Konofagou et al. |
| 2013/0131495 A1 | 5/2013 | Konofagou et al. |
| 2013/0195313 A1 | 8/2013 | Gauthier et al. |
| 2013/0289398 A1 | 10/2013 | Borden et al. |
| 2013/0304407 A1 | 11/2013 | George et al. |
| 2013/0315491 A1 | 11/2013 | Konofagou et al. |
| 2014/0114216 A1 | 4/2014 | Konofagou et al. |
| 2016/0107002 A1 | 4/2016 | Nita |

FOREIGN PATENT DOCUMENTS

| | | |
|---|---|---|
| EP | 0 627 206 A2 | 12/1994 |
| WO | WO 1999/037938 A1 | 7/1999 |
| WO | WO 2007/148279 A1 | 12/2007 |
| WO | WO 2008/015012 A1 | 2/2008 |
| WO | WO 2008/027520 A2 | 3/2008 |
| WO | WO 2008/062342 A2 | 5/2008 |
| WO | WO 2008/131217 A1 | 10/2008 |
| WO | WO 2008/131302 A2 | 10/2008 |
| WO | WO 2008/157422 A1 | 12/2008 |
| WO | WO 2010/030819 A1 | 3/2010 |
| WO | WO 2010/044385 A1 | 4/2010 |
| WO | WO 2010/063951 A1 | 6/2010 |
| WO | WO 2011/028690 | 3/2011 |
| WO | WO 2011/035312 A1 | 3/2011 |
| WO | WO 2011/153268 A2 | 12/2011 |

OTHER PUBLICATIONS

U.S. Appl. No. 12/077,612 (Abandoned), filed Mar. 19, 2008.
U.S. Appl. No. 13/019,029 (U.S. Pat. No. 8,428,687), filed Feb. 1, 2011 (Apr. 23, 2013).
U.S. Appl. No. 13/045,070 (U.S. Pat. No. 9,302,124), filed Mar. 10, 2011, (Apr. 5, 2016).
U.S. Appl. No. 13/353,148 (Abandoned), filed Jan. 18, 2012.
U.S. Appl. No. 13/426,400 (U.S. Pat. No. 9,358,023), filed Mar. 21, 2012 (Jun. 7, 2016).
U.S. Appl. No. 13/529,239 (Abandoned), filed Jun. 21, 2012.
U.S. Appl. No. 13/848,436 (U.S. Pat. No. 9,514,358), filed Mar. 21, 2013 (Dec. 6, 2016).
U.S. Appl. No. 14/091,010 (US 2014/0114216), filed Nov. 26, 2013 (Apr. 24, 2014).
U.S. Appl. No. 14/300,106 (U.S. Pat. No. 9,247,921), filed Jun. 9, 2014 (Feb. 2, 2016).
U.S. Appl. No. 14/457,023 (US 2015/0045724), filed Aug. 11, 2014 (Feb. 12, 2015).
U.S. Appl. No. 14/476,543 (US 2015/0065871, filed Sep. 3, 2014 (Mar. 5, 2015).
U.S. Appl. No. 14/682,980 (US 2015/0289840), filed Apr. 9, 2015 (Oct. 15, 2015).
U.S. Appl. No. 14/695,674 (US 2015/0297188), filed Apr. 24, 2015 (Oct. 22, 2015).
U.S. Appl. No. 14/949,000 (US 2016/0074678), filed Nov. 23, 2015 (Mar. 17, 2016).
U.S. Appl. No. 15/368,366 (US 2017/0148163), filed Dec. 2, 2016 (May 25, 2017).
U.S. Appl. No. 14/682,980, Feb. 12, 2018 Notice of Appeal Filed.
U.S. Appl. No. 14/682,980, Jan. 10, 2018 Response after Final Office Action.
U.S. Appl. No. 14/682,980, Aug. 10, 2017 Final Office Action.
U.S. Appl. No. 14/682,980, May 1, 2017 Response to Non-Final Office Action.
U.S. Appl. No. 14/682,980, Dec. 1, 2016 Non-Final Office Action.
U.S. Appl. No. 14/695,674, Feb. 2, 2018 Response to Non-Final Office Action.
U.S. Appl. No. 14/695,674, Nov. 3, 2017 Non-Final Office Action.
U.S. Appl. No. 14/449,820, Nov. 29, 2017 Response to Non-Final Office Action.
U.S. Appl. No. 11/899,004, Nov. 3, 2011 Decision on Petition.
U.S. Appl. No. 11/899,004, Oct. 4, 2011 Petition and Amendment after Notice of Allowance.
U.S. Appl. No. 11/899,004, Sep. 19, 2011 Decision on Petition.
U.S. Appl. No. 12/077,612, Sep. 22, 2014 Amendment and Request for Continued Examination (RCE).
U.S. Appl. No. 12/077,612, Mar. 21, 2014 Final Office Action.
U.S. Appl. No. 12/077,612, Jan. 30, 2014 Response to Non-Final Office Action.
U.S. Appl. No. 12/077,612, Jan. 2, 2014 Applicant Initiated Interview Summary.
U.S. Appl. No. 12/077,612, Oct. 26, 2011 Amendment and Request for Continued Examination (RCE).
U.S. Appl. No. 12/077,612, May 26, 2011 Final Office Action.
U.S. Appl. No. 12/077,612, Mar. 23, 2011 Response to Non-Final Office Action.
U.S. Appl. No. 12/077,612, Nov. 16, 2010 Non-Final Office Action.
U.S. Appl. No. 12/077,612, Aug. 30, 2013 Non-Final Office Action.
U.S. Appl. No. 12/077,612, Oct. 29, 2015 Notice of Abandonment.
U.S. Appl. No. 12/077,612, Apr. 9, 2015 Non-Final Office Action.
U.S. Appl. No. 13/019,029, Dec. 26, 2012 Notice of Allowance.
U.S. Appl. No. 13/019,029, Mar. 21, 2013 Issue Fee payment.
U.S. Appl. No. 13/045,070, Nov. 7, 2013 Amendment and Request for Continued Examination (RCE).
U.S. Appl. No. 13/045,070, May 9, 2013 Final Office Action.

(56) References Cited

OTHER PUBLICATIONS

U.S. Appl. No. 13/045,070, Dec. 21, 2012 Response to Non-Final Office Action.
U.S. Appl. No. 13/045,070, Jun. 22, 2012 Non-Final Office Action.
U.S. Appl. No. 13/045,070, Feb. 24, 2016 Issue Fee Payment.
U.S. Appl. No. 13/045,070, Jan. 15, 2016 Notice of Allowance.
U.S. Appl. No. 13/045,070, Jan. 15, 2016 Applicant Initiated Interview Summary.
U.S. Appl. No. 13/045,070, Jan. 7, 2016 Notice of Appeal Filed.
U.S. Appl. No. 13/045,070, Nov. 17, 2015 Response after Final Action.
U.S. Appl. No. 13/045,070, Jul. 7, 2015 Final Office Action.
U.S. Appl. No. 13/045,070, May 18, 2015 Applicant Initiated Interview Summary.
U.S. Appl. No. 13/045,070, May 15, 2015 Response to Non-Final Office Action.
U.S. Appl. No. 13/045,070, Jan. 16, 2015 Non-Final Office Action.
U.S. Appl. No. 13/353,148, Apr. 24, 2014 Non-Final Office Action.
U.S. Appl. No. 13/353,148, Oct. 17, 2013 Final Office Action.
U.S. Appl. No. 13/353,148, Sep. 11, 2013 Response to Non-Final Office Action.
U.S. Appl. No. 13/353,148, Jun. 20, 2013 Non-Final Office Action.
U.S. Appl. No. 13/353,148, Feb. 26, 2016 Notice of Abandonment.
U.S. Appl. No. 13/353,148, Aug. 12, 2015 Non-Final Office Action.
U.S. Appl. No. 13/353,148, Jul. 6, 2015 Amendment and Request for Continued Examination (RCE).
U.S. Appl. No. 13/353,148, Mar. 3, 2015 Final Office Action.
U.S. Appl. No. 13/353,148, Oct. 24, 2014 Response to Non-Final Office Action.
U.S. Appl. No. 13/353,148, Oct. 14, 2014 Applicant Initiated Interview Summary.
U.S. Appl. No. 13/353,148, Feb. 25, 2014 Applicant Initiated Interview Summary.
U.S. Appl. No. 13/426,400, May 13, 2016 Notice of Allowance.
U.S. Appl. No. 13/426,400, May 5, 2016 Issue Fee Payment.
U.S. Appl. No. 13/426,400, May 5, 2014 Non-Final Office Action.
U.S. Appl. No. 13/426,400, Feb. 5, 2016 Notice of Allowance.
U.S. Appl. No. 13/426,400, Dec. 4, 2015 Applicant Initiated Interview Summary.
U.S. Appl. No. 13/426,400, Dec. 4, 2015 Response to Non-Final Office Action.
U.S. Appl. No. 13/426,400, Jul. 2, 2015 Non-Final Office Action.
U.S. Appl. No. 13/426,400, Mar. 23, 2015 Amendment and Request for Continued Examination (RCE).
U.S. Appl. No. 13/426,400, Dec. 23, 2014 Final Office Action.
U.S. Appl. No. 13/426,400, Oct. 2, 2014 Response to Non-Final Office Action.
U.S. Appl. No. 13/529,239, Sep. 3, 2014 Non-Final Office Action.
U.S. Appl. No. 13/529,239, Jun. 30, 2014 Amendment and Request for Continued Examination (RCE).
U.S. Appl. No. 13/529,239, Dec. 31, 2013 Final Office Action.
U.S. Appl. No. 13/529,239, Dec. 3, 2013 Response to Non-Final Office Action.
U.S. Appl. No. 13/529,239, Nov. 18, 2013 Applicant-Initiated Interview Summary.
U.S. Appl. No. 13/529,239, Jul. 5, 2013 Non-Final Office Action.
U.S. Appl. No. 13/529,239, Jan. 8, 2016 Notice of Abandonment.
U.S. Appl. No. 13/529,239, Jun. 4, 2015 Final Office Action.
U.S. Appl. No. 13/529,239, Mar. 5, 2015 Applicant Initiated Interview Summary.
U.S. Appl. No. 13/529,239, Mar. 3, 2015 Response to Non-Final Office Action.
U.S. Appl. No. 13/848,436, Nov. 1, 2016 Issue Fee Payment.
U.S. Appl. No. 13/848,436, Aug. 2, 2016 Notice of Allowance.
U.S. Appl. No. 13/848,436, Jun. 21, 2016 Response to Non-Final Office Action.
U.S. Appl. No. 13/848,436, Jan. 21, 2016 Non-Final Office Action.
U.S. Appl. No. 13/848,436, Dec. 21, 2015 Response to Restriction Requirement.
U.S. Appl. No. 13/848,436, Jul. 22, 2015 Restriction Requirement.
U.S. Appl. No. 14/091,010, Dec. 1, 2017 Non-Final Office Action.
U.S. Appl. No. 14/091,010, Oct. 18, 2017 Amendment and Request for Continued Examination (RCE).
U.S. Appl. No. 14/091,010, Apr. 20, 2017 Final Office Action.
U.S. Appl. No. 14/091,010, Mar. 13, 2017 Response to Non-Final Office Action.
U.S. Appl. No. 14/091,010, Sep. 12, 2016 Non-Final Office Action.
U.S. Appl. No. 14/300,106, Dec. 22, 2015 Issue Fee Payment.
U.S. Appl. No. 14/300,106, Sep. 24, 2015 Notice of Allowance.
U.S. Appl. No. 14/457,023, Dec. 26, 2017 Response to Non-Final Office Action.
U.S. Appl. No. 14/457,023, Jun. 23, 2017 Non-Final Office Action.
U.S. Appl. No. 14/457,023, Mar. 9, 2017 Amendment and Request for Continued Examination (RCE).
U.S. Appl. No. 14/457,023, Sep. 9, 2016 Final Office Action.
U.S. Appl. No. 14/457,023, Jun. 30, 2016 Response to Non-Final Office Action.
U.S. Appl. No. 14/457,023, Mar. 2, 2016 Non-Final Office Action.
U.S. Appl. No. 14/476,543, Jan. 17, 2018 Amendment and Request for Continued Examination (RCE).
U.S. Appl. No. 14/476,543, Jul. 17, 2017 Final Office Action.
U.S. Appl. No. 14/476,543, Mar. 22, 2017 Response to Non-Final Office Action.
U.S. Appl. No. 14/476,543, Sep. 22, 2016 Non-Final Office Action.
U.S. Appl. No. 14/949,000, Jan. 29, 2018 Amendment and Request for Continued Examination (RCE).
U.S. Appl. No. 14/949,000, Jul. 28, 2017 Final Office Action.
(Multiple Sources) Sixth International Conference on the Measurement and Imaging of Tissue Elasticity. Nov. 2, 2007 [Retrieved on Mar. 12, 2014], pp. 1-154, retrieved from the internet: <URL:http://www.elasticityconference.org/prior_conf/2007/2007Proceedings.pdf>.
"Vial", Retrieved from http://en.wikipedia.org/w/index.php?title=Vial&oldid=603936258 [Downloaded on May 20, 2014].
Abbott, et al., "Astrocyte-Endothelial Interactions at the Blood-Brain Barrier", Nat. Rev. Neurosci., 7(1):41-53 (2006).
Alam et al., "An Adaptive Strain Estimator for Elastography," IEEE Transactions on Ultrasonics, Ferroelectrics, and Frequency Control 45(2):461-472 (1998).
Amin et al., "Therapy planning and monitoring of tissue ablation by high intensity focused ultrasound (HIFU) using imaging and simulation", Conf Proc IEEE Eng Med Biol Soc. 2008, 4471.
Ammi et al., "Ultrasonic contrast agent shell rupture detected by inertial cavitation and rebound signals", IEEE Transactions, 53(1):126-136 (2006).
Ashikaga et al., "Transmural Dispersion of Myofiber Mechanics: Implications for Electrical Heterogeneity In Vivo", Journal of the American College of Cardiology, 49(8):909-916 (2007).
Aubry et al., "Experimental Demonstration of Noninvasive Transskull Adaptive Focusing Based on Prior Computed Tomography Scans", The Journal of the Acoustical Society of America, 113:84 (2003).
Azuma et al., "Bubble Generation by Standing Wave in Water Surrounded by Cranium With Transcranial Ultrasonic Beam", Japanese Journal of Applied Physics, 44:4625-4630 (2005).
Badke et al., "Effects of Ventricular Pacing on Regional Left Ventricular Performance in The Dog", Am J Physiol Heart Circ Physiol., 238:H858-867 (1980).
Baron et al., "Simulation of Intracranial Acoustic Fields in Clinical Trials of Sonothrombolysis", Ultrasound Med. Biol., 35(7):1148-1158 (2009).
Baseri et al., "Multi-Modality Safety Assessment of Blood-Brain Barrier Opening Using Focused Ultrasound and Definity Microbubbles: A Short-Term Study", Ultrasound Med. Biol., 6(9):1445-1459 (2010).
Behrens et al., "Low-Frequency, Low-Intensity Ultrasound Accelerates Thrombolysis Through the Skull", Ultrasound in Medicine & Biology, 25:269-273 (1999).
Berger et al., "Single-Beat Noninvasive Imaging of Cardiac Electrophysiology of Ventricular Pre-Excitation", Journal of the American College of Cardiology, 48:2045-2052 (2006).
Bers, "Cardiac Excitation-Contraction Coupling", Nature ,415:198-205 (2002).

(56) References Cited

OTHER PUBLICATIONS

Borden et al., "Ultrasound Radiation Force Modulates Ligand Availability on Target Contrast Agents", Mol. Imaging, 5:139-147 (2006).
Brundin et al., "Restorative Therapies in Parkinson's Disease", Springer Verlag (2006).
Campbell et al., "Mechanisms of Transmurally Varying Myocyte Electromechanics in an Integrated Computational Model", Philos Transact A Math Phys Eng Sci., 366:3361-3380 (2008).
Carman et al., "Adenosine receptor signaling modulates permeability of the blood-brain barrier", The Journal of Neuroscience, 31(37):13272-13280 (2011).
Caskey et al., "Direct Observations of Ultrasound Microbubble Contrast Agent Interaction With the Microvessel Wall", J. Acoust. Soc. Amer., 122(2):1191-1200 (2007).
Caskey et al., "Microbubble Oscillation in Tubes With Diameters of 12, 25, and 195 Microns", Appl. Phys. Lett., 88(3):033902-1-033902-3 (2006).
Cavaglia et al., "Regional Variation in Brain Capillary Density and Vascular Response to Ischemia", Brain Res., 910(1-2):81-93 (2001).
Chan, "Transgenic Nonhuman Primates for Neurodegenerative Diseases", Reproductive Biology and Endocrinology, 2:39 (2004).
Chen et al., "Architectural Acoustics and Noise: Advancements and Best Practices in Instrumentation for Architectural Acoustics and Noise", J. Acoust. Soc. Am.; 164th Meeting: Acoustical Society of America, 132(3, Pt. 2):1977-2018 (Sep. 2012).
Chen et al., "Engineering Acoustics and ASA Committee on Standards: Sound Intensity Measurements", J. Acoust. Soc. Am.; 164th Meeting: Acoustical Society of America, 132(3, Pt. 2):1984 (Sep. 2012).
Chen et al., "Optimization of Ultrasound Parameters for Cardiac Gene Delivery of Adenoviral or Plasmid Deoxyribonucleic Acid by Ultrasound-Targeted Microbubble Destruction", J. Amer. Coll. Cardiol., 42(2):301-308 (2003).
Chen et al., "The size of blood-brain barrier opening induced by focused ultrasound is dictated by the acoustic pressure", J. Cereb. Blood Flow Metab., 34:1197-1204 (2014).
Choi et al., "Feasibility of Transcranial, Localized Drug-Delivery in the Brain of Alzheimer's-Model Mice Using Focused Ultrasound", 2005 IEEE Ultrasonics Symposium, pp. 988-991 (Sep. 18-21, 2005).
Choi et al., "Focused Ultrasound-Induced Molecular Delivery Through the Blood-Brain Barrier", Presented at the IEEE Symp. Ultrason. Ferroelect. Freq. Control, New York, NY, pp. 1192-1195 (2007).
Choi et al., "Microbubble-size dependence of focused ultrasound-induced blood-brain barrier opening in mice in vivo", IEEE transactions on Biomedical Engineering, 57(1):145-154 (2010).
Choi et al., "Molecules of Various Pharmacologically-Relevant Sizes Can Cross the Ultrasound-Induced Blood-Brain Barrier Opening In Vivo", Ultrasound in Medicine & Biology, 36(1):58-67 (2009).
Choi et al., "Noninvasive, Transcranial and Localized Opening of the Blood-Brain Barrier Using Focused Ultrasound in Mice", Ultrasound in Medicine & Biology, 33(1):95-104 (2007).
Choi et al., "Spatio-Temporal Analysis of Molecular Delivery Through the Blood-Brain Barrier Using Focused Ultrasound", Physics in Medicine and Biology, 52:5509-5530, (2007).
Chomas et al., "Threshold of Fragmentation for Ultrasonic Contrast Agents", J. Biomed. Opt., 6(2):141-150 (2001).
Clarke, et al., "The changes in acoustic attenuation due to in vitro heating", Ultrasound Med Biol 29:127-135 (2003).
Clement et al., "A Hemisphere Array for Non-Invasive Ultrasound Brain Therapy and Surgery", Phys Med Biol., 45:3707-3719 (2000).
Cobbold, R.S.C., "Foundations of biomedical ultrasound", Biomedical Engineering Series, Oxford University Press, pp. 422-423 (2006).
Connor et al., "A Unified Model for the Speed of Sound in Cranial Bone Based on Genetic Algorithm Optimization", Physics in Medicine and Biology, 47:3925-3944 (2002).
Connor, "Simulation Methods and Tissue Property Models for Non-Invasive Transcranial Focused Ultrasound Surgery", Ph.D. Thesis (2005).
Cordeiro et al., "Transmural Heterogeneity of Calcium Activity and Mechanical Function in the Canine Left Ventricle", Am J Physiol. Heart Circ. Physiol., 286:H1471-1479 (2004).
Coyle, "Arterial Patterns of the Rat Rhinencephalon and Related Structures", Exp. Neurol., 49(3): 671-690 (1975).
Coyle, "Spatial Features of the Rat Hippocampal Vascular System", Exp. Neurol., 58(3): 549-561 (1978).
Coyle, "Vascular Patterns of the Rat Hippocampal Formation", Exp. Neurol., 52(3): 447-458 (1976).
Crum et al., "Bjerknes Forces on Bubbles in a Stationary Sound Field", The Journal of the Acoustical Society of America, 57(6):1363-1370 (1975).
Daffertshofer et al., "Transcranial Low-Frequency Ultrasound-Mediated Thrombolysis in Brain Ischemia: Increased Risk of Hemorrhage With Combined Ultrasound and Tissue Plasminogen Activator: Results of a Phase II Clinical Trial", Stroke, 36:1441-146 (2005).
Damianou et al., "Dependence of ultrasonic attenuation and absorption in dog soft tissues on temperature and thermal dose", J Acoust Soc Am, 102(1):628-634 (1997).
Damianou, "In vitro and in vivo ablation of porcine renal tissues using high-intensity focused ultrasound", Ultrasound Med Biol 29:1321-30 (2003).
Datta et al., "Correlation of Cavitation With Ultrasound Enhancement of Thrombolysis", Ultrasound in Medicine & Biology, 32(8): 1257-1267 (2006).
De Craene et al., "Temporal diffeomorphic free-form deformation: Application to motion and strain estimation from 3D echocardiography", Medical Image Analysis, 16(2):427-450 (2012).
Deffieux et al., "Transcranial Focused Ultrasound for Blood-Brain Barrier Opening—Numerical Simulations With In Vitro Validation in Human and Monkey Skulls", Title page and Table of Contents for the AIUM Annual Convention, San Diego, CA, (2010).
Definition of "spatial filter" retrieved from http://www.onelook.com/ on May 26, 2015.
DeLong, "Primate Models of Movement Disorders of Basal Ganglia Origin", Trends Neurosci., 13(7):281-285 (1990).
DuBose et al., "Confusion and Direction in Diagnostic Doppler Sonography", Journal of Diagnostic Medical Sonography, 25(3):173-177 (2009).
Duck, "Physical Properties of Tissue: A Comprehensive Reference Book", Academic Press, London, UK, 1990.
Duerinckx et al., "In vivo acoustic attenuation in liver: correlations with blood tests and histology", Ultrasound Imaging, 14(5):405-413 (1988).
Duerinckx, et al., "Letter to the editor", Ultrasonic Imaging 8:225-226 (1986).
Durrer et al., "Total Excitation of the Isolated Human Heart", Circulation, 41:899-912 (1970).
Erpelding et al., "Bubble-Based Acoustic Radiation Force Using Chirp Insonation to Reduce Standing Wave Effects", Ultrasound in Medicine & Biology, 33(2):263-269 (2007).
European Search Report for EP Application No. 10838238, dated May 6, 2014.
Everbach et al., "Cavitational Mechanisms in Ultrasound-Accelerated Thrombolysis at 1 Mhz", Ultrasound in Medicine & Biology, 26(7):1153-1160 (2000).
Extended European Search Report dated Jan. 23, 2017 in EP Application No. 10818027.
Faris et al., "Novel Technique for Cardiac Electromechanical Mapping With Magnetic Resonance Imaging Tagging and an Epicardial Electrode Sock", Ann Biomed Eng., 31:430-440 (2003).
Farook et al., "Preparation of Microbubble Suspensions by Co-Axial Electrohydrodynamic Atomization", Med. Eng. Phys., 29(7):749-754 (2007).
Fenster et al., "Three-dimensional ultrasound imaging", Phys Med Biol, 46(5):R67-R99 (2001).
Fiske et al., "Special Focus Section: Gene Therapy for Parkinson's Disease", Experimental Neurology, 209:28-29 (2008).

(56) References Cited

OTHER PUBLICATIONS

Fry et al., "A Focused Ultrasound System for Tissue Volume Ablation in Deep Seated Brain Sites", IEEE 1986 Ultrasonics Symposium, pp. 1001-1004 (1986).
Fry, "Transkull Transmission of an Intense Focused Ultrasonic Beam", Ultrasound in Medicine & Biology, 3:179 (1977).
Fujii et al., "A new method for attenuation coefficient measurement in the liver", Journal of Ultrasound Medicine, 21(7):783-788 (2002).
Ganan-Calvo et al., "Perfectly Monodisperse Microbubbling by Capillary Flow Focusing", Phys. Rev. Lett., 87(27) Pt 1: 274501-1-274501-4 (2001).
Gaud et al., "Acoustic Characterization of Single Ultrasound Contrast Agent Microbubbles", The Journal of the Acoustic Society of America, 124(6):4091 (2008).
Ghosh et al., "Cardiac Memory in Patients With Wolff-Parkinson-White Syndrome: Noninvasive Imaging of Activation and Repolarization Before and After Catheter Ablation", Circulation, 118:907-915 (2008).
Giacobini, "Alzheimer Disease, From Molecular Biology to Therapy", Advances in Experimental Medicine and Biology, 429:235-245 (1997).
Ginat et al., "High-Resolution Ultrasound Elastography of Articular Cartilage in Vitro", Proceedings of the 28th IEEE EMBS Annual International Conference, New York City, USA, pp. 6644-6647 (Aug. 30-Sep. 3, 2006).
Greenstein et al., "Mechanisms of Excitation-Contraction Coupling in an Integrative Model of the Cardiac Ventricular Myocyte", Biophysical Journal, 90:77-91 (2006).
Gurev et al., "Distribution of Electromechanical Delay in the Heart: Insights From a Three-Dimensional Electromechanical Model", Biophysical Journal, 99:745-754 (2010).
Gurev et al., "In Silico Characterization of Ventricular Activation Pattern by Electromechanical Wave Imaging", Supplement to Heart Rhythm., 6:S357 (2009).
Housden et al., "Ultrasonic imaging of 3D displacement vectors using a simulated 2D array and beamsteering", Ultrasonics, 53(2):615-621 (2013).
Hynynen et al., "Demonstration of Potential Noninvasive Ultrasound Brain Therapy Through an Intact Skull", Ultrasound in Medicine & Biology, 24(2):275-283 (1998).
Hynynen et al., "Focal Disruption of the Blood-Brain Barrier Due to 260-Khz Ultrasound Bursts: A Method for Molecular Imaging and Targeted Drug Delivery", J. Neurosurg., 105(3):445-454 (2006).
Hynynen et al., "Local and reversible blood-brain barrier disruption by noninvasive focused ultrasound at frequencies suitable for trans-skull sonications" NeuroImage 24:12-20 (2005).
Hynynen et al., "Noninvasive MR Imaging—Guided Focal Opening of the Blood-Brain Barrier in Rabbits", Radiology, 220(3):640-646 (2001).
Hynynen et al., "Trans-Skull Ultrasound Therapy: The Feasibility of Using Image-Derived Skull Thickness Information to Correct the Phase Distortion", IEEE Transactions on Ultrasonics, Ferroelectrics and Frequency Control, 46(3):752-755 (1999).
International Search Report and Written Opinion dated Feb. 3, 2014 in International Application No. PCT/US2013/064377.
International Search Report and Written Opinion for PCT/US2006/036460, dated Sep. 5, 2007; International Preliminary Report dated Mar. 26, 2008.
International Search Report and Written Opinion for PCT/US2009/056513, dated Oct. 30, 2009.
International Search Report and Written Opinion for PCT/US2009/056565 dated Nov. 2, 2009.
International Search Report and Written Opinion for PCT/US2010/049681, dated Dec. 7, 2010.
International Search Report and Written Opinion for PCT/US2010/061742, dated Mar. 1, 2011.
International Search Report and Written Opinion for PCT/US2011/034704, dated Aug. 18, 2011.
International Search Report for PCT/US2014/011631, dated Mar. 31, 2014.
Jagannathan et al., "High-Intensity Focused Ultrasound Surgery of the Brain: Part 1—A Historical Perspective With Modern Applications", Neurosurgery, 64(2):201-211 (2009).
Jasaityte et al., "Current state of three-dimensional myocardial strain estimation using echocardiography", J Am Soc Echocardiogr., 26(1):15-28 (2013).
Jensen et al., "Calculation of Pressure Fields From Arbitrarily Shaped, Apodized, and Excited Ultrasound Transducers", IEEE Transactions on Ultrasonics, Ferroelectrics and Frequency Control, 39(2):262-267 (1992).
Kallel et al., "A Least-Squares Strain Estimator for Elastography", Ultrasonic Imaging, 19:195-208 (1997).
Kaufman et al., "Ultrasound Simulation in Bone," IEEE Transactions on Ultrasonics Ferroelectrics and Frequency Control, 55(6):1205-1218 (2008).
Kimber et al., "A Comparison of Unipolar and Bipolar Electrodes During Cardiac Mapping Studies", Pacing Clin Electro., 19:1196-1204 (1996).
Kinoshita et al., "Noninvasive Localized Delivery of Herceptin to the Mouse Brain by MRI-Guided Focused Ultrasound-Induced Blood-Brain Barrier Disruption", Proceedings of the National Academy of Sciences, 103(31):11719-11723 (2006).
Kinoshita et al., "Targeted Delivery of Antibodies Through the Blood—Brain Barrier by MRI-Guided Focused Ultrasound", Biochemical and Biophysical Research Communications, 340:1085-1090 (2006).
Klein et al., "Interdependency of Local Capillary Density, Blood Flow, and Metabolism in Rat Brains", Amer. J. Physiol., 251(6) Pt 2:H1333-H1340 (1986).
Klempner et al., "Neutrophil Plasma Membranes I. High-Yield Purification of Human Neutrophil Plasma Membrane Vesicles by Nitrogen Cavitation and Differential Centrifugation", Journal of Cell Biology, 86:21-28 (1980).
Konofagou et al., "Electromechanical Wave Imaging for Noninvasive Mapping of the 3D Electrical Activation Sequence in Canines and Humans In Vivo", Journal of Biomechanics, 45(5):856-864 (2012).
Konofagou et al., "Mechanism and Safety at the Threshold of the Blood-Brain Barrier Opening In Vivo", International Society on Therapeutic Ultrasound (ISTU), Aix-en-Provence, France, Sep. 21-24, 2009.
Konofagou et al., "Noninvasive electromechanical wave imaging and conduction-relevant velocity estimation in vivo", Ultrasonics, 50(2):208-215 (2010).
Konofagou et al., "Noninvasive Electromechanical Wave Imaging and Conduction Velocity Estimation In Vivo", 2007 IEEE Ultrasonics Symposium, pp. 969-972 (2007).
Konofagou et al., "Ultrasound-Induced Blood-Brain Barrier Opening", Current Pharmaceutical Biotechnology, 13(7):1332-1345 (2012).
Korecka et al., "Cell-Replacement and Gene-Therapy Strategies for Parkinson's and Alzheimers Disease", Regen. Med., 2(4):425-446 (2007).
Kremkau et al., "Ultrasonic Attenuation and Propagation Speed in Normal Human Brain", The Journal of the Acoustical Society of America, 70:29 (1981).
Kunz et al., "The Finite Difference Time Domain Method for Electromagnetics," CRC Press, Boca Raton, USA (1993).
Kvale et al., "Size Fractionation of Gas-Filled Microspheres by Flotation", Separations Technol., 6(4):219-226 (1996).
Lai et al., "Introduction to Continuum Mechanics", (Pergamon Pr). 3rd Ed. (1993).
et al., "Improving Stereotactic Surgery Using 3-D Reconstruction", IEEE Engineering in Medicine and Biology Magazine, 21:109-116 (2002).
Lee et al., "Theoretical Quality Assessment of Myocardial Elastography With In Vivo Validation", IEEE Transactions, Ultrasonics, Ferroelectrics and Frequency Control, 54:2233-2245 (2007).
Liu et al., "Hemorrhage Detection During Focused-Ultrasound Induced Blood-Brain-Barrier Opening by Using Susceptibility-Weighted Magnetic Resonance Imaging", Ultrasound in Med. & Biol., 34(4):598-606 (2008).
Liu et al., "Magnetic Resonance Imaging Enhanced by Superparamagnetic Iron Oxide Particles: Usefulness for Distinguish-

(56) References Cited

OTHER PUBLICATIONS ing Between Focused Ultrasound-Induced Blood-Brain Barrier Disruption and Brain Hemorrhage", J. of Magnetic Resonance Imaging, 29:31-38 (2009).
Liu et al., "Opening of the Blood-Brain Barrier by Low-Frequency (28-kHz) Ultrasound: A Novel Pinhole-Assisted Mechanical Scanning Device", Ultrasound in Med & Biol., 36(2):325-335 (2010).
Long et al., "An integrated system for therapy planning of high intensity focused ultrasound", Electro/Information Technology, 2008. EIT 2008. IEEE International Conference on May 18-20, 2008, pp. 461-464.
Lu et al., "Design and Experiment of 256-Element Ultrasound Phased Array for Noninvasive Focused Ultrasound Surgery", Ultrasonics, 44:e325-e330 (2006).
Luo et al., "A Fast Normalized Cross-Correlation Method for Motion Estimation", IEEE Transactions, Ultrasonics, Ferroelectrics and Frequency Control, 57(6):1347-1357 (2010).
Luo et al., "High-Frame Rate, Full-View Myocardial Elastography With Automated Contour Tracking in Murine Left Ventricles In Vivo", IEEE Transactions, Ultrasonics, Ferroelectrics and Frequency Control, 55(1):240-248 (2008).
Luo et al., "Pulse Wave Imaging of Normal and Aneurysmal Abdominal Aortas In Vivo", IEEE Trans. Med. Imaging, 28(4):477-486 (2009).
Maleke et al., "In Vivo Feasibility of Real-Time Monitoring of Focused Ultrasound Surgery (FUS) Using Harmonic Motion Imaging (HMI)", IEEE Trans. Biomed. Eng., 57(1):7-11 (2010).
Maleke et al., "Single-Element Focused Ultrasound Transducer Method for Harmonic Motion Imaging", Ultrasonic Imaging, 28(3):144-158 (2006).
Marquet et al., "Non-Invasive Transcranial Ultrasound Therapy Based on a 3D CT Scan: Protocol Validation and In Vitro Results", Phys. Med. Biol., 54:2597-2613 (2009).
Mazziotta et al., "A Probabilistic Atlas of the Human Brain: Theory and Rationale for Its Development the International Consortium for Brain Mapping (ICBM)", Neuroimage, 2:89-101 (1995).
McDannold et al., "MRI-Guided Targeted Blood-Brain Barrier Disruption With Focused Ultrasound: Histological Findings in Rabbits", Ultrasound Med. Biol., 31(11):1527-1537 (2005).
McDannold et al., "Targeted Disruption of the Blood-Brain Barrier With Focused Ultrasound: Association With Cavitations Activity", Physics in Medicine and Biology, 51:793-808 (2006).
McDannold et al., "Use of Ultrasound Pulses Combined With Definity for Targeted Blood-Brain Barrier Disruption: A Feasibility Study", Ultrasound in Medicine & Biology, 33(4):584-590 (2007).
Melodelima et al., "Thermal Ablation by High-Intensity-Focused Ultrasound Using a Toroid Transducer Increases the Coagulated Volume. Results of Animal Experiments", Ultrasound in Medicine & Biology, 35(3):425-435 (2009).
Mitri et al., "Chirp Imaging Vibro-Acoustography for Removing the Ultrasound Standing Wave Artifact", IEEE Transactions on Medical Imaging, 24(10):1249-1255 (2005).
Mychaskiw et al., "Optison (FS069) Disrupts the Blood-Brain Barrier in Rats", Anesthesia & Analgesia, 91:798 (2000).
Ophir et al., "Elastography: A Quantitative Method for Imaging the Elasticity of Biological Tissues", Ultrasonic Imaging, 3(2):111-134 (1991).
Otani et al., "Transmural Ultrasound-Based Visualization of Patterns of Action Potential Wave Propagation in Cardiac Tissue", Annals Biomedical Engineering, 38(10):3112-3123 (2010).
Otani et al., "Transmural Ultrasound-based Visualization of Patters of Action Potential Wave Propagation in Cardiac Tissue," Annals of Biomedical Engineering 38(10):3112-3123 (2010).
Otani, "Use of ultrasound imaging to map propagating action potential waves in the heart", Computers in Cardiology, 36:617-620 (2009).
Palmeri et al., "Characterizing acoustic attenuation of homogeneous media using focused impulsive acoustic radiation force", Ultrason Imaging, 28(2):114-128 (2006).

Papadakis, "Ultrasonic Instruments & Devices", Academic Press, 8 pages (1999).
Pardridge, "Drug Targeting to the Brain", Pharmaceutical Research, 24:1733-1744 (2007).
Pardridge, "The Blood-Brain Barrier: Bottleneck in Brain Drug Development", NeuroRx, 2:3-14 (2005).
Parker, "Ultrasonic-attenuation and absorption m liver-tissue", Ultrasound Med Biol 9:363-369 (1983).
Patel et al., "GDNF Delivery for Parkinson's Disease", ACTA Neurochir Suppl 97(2):135-154 (2007).
Pernot et al., "ECG-Gated, Mechanical and Electromechanical Wave Imaging of Cardiovascular Tissues In Vivo", Ultrasound in Medicine & Biology, 33(7):1075-1085 (2007).
Pernot et al., "Electromechanical Imaging of the Myocardium at Normal and Pathological States", 2005 IEEE Ultrasonics Symposium, pp. 1091-1094 (2005).
Philippens, "Non-Human Primate Models for Parkinson's Disease", Drug Discovery Today: Disease Models, 5:105-111 (2008).
Pichardo et al., "Multi Frequency Characterization of Speed of Sound for Longitudinal Transmission on Freshly Excised Human Skulls," 9th International Society on Therapeutic Ultrasound, p. 136 (2009).
Prinzen et al., "The Time Sequence of Electrical and Mechanical Activation During Spontaneous Beating and Ectopic Stimulation", Eur. Heart J., 13:535-543 (1992).
Provost et al., "Electromechanical Wave Imaging of Normal and Ischemic Hearts In Vivo", IEEE Trans. Med. Imaging, 29:625-635 (2010).
Provost et al., "Imaging the electromechanical activity of the heart in vivo", PNAS, 108(21):8565-8570 (2011).
Provost et al., "Mapping of cardiac electrical activation with electromechanical wave imaging: An in silico-in vivo reciprocity study", Heart Rhythm., 8(5):752-759 (2011).
Ramanathan et al., "Activation and Repolarization of the Normal Human Heart Under Complete Physiological Conditions", Proceedings of the National Academy of Sciences, 103:6309-6314(2006).
Ramanathan et al., "Noninvasive Electrocardiographic Imaging for Cardiac Electrophysiology and Arrhythmia", Nat Med., 10:422-428 (2004).
Raymond et al., "Ultrasound Enhanced Delivery of Molecular Imaging and Therapeutic Agents in Alzheimer's Disease Mouse Models", PLoS One, 3(5):e2175 (2008).
Rice et al., "Approximate Model of Cooperative Activation and Crossbridge Cycling in Cardiac Muscle Using Ordinary Differential Equations", Biophys. J., 95:2368-2390 (2008).
Rockenstein et al., "Transgenic Animal Models of Neurodegenerative Diseases and Their Application to Treatment Development", Adv. Drug Del. Rev., 59(11):1093-1102 (2007).
Sabraoui et al., "Feedback Loop Process to Control Acoustic Cavitation", Ultrasonics Sonochemistry, 18(2):589-594 (2011).
Samuel et al., "An Ex Vivo Study of the Correlation Between Acoustic Emission and Microvascular Damage", Ultrasound Med. Biol., 35(9):1574-1586 (2009).
Sanberg et al., "Brief Communication: Neural Transplants Disrupt the Blood-Brain Barrier and Allow Peripherally Acting Drugs to Exert a Centrally Mediated Behavioral Effect", Experimental Neurology, 102:149-152 (1988).
Schenk et al., "Immunization With Amyloid-Beta Attenuates Alzheimer-Disease-Like Pathology in the PDAPP Mouse", Nature, 400:173-177 (1999).
Scher et al., "The Pathway of Ventricular Depolarization in the Dog", Circ Res., 4:461-469 (1956).
Schilling et al., "Simultaneous Endocardial Mapping in the Human Left Ventricle Using a Noncontact Catheter: Comparison of Contact and Reconstructed Electrograms During Sinus Rhythm", Circulation, 98:887-98 (1998).
Sengupta et al., "Electromechanical Activation Sequence in Normal Heart", Heart Fail Clin., 4:303-314 (2008).
Sheeran et al., "Formulation and Acoustic Studies of a New Phase-Shift Agent for Diagnostic and Therapeutic Ultrasound," Langmuir, 27(17):10412-10420 (2011).

(56) References Cited

OTHER PUBLICATIONS

Shehata et al., "Myocardial Tissue Tagging With Cardiovascular Magnetic Resonance", Journal of Cardiovascular Magnetic Resonance, 11:55 (2009).
Sheikov et al., "Brain Arterioles Show More Active Vesicular Transport of Blood-Borne Tracer Molecules Than Capillaries and Venules After Focused Ultrasound-Evoked Opening of the Blood-Brain Barrier", Ultrasound Med. Biol., 32(9):1399-1409 (2006).
Sheikov et al., "Cellular Mechanisms of the Blood-Brain Barrier Opening Induced by Ultrasound in Presence of Microbubbles", Ultrasound Med. Biol., 30(7):979-989 (2004).
Sheikov et al., "Effect of Focused Ultrasound Applied With an Ultrasound Contrast Agent on the Tight Junctional Integrity of the Brain Microvascular Endothelium", Ultrasound Med. Biol., 34(7):1093-1104 (2008).
Shiinna et al., "Realtime tissue elasticity imaging using the combined autocorrelation method", J. Med. Ultrasonics, 29(autumn):119-128 (2002).
Siegel et al., "Neurotrophic Factors in Alzheimer's and Parkinson's Disease Brain", Brain Research Reviews, 33:199-227 (2000).
Sirsi et al., "Effect of Microbubble Size on Fundamental Mode High Frequency Ultrasound Imaging in Mice", Ultrasound in Med. & Bio., 36(6):935-948 (2010).
Spalazzi et al., "Elastographic Imaging of Strain Distribution within the Anterior Cruciate Ligament and at the AGL-Bone Insertions," IEEE Ultrasonics Symposium, Sep. 2005, pp. 1755-1758.
Stewart et al., "Blood-Eye Barriers in the Rat: Correlation of Ultrastructure With Function", J. Comp. Neurol., 340(4):566-576 (1994).
Stieger et al., "Enhancement of Vascular Permeability With Low-Frequency Contrast-Enhanced Ultrasound in the Chorioallantoic Membrane Model", Radiology, 243(1): 112-121 (2007).
Styner et al., "Automatic Brain Segmentation in Rhesus Monkeys", 2007 Medical Imaging, Proc. of SPIE, 6512:65122L-1-65122L-8 (2007).
Suzuki, et al., "Dependence of ultrasonic attenuation of liver on pathological fat and fibrosis: examination with experimental fatty liver and liver fibrosis models", Ultrasound Med Biol. 18:657-666 (1992).
Sykova et al., "Diffusion in Brain Extracellular Space", Physiol. Rev., 88(4):1277-1340 (2008).
Talu et al., "Tailoring the Size Distribution of Ultrasound Contrast Agents: Possible Method for Improving Sensitivity in Molecular Imaging" Mol. Imag., 6(6):384-392 (2007).
Tang et al., "Standing-Wave Suppression for Transcranial Ultrasound by Random Modulation", IEEE Transactions on Biomedical Engineering, 57(1):203-205 (2010).
Tanter et al., "Focusing and Steering Through Absorbing and Aberrating Layers: Application to Ultrasonic Propagation Through the Skull", The Journal of the Acoustical Society of America, 103:2403-2410 (1998).
Tavarozzi et al., "Magnetocardiography: Current Status and Perspectives Part II: Clinical Applications", Ital Heart J., 3:151-165 (2002).
Techavipoo et al., "Temperature dependence of ultrasonic propagation speed and attenuation in excised canine liver tissue measured using transmitted and reflected pulses", The Journal of Acoustical Society of America, 115(6):2859-2865 (2004).
Treat et al., "Targeted Delivery of Doxorubicin to the Rat Brain at Therapeutic Levels Using MRI-Guided Focused Ultrasound", Int. J. Cancer, 121(4):901-907 (2007).
Tung et al., "Feasibility of Noninvasive Cavitation-Guided Blood-Brain Barrier Opening Using Focused Ultrasound and Microbubbles in Nonhuman Primates", Applied Physics Letters, 98(16):163704 (2001).
Tung et al., "Identifying the Inertial Cavitation Threshold and Skull Effects in a Vessel Phantom Using Focused Ultrasound and Microbubbles", Ultrasound in Medicine & Biology, 36(5):840-852 (2010).

Tung et al., "Identifying the Inertial Cavitation Threshold in a Vessel Phantom Using Focused Ultrasound and Microbubbles", The Journal of the Acoustical Society of America, 124:2486 (2008).
Tung et al., "Noninvasive In Vivo Cavitation Threshold Detection During Blood-Brain Barrier Opening Using Focused Ultrasound and the Contrast Agent and Definity", Joint 159th Meeting of the Acoustic Society of America, (Apr. 19, 2010).
Tuszynski et al., "A Phase 1 Clinical Trial of Nerve Growth Factor Gene Therapy for Alzheimer Disease", Nature Medicine, 11:551-555 (2005).
Tuszynski et al., "Nerve Growth Factor Gene Therapy in Alzheimer Disease," Alzheimer Disease & Associated Disorders, 21:179-189 (2007).
Tyreus, et al., "Two-dimensional acoustic attenuation mapping of high-temperature interstitial ultrasound lesions", Phys Med Biol 49:533-46 (2004).
Vaezy et al., "Real-time visualization of high-intensity focused ultrasound treatment using ultrasound imaging", Ultrasound Med Biol., 27(1):33-42 (2001).
Vappou et al., "Quantitative Viscoelastic Parameters Measured by Harmonic Motion Imaging", Phys. Med. Biol., 54:3579-3595 (2009).
Walker et al., "A Fundamental Limit on the Performance of Correlation Based Phase Correction and Flow Estimation Techniques", IEEE Transactions, Ultrasonics, Ferroelectrics and Frequency Control, 41(5):644-654 (1994).
Wang et al., "Qualitative and Quantitative Analysis of the Molecular Delivery Through the Ultrasound-Enhanced Blood-Brain Barrier Opening in the Murine Brain," presented at the IEEE Symp. Ultrason. Ferroelectr. Freq. Control, Beijing, China, 2008.
Wenk, "A Primate Model of Alzheimer's Disease", Behavioural Brain Research, 57:117-122 (1993).
White et al., "Longitudinal and Shear Mode Ultrasound Propagation in Human Skull Bone", Ultrasound in Medicine & Biology, 32:1085-1096 (2006).
Wyman et al., "Mapping Propagation of Mechanical Activation in the Paced Heart With MRI Tagging", Am J Physiol Heart Circ Physiol, 276:H881-891 (1999).
Xu et al., "Controllable Gas-Liquid Phase Flow Patterns and Monodisperse Microbubbles in a Microfluidic T-Junction Device", Appl. Phys. Lett., 88(13):133506-1-133506-3 (2006).
Yin et al., "A Numerical Study of Transcranial Focused Ultrasound Beam Propagation at Low Frequency", Physics in Medicine and Biology, 50:1821-1836 (2005).
Zhang et al., "Noninvasive Three-Dimensional Electrocardiographic Imaging of Ventricular Activation Sequence", Am J Physiol Heart Circ Physiol., 289:H2724-32 (2005).
Zheng et al., "A Targeting Method Based on Acoustic Backscatter for Treatment Planning in Tissue Ablation Using Focused Ultrasound", IEEE Trans on Biomed Eng. 57(1):71-79 (2010).
Zheng et al., "Ultrasonic measurement of depth-dependent transient behaviors of articular cartilage under compression", Journal of Biomechanics, 38:1830-1837 (2005).
Zheng et al., "Ultrasound-Driven Microbubble Oscillation and Translation Within Small Phantom Vessels", Ultrasound Med. Biol., 33(12):1978-1987 (2007).
Ziadloo et al., "Real-Time 3D Image-Guided HIFU Therapy", 30th Annual International IEEE EMBS Conference, Canada pp. 4459-4462 (2008).
Zlokovic, "The Blood-Brain Barrier in Health and Chronic Neurodegenerative Disorders", Neuron, 57(2):178-201 (2008).
Zwanenburg et al., "Timing of Cardiac Contraction in Humans Mapped by High-Temporal-Resolution MRI Tagging: Early Onset and Late Peak of Shortening in Lateral Wall", Am J Physiol Heart Circ Physiol., 286:H1872-1880 (2004).
U.S. Appl. No. 11/899,004, filed Aug. 30, 2007, Konofagou, et al.
U.S. Appl. No 12/096,254, filed Nov. 26, 2008, Konofagou, et al.
U.S. Appl. No. 11/433,510 (U.S. Pat. No. 8,858,441), filed May 12, 2006 (Oct. 14, 2014).
U.S. Appl. No. 11/697,573 (US 2007/0276245), filed Apr. 6, 2007 (Nov. 29, 2007) Abandoned.
U.S. Appl. No. 11/697,579 (US 2007/0276242), filed Apr. 6, 2007 (Nov. 29, 2007) Abandoned.

(56) References Cited

OTHER PUBLICATIONS

U.S. Appl. No. 11/899,004 (U.S. Pat. No. 8,150,128), filed Aug. 30, 2007 (Apr. 3, 2012).
U.S. Appl. No. 12/096,254 (US 2009/0221916), filed Nov. 26, 2008 Abandoned.
U.S. Appl. No. 14/449,820 (US 2014/0343424), filed Aug. 1, 2014 (Nov. 20, 2014).
U.S. Appl. No. 11/899,004, Jan. 3, 2012 Issue Fee Payment.
U.S. Appl. No. 11/899,004, Oct. 3, 2011 Notice of Allowance.
U.S. Appl. No. 11/899,004, Sep. 23, 2011 Amendment and Request for Continued Examination (RCE).
U.S. Appl. No. 11/899,004, Jul. 18, 2011 Notice of Allowance.
U.S. Appl. No. 11/899,004, May 10, 2011 Response to Non-Final Office Action.
U.S. Appl. No. 11/899,004, Feb. 8, 2011 Non-Final Office Action.
U.S. Appl. No. 11/697,579, Nov. 28, 2011 Notice of Abandonment.
U.S. Appl. No. 11/697,579, Apr. 29, 2011 Final Office Action.
U.S. Appl. No. 11/697,579, Feb. 7, 2011 Response to Non-Final Office Action.
U.S. Appl. No. 11/697,579, Aug. 6, 2010 Non-Final Office Action.
U.S. Appl. No. 11/697,579, May 17, 2010 Response to Final Office Action.
U.S. Appl. No. 11/697,579, Nov. 17, 2009 Non-Final Office Action.
U.S. Appl. No. 11/697,579, Oct. 15, 2009 Amendment and Request for Continued Examination (RCE).
U.S. Appl. No. 11/697,579, Jul. 15, 2009 Response to Final Office Action.
U.S. Appl. No. 11/697,579, Apr. 15, 2009 Final Office Action.
U.S. Appl. No. 11/697,579, Jan. 16, 2009 Response to Non-Final Office Action.
U.S. Appl. No. 11/697,579, Jul. 18, 2008 Non-Final Office Action.
U.S. Appl. No. 11/697,573, Jan. 12, 2015 Notice of Abandonment.
U.S. Appl. No. 11/697,573, Jun. 16, 2014 Non-Final Office Action.
U.S. Appl. No. 11/697,573, Apr. 17, 2014 Amendment and Request for Continued Examination (RCE).
U.S. Appl. No. 11/697,573, Feb. 21, 2014 Applicant Initiated Interview Summary.
U.S. Appl. No. 11/697,573, Oct. 17, 2013 Final Office Action.
U.S. Appl. No. 11/697,573, Sep. 4, 2013 Response to Non-Final Office Action.
U.S. Appl. No. 11/697,573, May 10, 2013 Non-Final Office Action.
U.S. Appl. No. 11/697,573, Jan. 18, 2013 Amendment and Request for Continued Examination (RCE).
U.S. Appl. No. 11/697,573, Jul. 18, 2012 Final Office Action.
U.S. Appl. No. 11/697,573, Jun. 27, 2012 Response to Non-Final Office Action.
U.S. Appl. No. 11/697,573, Jan. 26, 2012 Non-Final Office Action.
U.S. Appl. No. 11/697,573, Aug. 18, 2011 Amendment and Request for Continued Examination (RCE).
U.S. Appl. No. 11/697,573, Mar. 18, 2011 Final Office Action.
U.S. Appl. No. 11/697,573, Dec. 22, 2010 Response to Non-Final Office Action.
U.S. Appl. No. 11/697,573, Jun. 23, 2010 Non-Final Office Action.
U.S. Appl. No. 11/433,510, Jul. 23, 2014 Issue Fee Payment.
U.S. Appl. No. 11/433,510, Apr. 23, 2014 Notice of Allowance.
U.S. Appl. No. 11/433,510, Apr. 7, 2014 Applicant Initiated Interview Summary.
U.S. Appl. No. 11/433,510, Apr. 4, 2014 Response to Non-Final Office Action.
U.S. Appl. No. 11/433,510, Oct. 4, 2013 Non-Final Office Action.
U.S. Appl. No. 11/433,510, Mar. 30, 2012 Request for Continued Examination (RCE).
U.S. Appl. No. 11/433,510, Mar. 28, 2012 Advisory Action.
U.S. Appl. No. 11/433,510, Dec. 29, 2011 Amendment and Request for Continued Examination (RCE).
U.S. Appl. No. 11/433,510, Sep. 30, 2011 Final Office Action.
U.S. Appl. No. 11/433,510, May 23, 2011 Response to Non-Final Office Action.
U.S. Appl. No. 11/433,510, Jan. 21, 2011 Non-Final Office Action.
U.S. Appl. No. 11/433,510, Oct. 28, 2010 Response to Non-Final Office Action.
U.S. Appl. No. 11/433,510, Apr. 28, 2010 Non-Final Office Action.
U.S. Appl. No. 11/433,510, Apr. 13, 2010 Amendment and Request for Continued Examination (RCE).
U.S. Appl. No. 11/433,510, Nov. 12, 2009 Final Office Action.
U.S. Appl. No. 11/433,510, Aug. 6, 2009 Response to Non-Final Office Action.
U.S. Appl. No. 11/433,510, Mar. 17, 2009 Non-Final Office Action.
U.S. Appl. No. 12/096,254, Sep. 28, 2015 Notice of Abandonment.
U.S. Appl. No. 12/096,254, Feb. 27, 2015 Non-Final Office Action.
U.S. Appl. No. 12/096,254, Sep. 22, 2014 Amendment and Request for Continued Examination (RCE).
U.S. Appl. No. 12/096,254, Mar. 21, 2014 Final Office Action.
U.S. Appl. No. 12/096,254, Dec. 23, 2013 Response to Non-Final Office Action.
U.S. Appl. No. 12/096,254, Dec. 17, 2013 Applicant Initiated Interview Summary.
U.S. Appl. No. 12/096,254, Aug. 23, 2013 Non-Final Office Action.
U.S. Appl. No. 12/096,254, Nov. 30, 2012 Amendment and Request for Continued Examination (RCE).
U.S. Appl. No. 12/096,254, May 31, 2012 Final Office Action.
U.S. Appl. No. 12/096,254, Apr. 4, 2012 Response to Non-Final Office Action.
U.S. Appl. No. 12/096,254, Oct. 5, 2011 Non-Final Office Action.
Avolio, A. P., S. G. Chen, R. P. Wang, C. L. Zhang, M. F. Li and M. F. O'Rourke. Effects of aging on changing arterial compliance and left ventricular load in a northern Chinese urban community. Circulation (1983) 68(1): 50-8.
Bercoff, J., Tanter, M., and Fink, M. (2004). Supersonic shear imaging: A new technique for soft tissue elasticity mapping. IEEE Transactions on Ultrasonics Ferroelectrics and Frequency Control 51, 396-409.
Bonnefous, O. and P. Pesque. Time domain formulation of pulse-Doppler ultrasound and blood velocity estimation by cross correlation. Ultrason Imaging (1986) 8(2): 73-85.
Brekke, S.; Tegnander, E.; Torp, H. G.; Eik-Nes, S. H.; "Tissue Doppler gated (TDOG) dynamic three-dimensional ultrasound imaging of the fetal heart," Ultrasound Obstet Gynecol 2004 vol. 24(2); pp. 192-198.
Brooks, D. H., and MacLeod, R. S. (1997). Electrical imaging of the heart. Ieee Signal Processing Magazine 14, 24-42.
Chang et al. 3-D US Frame Positioning Using Speckle Decorrelation and Image Registration, Jun. 2003, Ultrasound in Medicine and Biology, pp. 801-812.
Chen, Q. et al. "Estimation of Displacement Vectors and Strain Tensors in Elastography Using Angular Insonifications." IEEE Transactions on Medical Imaging, vol. 23, No. 12, pp. 1479-1489 (Dec. 1, 2004).
Choi et al. et al. Brain region and microbubble-size dependence of the focused ultrasound-induced blood-brain barrier opening in mice in vivo. IEEE International Ultrasonics Symposium, Rome, ITA, Sep. 20-23, 2009.
Choi JJ, Wang S, Brown TR, Small SA, Duff KE and Konofagou EE, "Noninvasive and Transient Blood-Brain Barrier Opening in the Hippocampus of Alzheimer's Double Transgenic Mice Using Pulsed Focused Ultrasound", Ultrasonic Imaging, 189-200, 2008.
Choi JJ, Wang S, Tung Y-S, Baseri B, Morrison B 3rd, Konofagou EE. "Delivery of pharmacologically-relevant sized molecules through the ultrasound-induced blood-brain barrier opening in vivo.", Neuroscience, Chicago, IL, USA, Oct. 17-21, 2009.
Choi, J.J. et al., "Optimization of Blood-Brain Barrier Opening in Mice using Focused Ultrasound.", 2006 IEEE Ultrasounics Symposium [online], Jun. 2007.
Cutnell, J. and W. Kenneth (1998). Physics, Fourth Edition. New York. Table of Contents.
Declerck, J., T. S. Denney, C. Ozturk, W. O'Dell and E. R. McVeigh. Left ventricular motion reconstruction from planar tagged MR images: a comparison. Phys Med Biol (2000) 45(6): 1611-1632.
Edwards, C. H., Rankin, J. S., Mchale, P. A., Ling, D., and Anderson, R. W. (1981). Effects of Ischemia on Left-Ventricular Regional Function in the Conscious Dog. American Journal of Physiology 240, H413-H420.

(56) References Cited

OTHER PUBLICATIONS

EPO Search Report & Opinion and Office Action for EP0684017.2 dated Dec. 7, 2009 & Mar. 8, 2010.
Epstein-Barash et al., "A microcomposite hydrogel for repeated on-demand ultrasound-triggered drug delivery," Biomaterials, Mar. 29, 2010, 31: pp. 5208-5217.
Feshitan, J.A. et al., "Microbubble size isolation by differential centrifugation", Journal of Colloid and Interface Science 329 (2009) 316-324.
Fung, Y. C. (1993). Biomechanics—Mechanical Properties of Living Tissues. New York. Table of Contents.
Greenwald, S. E. Pulse pressure and arterial elasticity. Qjm—an International Journal of Medicine (2002) 95(2): 107-112.
Gupta, K. B., Ratcliffe, M. B., Fallert, M. A., Edmunds, L. H., and Bogen, D. K. (1994). Changes in Passive Mechanical Stiffness of Myocardial Tissue with Aneurysm Formation. Circulation 89, 2315-2326.
Heimdal, A., A. Stoylen, H. Torp and T. Skjaerpe. Real-time strain rate imaging of the left ventricle by ultrasound. J Am Soc Echocardiog (1998) 11(11): 1013-1019.
Henderson, A., Parmley, W. W., and Sonnenbl, E. (1971). Series Elasticity of Heart Muscle During Hypoxia. Cardiovascular Research 5, 10-14.
Huang et al. Watershed Segmentation for Breast Tumor in 2-D Sonography, May 2004, Ultrasound in Medicine and Biology, pp. 625-632.
International Preliminary Report on Patentability for PCT/US05/037670 dated Apr. 17, 2007, including the Written Opinion of the International Searching Authority dated Nov. 22, 2006.
International Preliminary Report on Patentability for PCT/US05/37669 dated Apr. 17, 2007, including the Written Opinion of the International Searching Authority dated Jun. 13, 2006.
International Preliminary Report on Patentability for PCT/US06/018454 dated Nov. 14, 2007, including the Written Opinion of the International Searching Authority dated Aug. 9, 2007.
International Preliminary Report on Patentability for PCT/US06/061809 dated Jun. 11, 2008, including the Written Opinion of the International Searching Authority dated Oct. 4, 2007.
International Preliminary Report on Patentability for PCT/US07/019149 dated Mar. 3, 2009, including the Written Opinion of the International Searching Authority dated Feb. 29, 2008.
International Search Report and Written Opinion for International Application No. PCT/US12/34136.
International Search Report and Written Opinion for International Application No. PCT/US12/35685.
International Search Report and Written Opinion of the International Searching Authority for PCT/US09/052563 dated Oct. 8, 2009.
International Search Report for PCT/US05/037669 dated Jun. 13, 2006.
International Search Report for PCT/US05/037670 dated Nov. 22, 2006.
International Search Report for PCT/US06/061809 dated Oct. 4, 2007.
International Search Report for PCT/US07/019149 dated Feb. 29, 2008.
Kanai, H. and Y. Koiwa. Myocardial rapid velocity distribution. Ultrasound Med Biol (2001) 27(4): 481-498.
Kanai, H. Propagation of spontaneously actuated pulsive vibration in human heart wall and in vivo viscoelasticity estimation. Ieee T Ultrason Ferr (2005) 52(11): 1931-1942.
Kanai, H., A. Umezawa and Y. Koiwa (2000). Transcutaneous measurement of frequency dispersion in the regional pulse wave velocity. IEEE Ultrasonics symposium.
Kanai, H., H. Satoh, K. Hirose and N. Chubachi. A New Method for Measuring Small Local Vibrations in the Heart Using Ultrasound. Ieee T Bio-Med Eng (1993) 40(12): 1233-1242.
Konofagou E E et al. "Elastographic Imaging of the Strain Distribution at the Anterior Cruciate Ligament and ACL-Bone Insertions" 27th Annual International Conference of the Engineering in Medicine and Biology Society, pp. 972-975 (Shanghai, China Sep. 1-4, 2005).
Konofagou E.E. and Ophir, J., (1998) A New Elastographic Method for Estimation and Imaging of Lateral Strains, Corrected Axial Strains and Poison's Ratios in Tissues, Ultrasound in Medicine and Biology 24(8), 1183-1199.
Konofagou E.E., D'Hooge J.D., Ophir, J Myocardial Elastography—Feasibility Study In Vivo. Ultrasound Med & Biol., vol. 28, No. 4, pp. 475-482 (2002).
Konofagou E.E., Kallel F. and Ophir J., (1998) Three-dimensional Motion estimation in Elastography, IEEE Proceedings of the Symposium of Ultrasonics, Ferroelectrics and Frequency Control in Sendai, Japan, 1745-1748.
Luo J, Fujikura K., Homma S, Konofagou EE (Aug 2007). Myocardial elastography at both high temporal and spatial resolution for the detection of infarcts. Ultrasound in Medicine & Biology 33(8): 1206-23.
McDannold, N. et al., "Blood-Brain Barrier Disruption Induced by Focused Ultrasound and Circulating Preformed Microbubbles Appears to be Characterized by the Mechnical Index.", Ultrasound Med Biol. Jan. 2008, v. 34(5), pp. 834-840.
McLaughlin, J., M. McNeill, B. Braun and P. D. McCormack. Piezoelectric sensor determination of arterial pulse wave velocity. Physiol Meas (2003) 24(3): 693-702.
McNally, D. et al. "Computer Vision Elastography: Speckle Adaptive Motion Estimation for Elastography Using Ultrasound Sequences." IEEE Transactions on Medical Imaging, vol. 24, No. 6, pp. 755-766 (2005).
Nichols, W. and M. F. O'Rourke (1998). Vascular impedance.In McDonald's: blood flow in arteries: theoretical, experimental and clinical principles. E. Arnold. London. Table of Contents.
Notification of Transmittal of the International Search Report and the Written Opinion of the International Searching Authority, or the Declaration International Application No. PCT/US06/18454 dated Aug. 9, 2007.
Qin, S. and Ferrara, K.W., "Acoustic response of compliable microvessels containing ultrasound contrast agents", Phys. Med. Biol. 51 (2006) 5065-5088.
Qin, S. and Ferrara, K.W.,"The Natural Frequency of Nonliner Oscillation of Ultrasound Contrast Agents in Microvessels", Ultrasound in Med. & Biol., vol. 33, No. 7, pp. 1140-1148, 2007.
Rogers, W. J., Y. L. Hu, D. Coast, D. A. Vido, C. M. Kramer, R. E. Pyeritz and N. Reichek. Age-associated changes in regional aortic pulse wave velocity. J Am Coll Cardiol (2001) 38(4): 1123-9.
Roth, B. J. (2000). Influence of a perfusing bath on the foot of the cardiac action potential. Circulation Research 86, E19-E22.
Sandrin, L., S. Catheline, M. Tanter, X. Hennequin and M. Fink. Time-resolved pulsed elastography with ultrafast ultrasonic imaging. Ultrason Imaging (1999) 21(4): 259-72.
Sarvazyan, A. P., O. V. Rudenko, S. D. Swanson, J. B. Fowlkes and S. Y. Emelianov. Shear wave elasticity imaging: A new ultrasonic technology of medical diagnostics. Ultrasound Med Biol (1998) 24(9): 1419-1435.
Sassaroli, E. and Hynynen, K., "Cavitation Threshold of Microbubbles in Gel Tunnels by Focused Ultrasound", Ultrasound in Med. & Biol., vol. 33, No. 10, pp. 1651-1660, 2007.
Sassaroli, E. and Hynynen, K., "Forced linear oscillations of microbubbles in blood capillaries", J. Acoust. Soc. Am. 115 (6), Jun. 2004.
Sassaroli, E. and Hynynen, K., "Resonance frequency of microbubbles in small blood vessels: a numerical study", Phys. Med. Biol. 50 (2005) 5293-5305.
Silva, G.A. Nanotechnology approaches to crossing the blood-brain barrier and drug delivery to the CNS, BMC Neruosci. 9(Suppl 3): S4, 2008.
Sinkus, R., J. Lorenzen, D. Schrader, M. Lorenzen, M. Dargatz and D. Holz. High-resolution tensor MR elastography for breast tumour detection. Phys Med Biol (2000) 45(6): 1649-1664.
Spach, M. S., Heidlage, J. F., Dolber, P. C., and Barr, R. C. (1998). Extracellular discontinuities in cardiac muscle—Evidence for capillary effects on the action potential foot. Circulation Research 83, 1144-1164.

(56) References Cited

OTHER PUBLICATIONS

Sutherland, G. R. Color Doppler Myocardial Imaging—Potential Applications in Acquired and Congenital Heart-Disease. Acta Paediatr (1995) 84: 40-48.
Tanter, M., J. Bercoff, L. Sandrin and M. Fink. Ultrafast compound imaging for 2-D motion vector estimation: application to transient elastography. IEEE Trans Ultrason Ferroelectr Freq Control (2002) 49(10): 1363-74.
Unger, E.C. et al., "Therapeutic Applications of Lipid-Coated Microbubbles." Advanced Drug Delivery Reviews. May 2004, vol. 56(9), pp. 1291-1314.
Walker, W. F. and G. E. Trahey. A Fundamental Limit on Delay Estimation Using Partially Correlated Speckle Signals. Ieee T Ultrason Ferr (1995) 42(2): 301-308.
Wang, Shougang; Lee, Wei-Ning; Luo, Jianwen; Konofagou, Elisa E.; "A composite imaging technique for high frame-rate and full-view cardiovascular ultrasound and elasticity imaging," IEEE Transactions on Ultrasonics, Ferroelectrics, and Frequency Control 2008 vol. 55(10); pp. 2221-2233.
Wang, Shougang; Lee, Wei-Ning; Luo, Jianwen; Konofagou, Elisa E.; "A composite imaging technique for high frame-rate and full-view cardiovascular ultrasound and elasticity imaging," IEEE International Ultrasonics Symposium, New York, NY, Oct. 28-31, 2007.
Wang, Y. X., M. Halks-Miller, R. Vergona, M. E. Sullivan, R. Fitch, C. Mallari, B. Martin-McNulty, V. da Cunha, A. Freay, G. M. Rubanyi and K. Kauser. Increased aortic stiffness assessed by pulse wave velocity in apolipoprotein E-deficient mice. Am J Physiol Heart Circ Physiol (2000) 278(2): H428-34.
Yuh, EL, et. al. Delivery of Systemic Chemotherapeutic Agent to Tumors by Using Focused Ultrasound: Study in a Murine Model. Radiology, 234(2): 431-437, 2005.
Zerhouni, E. A., D. M. Parish, W. J. Rogers, A. Yang and E. P. Shapiro. Human heart: tagging with MR imaging—a method for noninvasive assessment of myocardial motion. Radiology (1988) 169(1): 59-63.
Zheng, Y.P. et al. "High Resolution ultrasound elastomicroscopy imaging of soft tissues: system development and feasibility; Ultrasound elastomicroscopy." Physics in Medicine and Biology, vol. 49, No. 17, pp. 3925-3938 (Sep. 7, 2004).
U.S. Appl. No. 14/091,010, Jul. 3, 2018 Final Office Action.
U.S. Appl. No. 14/091,010, Jun. 1, 2018 Response to Non-Final Office Action.
U.S. Appl. No. 14/449,820, Jul. 23, 2018 Final Office Action.
U.S. Appl. No. 14/457,023, May 2, 2018 Final Office Action.
U.S. Appl. No. 14/476,543, Mar. 22, 2018 Notice of Allowance.
U.S. Appl. No. 14/476,543, Jun. 22, 2018 Issue Fee Payment.
U.S. Appl. No. 14/682,980, Apr. 26, 2018 Advisory Action.
U.S. Appl. No. 14/695,674, Mar. 15, 2018 Final Office Action.
U.S. Appl. No. 14/949,000, Feb. 28, 2018 Non-Final Office Action.
U.S. Appl. No. 14/449,820, Jul. 8, 2019 Non-Final Office Action.

* cited by examiner

0ms

18ms

36ms
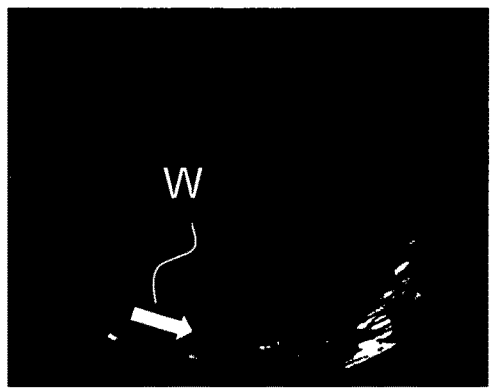 
*FIG. 9(a)*  *FIG. 9(b)*
53ms
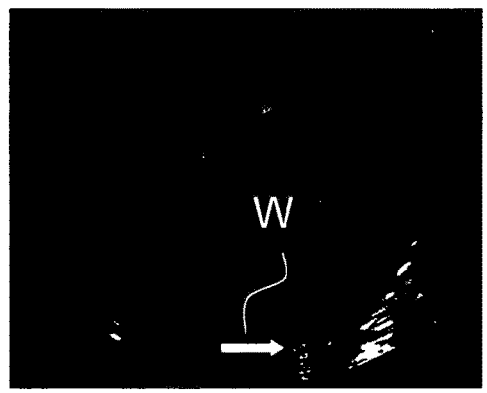 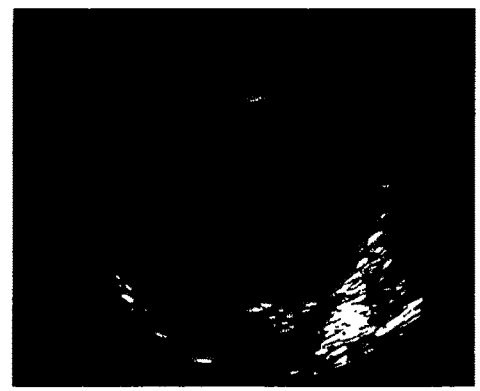
*FIG. 10(a)*  *FIG. 10(b)*

70ms
 
*FIG. 11(a)*     *FIG. 11(b)*

0ms

6ms

18ms

24ms

30ms
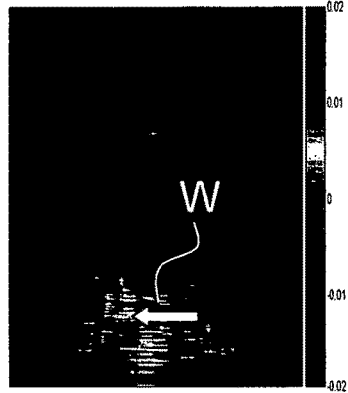 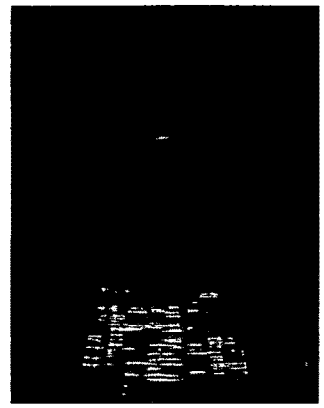
FIG. 16(a)        FIG. 16(b)
36ms
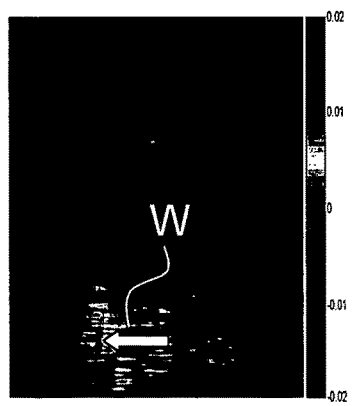 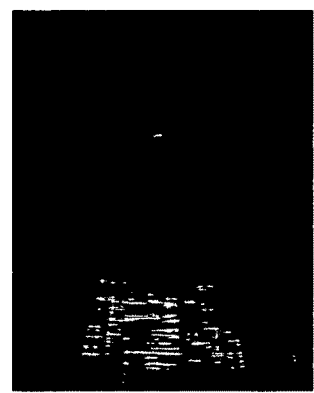
FIG. 17(a)        FIG. 17(b)

42ms
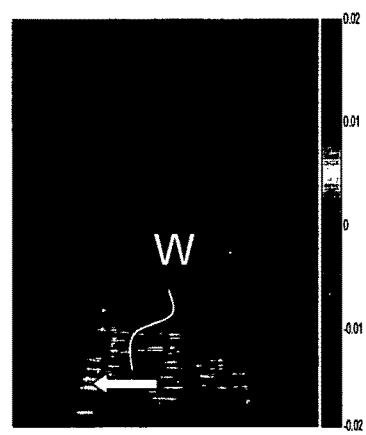 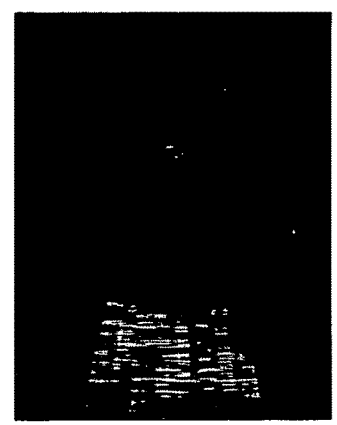
*FIG. 18(a)*    *FIG.18(b)*

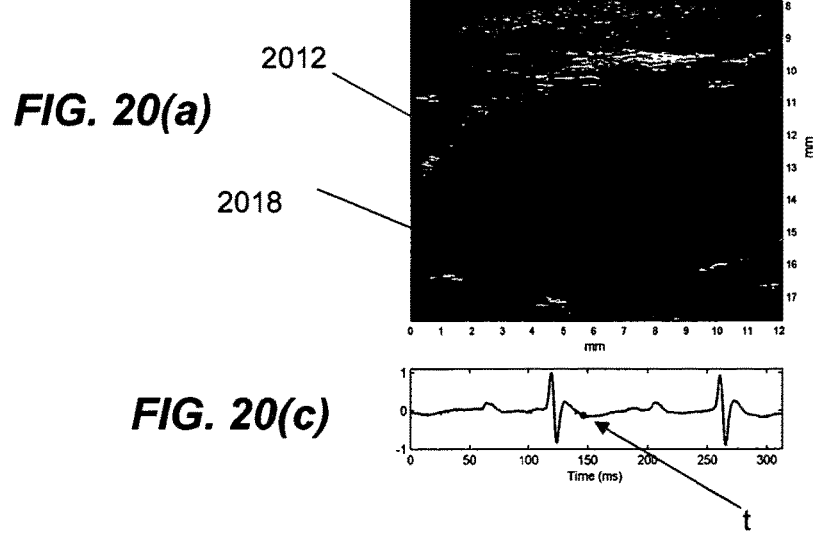
FIG. 20(a)
FIG. 20(c)
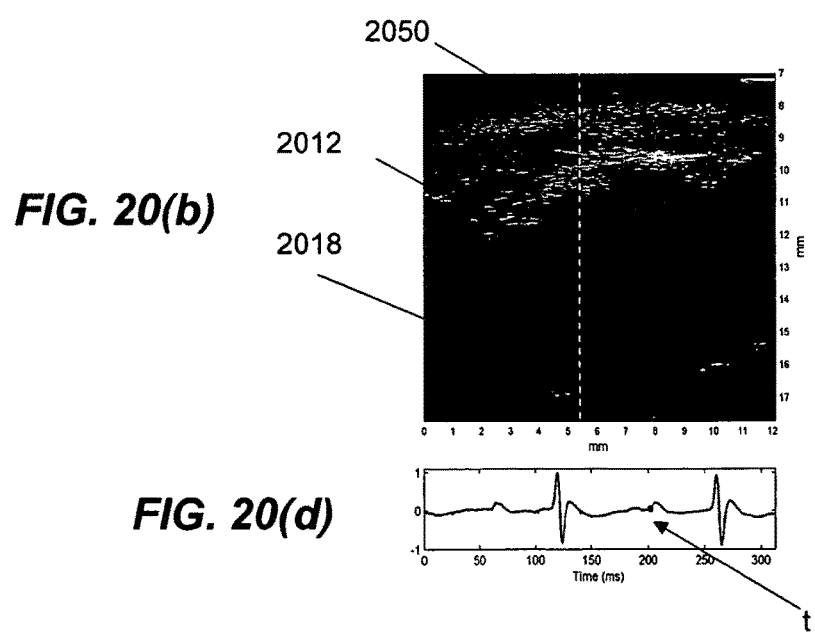
FIG. 20(b)
FIG. 20(d)

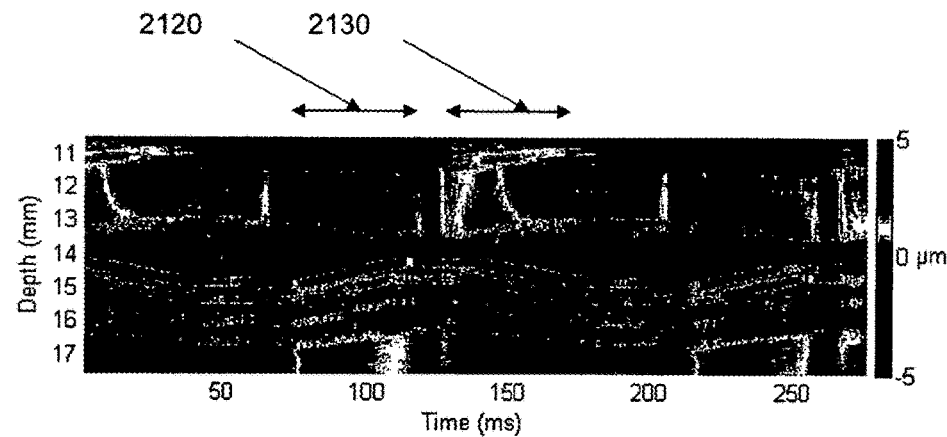
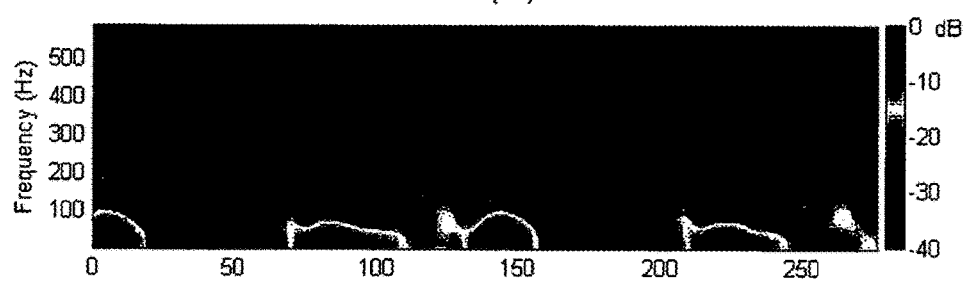
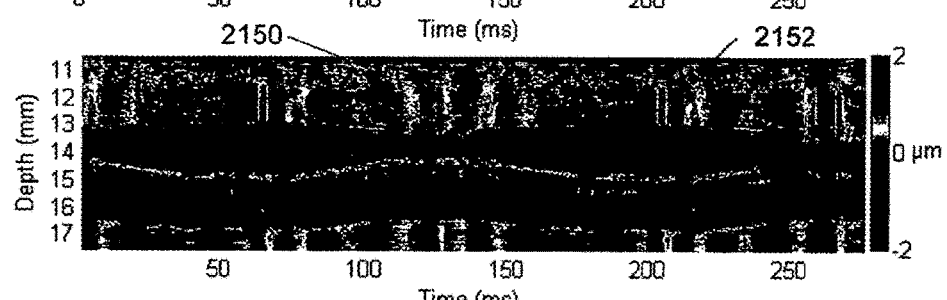
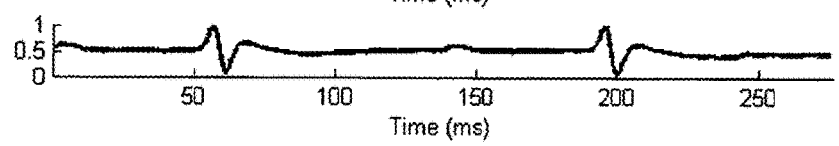
FIG. 21(a)
FIG. 21(b)
FIG. 21(c)
FIG. 21(d)

t=58.2ms t=58.8ms t=59.4ms t=60ms t=60.6ms t=61.2ms t=2.4ms t=5.2ms t=8ms t=10.8ms t=13.6ms t=16.4ms t t t=10.3ms t=11.7ms t=13.1ms t=11ms t=12.4ms t=13.8ms

FIG. 31(a)
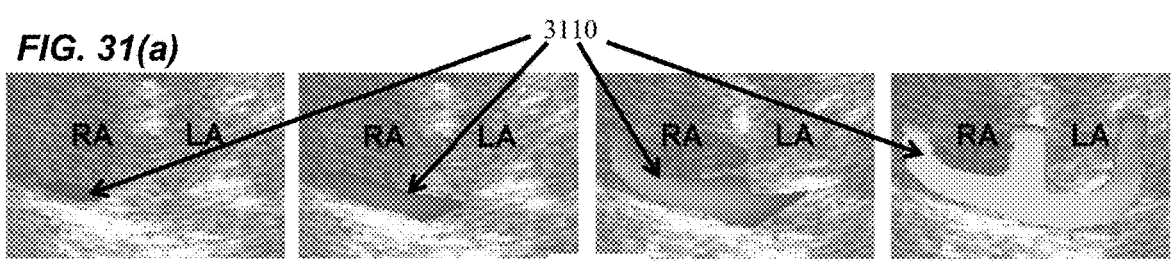
FIG. 31(b)
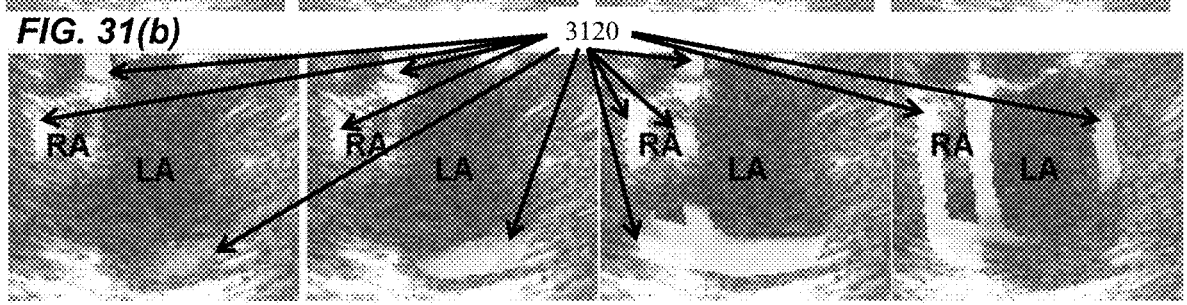
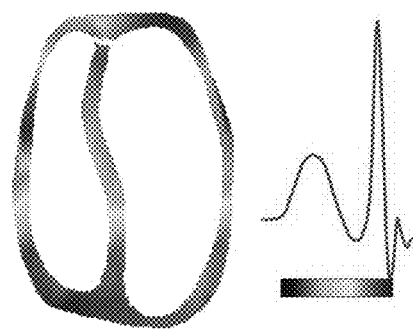
FIG. 31(c)
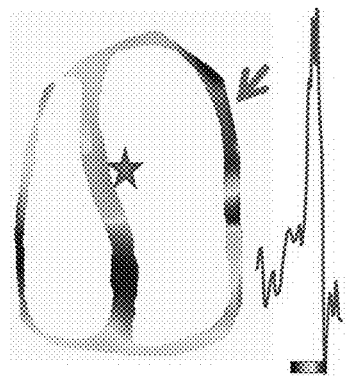
FIG. 31(d)

FIG. 32(a)
Peak cycle length map
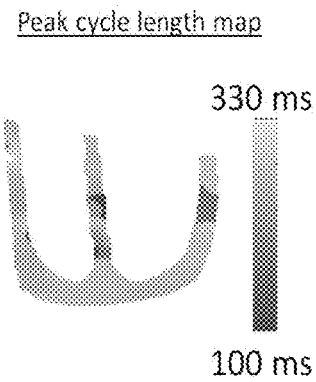
FIG. 32(b)
Cycle length histogram
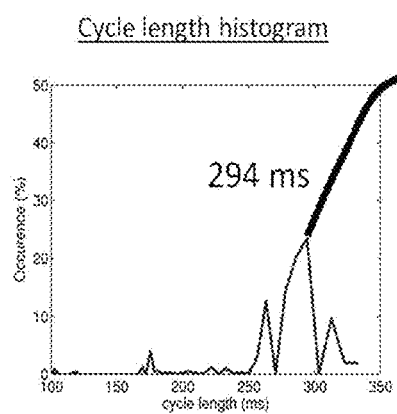
FIG. 32(c)
Phase map
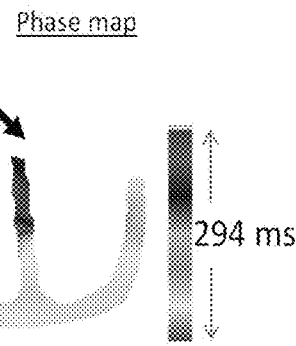
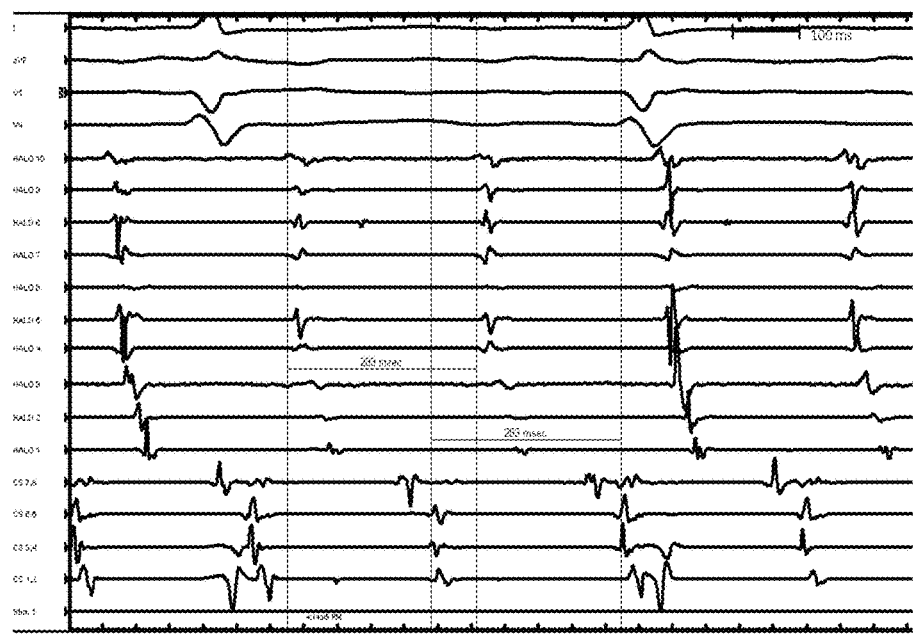
FIG. 32(d)

FIG. 33(a)
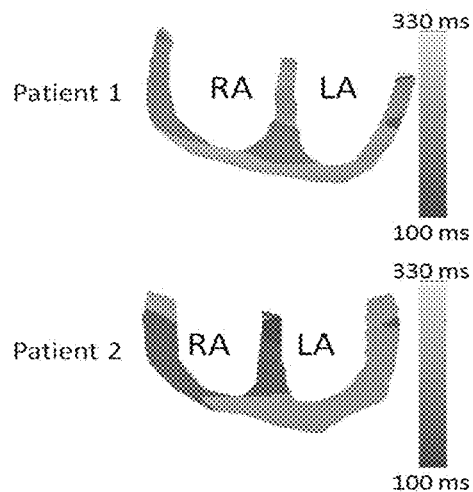
FIG. 33(b)
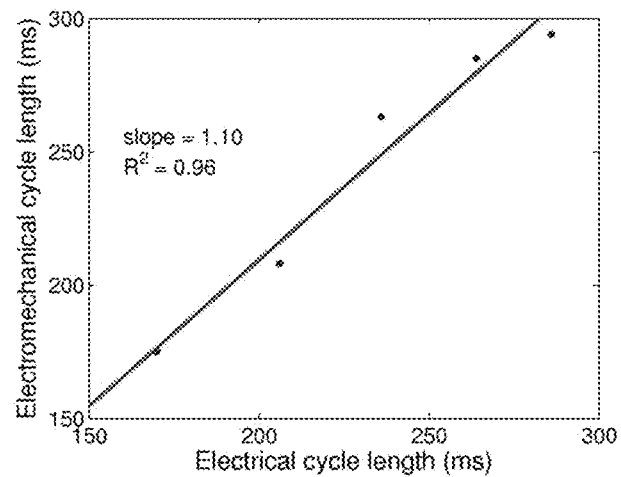
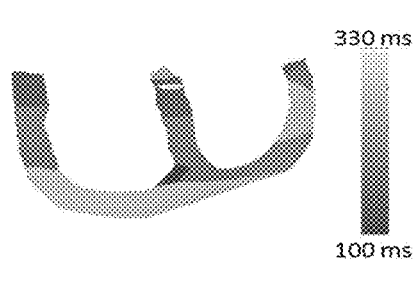
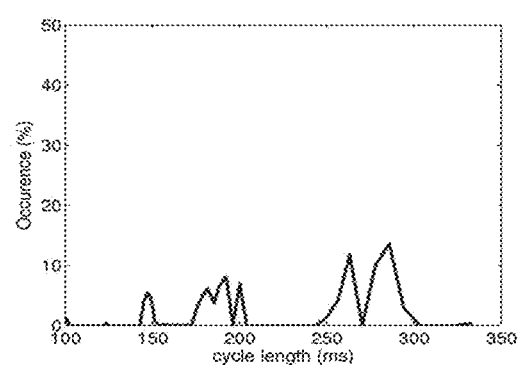
FIG. 33(c)
FIG. 33(d)

SYSTEM AND METHOD FOR ELECTROMECHANICAL ACTIVATION OF ARRHYTHMIAS

CROSS REFERENCE TO RELATED APPLICATIONS

This application is a continuation in part of U.S. patent application Ser. No. 14/449,820, entitled "Systems And Methods For Electromechanical Wave Imaging of Body Structures", filed Aug. 1, 2014, which is a continuation of U.S. patent application Ser. No. 11/433,510, entitled "Systems And Methods For Electromechanical Wave Imaging of Body Structures", filed May 12, 2006, which issued as U.S. Pat. No. 8,858,441 on Oct. 14, 2014, which claims priority to U.S. Provisional Application No. 60/680,081 entitled "Systems And Methods For Electromechanical Wave Imaging of Body Structures", filed on May 12, 2005, each of which is incorporated herein by reference in its entirety and from each of which priority is claimed. This application also claims priority from U.S. Provisional Application No. 62/118,402, filed Feb. 19, 2015, which is incorporated by reference herein in its entirety.

A portion of the disclosure of this patent document contains material which is subject to copyright protection. The copyright owner has no objection to the facsimile reproduction by anyone of any portion of the patent document, as it appears in any patent granted from the present application or in the Patent and Trademark Office file or records available to the public, but otherwise reserves all copyright rights whatsoever.

STATEMENT REGARDING FEDERALLY SPONSORED RESEARCH

This invention was made with government support under grants HL114358, EB006042, and HL096094 awarded by the National Institutes of Health. The Government has certain rights in this invention.

BACKGROUND

This present disclosed subject matter relates to techniques for imaging and detecting the propagation of mechanical waves within a body structure of a patient.

Certain medical conditions, such as diagnosis of myocardial ischemia, can be difficult to establish in their early stages when treatment is most effective. Patients suffering from myocardial ischemia can present to an emergency room or acute care facility with typical cardiac symptoms such as chest pain, described as tightness, pressure, or squeezing, but some patients can have other symptoms such as arm or chin pain, nausea, sweating, or abdominal pain. Certain techniques such as electrocardiogram often provide inconclusive findings regarding ischemia, and sometimes can even be unable to identify situations in which ischemia has progressed to cell damage and myocardial infarction (MI). Other techniques are available for diagnosing infarction relative to its predecessor, ischemia. For example, a blood test to measure the creatine kinase-MB (CK-MB) enzyme level is used for detection of myocardial cell damage. Other serum markers include troponin I, and to a lesser extent, myoglobin. However, the blood levels of certain such compounds can take several hours to rise, so that diagnosis of MI can be delayed. Reliance on blood tests alone can result in a significant loss of time when early aggressive therapy is warranted.

Certain less invasive diagnostic techniques have become available through the observation of mechanical properties of tissue via imaging techniques. Such evaluation of the function of the heart, cardiovascular tissue, or other body structures can be based on the mechanical interpretation of the movement of the these structures, such as, for example, the active contractions and passive relaxation of the myocardium.

Using certain imaging techniques, the evaluation of the heart function can be based on a single mechanical interpretation of myocardial deformation. By use of these techniques, the deformations of the myocardium can be quantified over a complete cardiac cycle in order to provide some information on the myocardial viability.

Certain low frequency mechanical vibrations in the heart are known in human patients. Certain ultrasound techniques can be used to obtain pulsive mechanical vibrations around end-systole and end-diastole in the frequency range of 25 to 100 Hz.

Additionally, atrial arrhythmias are a known and can cause of morbidity and mortality. Certain mechanical factors, such as chamber size and wall tension, can affect the onset and perpetuation of atrial arrhythmia. Certain echocardiographic measurements can also be used to characterize atrial arrhythmias. Yet, systems and techniques to analyze the 2-D spatio-temporal evolution of the local deformations of the atria during e.g., focal tachycardia, flutter, and fibrillation, would be beneficial.

Accordingly, there is a need for a noninvasive imaging modality which provides insight into the source or focus of an arrhythmia.

SUMMARY

The present disclosure provides elasticity imaging techniques to evaluate mechanical wave propagation, and provide an estimation of electrical propagation in a noninvasive manner.

In example embodiments, the disclosed subject matter provides systems and methods for detecting wave propagation within the tissue of a patient in a series of image frames representing movement of such tissue of the body structure. Image data is acquired comprising a series of image frames corresponding to the movement of the tissue. In an exemplary embodiment, the tissue can be the wave propagation in the myocardium. In another exemplary embodiment, the movement of body tissue can be wave propagation in the arteries or the aorta.

A correlation calculation can be performed on the image frames to generate a matrix with the location of correlation maxima representing the relative displacement between the first and second image frames, also referred to as a displacement map. A video can be generated comprising a series of displacement maps. The parameters of movement of the cardiac structure can be detected, such as velocity, attenuation, frequency, etc. The wave can be a shear wave, representative of the electrical wave propagation within the body structure.

According to another aspect of the present disclosure, systems and methods are provided for mapping electromechanical activity during an arrhythmia. Image information of a heart of a subject can be obtained using an imaging device. A strain map of the heart can be generated from the image information. Occurrences of a first electromechanical event of the heart and a second electromechanical event can be determined from the strain map. A spatio-temporal map of atrial and ventricular mechanics of the heart can be generated by tracking the onset of the first and second event for each pixel of a heart wall of the subject identified from the image information. A representative mechanical cycle associated with a contraction of the heart can be identified using the spatio-temporal map.

For example, electromechanical activation mapping can characterize propagation patterns of electromechanical strains during focal and reentrant arrhythmias of the heart.

Additionally, regions in which the mechanical and electrical activities are decoupled can be identified by mapping the electromechanical activity of the heart.

Furthermore, the spatio-temporal map can be generated by obtaining isochrones strongly correlated to electrical isochrones by tracking a propagation front of an end-diastole electromechanical activation of the heart.

In addition, a type of cardiac arrhythmia present in the heart can be determined from the information collected in the ultrasound scan of the heart. Upon identifying that the cardiac arrhythmia present in the heart includes focal rhythms, an onset of ventricular contraction can be determined by identifying a first zero-crossing of an incremental strains occurring after an onset of a P-wave on an electrocardiogram. Upon determining that the cardiac arrhythmia present in the heart is a type of reentrant arrhythmia, a high-resolution Fourier transform can be performed using a generalized Goertzel algorithm to interpolate strain signals in Fourier space for each individual pixel in an atria of the heart.

For example, a peak mechanical cycle length (MCL) map can be generated by selecting a MCL having a highest amplitude within the physiologically-relevant time range for each pixel of the ultrasound scan of the heart, such that the MCL map identifies, for each pixel of the atria, which cycle length is most present in a Fourier spectrum of cycle lengths. The cycle length best representing an atrial contraction of the heart can be determined. A phase corresponding to the determined cycle length can be determined to map a propagation of a mechanical oscillation of the heart at the determined cycle length.

Additionally, the ultrasound scan further can be performed by emitting a circular ultrasonic wave to instruct an ultrasound apparatus to perform a motion estimation sequence. A B-mode acquisition can be performed to capture heart anatomy of the heart. A plurality of beams can be generated to reconstruct frames from the motion estimation sequence using a delay-and-sum algorithm with a reconstructed sampling frequency.

BRIEF DESCRIPTION OF THE DRAWINGS

The patent or application file contains at least one drawing executed in color. Copies of this patent or patent application publication with color drawings will be provided by the U.S. Patent and Trademark Office upon request and payment of the necessary fee.

FIG. 7(a), 7(b), 8(a), 8(b), 9(a), 9(b), 10(a), 10(b), 11(a) and 11(b) are images illustrating the propagation of a wave within a body structure in accordance with an exemplary embodiment of the present disclosure.

FIG. 12(a), 12(b), 13(a), 13(b), 14(a), 14(b), 15(a), 15(b), 16(a), 16(b), 17(a), 17(b), 18(a) and 18(b) are images illustrating the propagation of a wave within a body structure in accordance with another exemplary embodiment of the present disclosure.

FIG. 20(a) is an axial displacement map overlaid to the grayscale B-mode image of the left ventricle during systole in accordance with the present disclosure.

FIG. 20(b) is an axial displacement map overlaid to the grayscale B-mode image of the left ventricle during diastole (relaxation phase) in accordance with the present disclosure.

FIG. 20(c) is an ECG indicating the time of the acquisition during the cardiac cycle of FIG. 20(a) in accordance with the present disclosure.

FIG. 20(d) is an ECG indicating the time of the acquisition during the cardiac cycle of FIG. 20(b) in accordance with the present disclosure.

FIG. 21(a) is a time plot illustrating the temporal variation of the axial displacements estimated on one central RF-line as line plotted on FIG. 20(b) in accordance with the present disclosure.

FIG. 21(b) illustrates the frequency content of the displacement variation in the septum at the depth of 12.5 mm plotted as a function of time in accordance with the present disclosure.

FIG. 21(c) is a time plot illustrating the temporal variation of the axial displacements after bandpass filtering of the plot illustrated in FIG. 21(a) showing the transient and high frequency components in accordance with the present disclosure.

FIG. 21(d) illustrates the ECG signal acquired simultaneously with the data illustrated in FIGS. 21(a)-21(c) in accordance with the present disclosure.

FIGS. 31(a)-31(d) illustrates examples of propagating electromechanical activation in atria of normal subjects and a patient undergoing focal atrial tachycardia in accordance with the present disclosure.

FIGS. 32(a)-32(d) illustrates analysis of reentrant arrhythmias using a single-frequency atrial flutter case using a peak cycle length map, cycle length histogram, a phase map, and electrogram in accordance with the present disclosure.

FIG. 33(a) illustrates peak cycle length maps in two atrial flutter patients in accordance with the present disclosure. FIG. 33(b) illustrates a correlation between mechanical cycle length (MCL) and electrical cycle length in five atrial flutter patients in accordance with the present disclosure. FIG. 33(c) illustrates a peak cycle length map during atrial fibrillation in accordance with the present disclosure. FIG. 33(d) illustrates a histogram depicting spatial fragmentation of peak cycle length during atrial fibrillation in accordance with the present disclosure.

Figure 1:
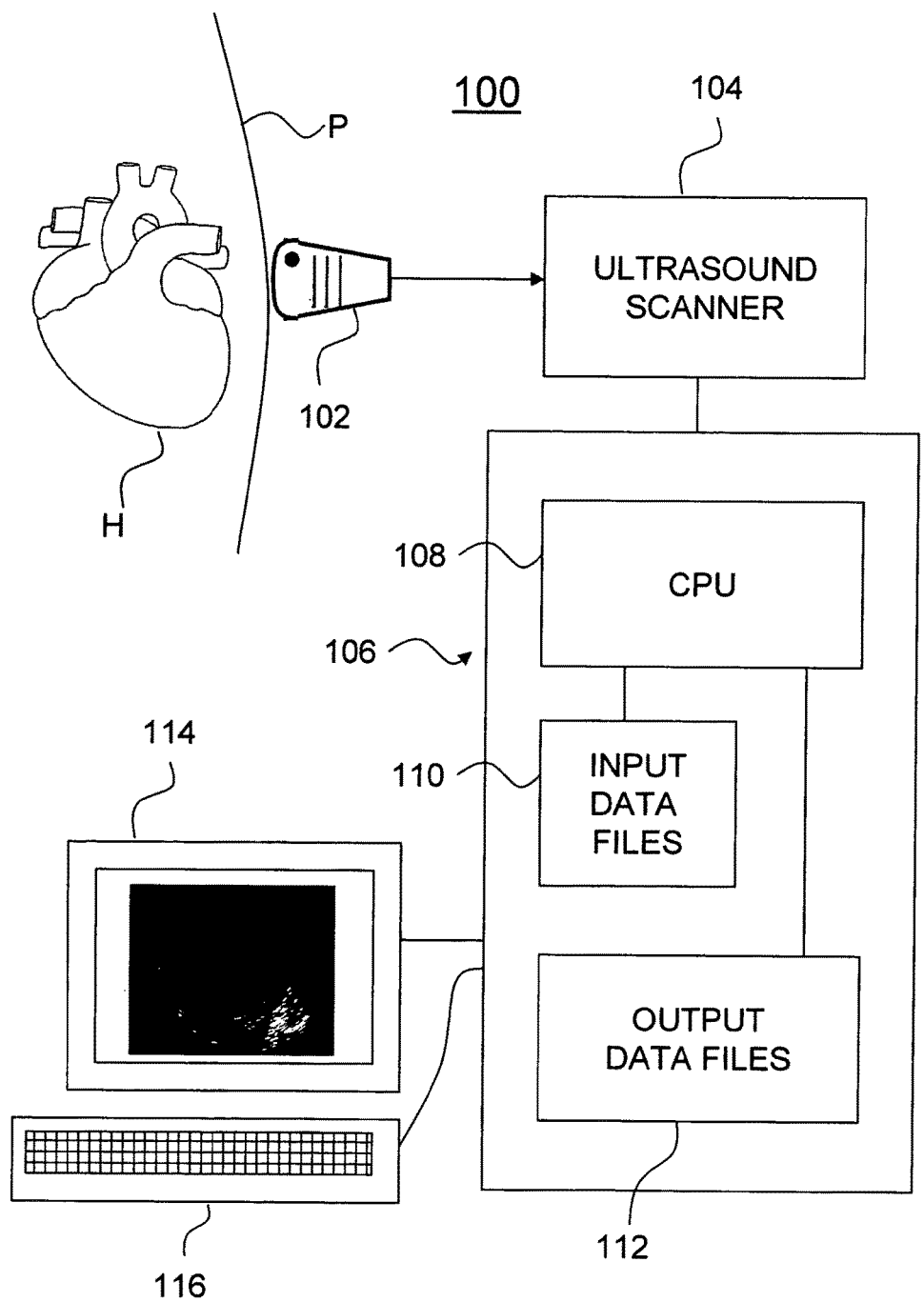
FIG. 1 is a diagram illustrating the system in accordance with the present disclosure.

Throughout the figures, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments.

DETAILED DESCRIPTION

The system and methods described herein can be useful for analyzing data obtained by an image generating device, such as an ultrasound transducer. The systems and methods can also be useful for measuring mechanical properties and estimating the electrical characteristics of a body tissue structure or organ, such as, for example, the myocardium or the aorta.

For example, the disclosed subject matter can be used in connection with imaging and characterizing the propagation of electromechanical waves in the heart. During the cardiac cycle, electrical waves propagate in the myocardium in order to induce its contraction. Contraction of the myocardial fibers results in a strong mechanical wave, which, since it results from the coupling of the electrical excitation and the mechanical properties of the myocardium, is referred to herein as an "electromechanical wave." The speed of this wave is a function of the electrical and mechanical properties of the myocardium, and, according to the present disclosure, can be used to detect changes in these properties to diagnose heart diseases.

An exemplary embodiment of the system is illustrated in FIG. 1 and designated system 100. System 100 can include an image detection device, such as ultrasound probe 102, which is used to create images of the heart H or other organ or structure of the patient P. The image detection device does not induce discernible vibration in the body structure, and merely detects pre-existing motion. The signals detected by the probe 102 can be transferred to an ultrasound scanner 104. The exemplary embodiments described herein are designed to work with conventional ultrasound scanners. For example, commercial portable scanners, such as Terason 2000, high frequency scanners, such as Visualsonics Vevo 770, and routinely used clinical scanners, such as GE System Five or GE Vivid Five or Seven, are useful for image acquisition in accordance with the exemplary embodiments. The raw data produced by the scanner 104 can be transferred to a computer 106 having a CPU 108 for processing the data. In the exemplary embodiment, the computer and CPU would be Dell PC with a 2 GHz processor. It is understood that the computer and CPU can also be integrated with the ultrasound scanner 104. Also useful in the system would be storage such as disk drives, for storing data on input files 110 and for writing output onto output files 112. As will be described herein, input files 110 can include information such as thresholds. Output files 112 can include the displacement maps, videos of myocardium displacements, or computed data, such as electromechanical wave properties. It is understood that a preprogrammed chip can be used to execute the algorithms described herein. Typically, an output device, such as monitor 114, and an input device, such as keyboard 116, are also components of the system.

Figure 2:
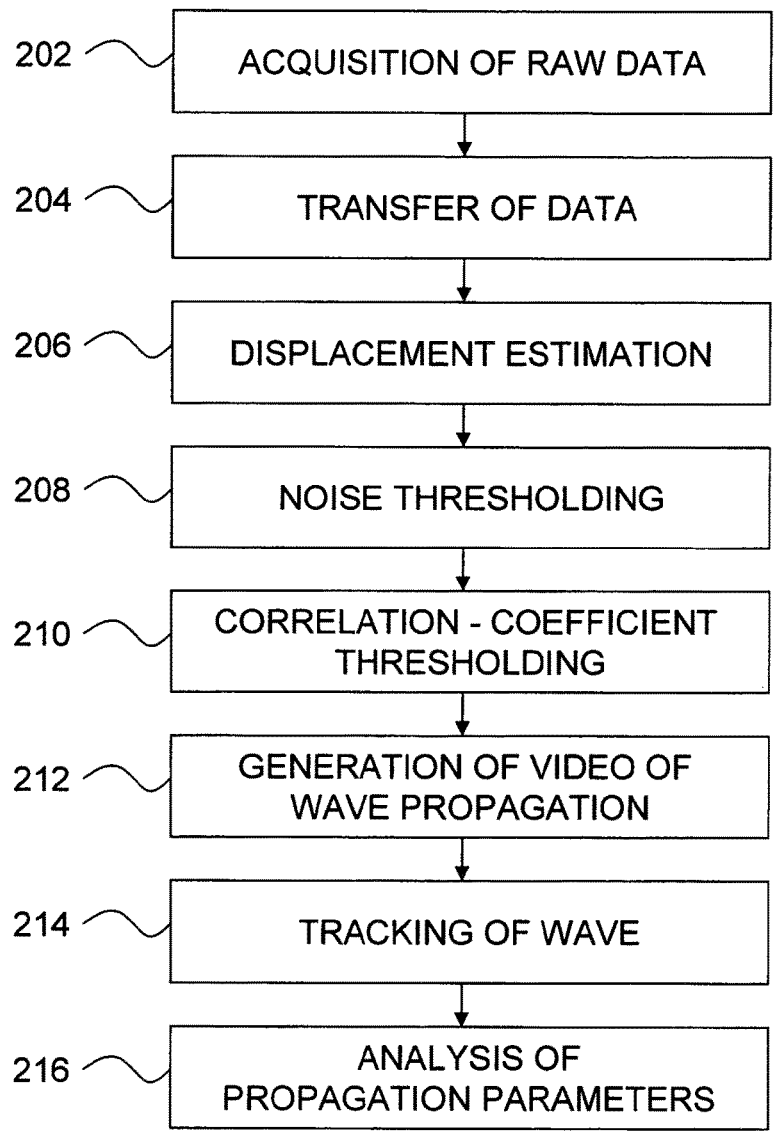
FIG. 2 is a diagram illustrating exemplary stages in a method in accordance with the present disclosure.

In accordance with an exemplary embodiment, the methods described herein are particularly useful for imaging the propagation of electromechanical waves in the heart. A method for detecting the properties of the electromechanical wave are described herein and represented in FIG. 2. In an early stage in the procedure, raw imaging data of the body structure is acquired by image acquisition equipment such as the ultrasound probe 102 and scanner 104. In the exemplary embodiment, a set of N frames of raw ultrasound data of the heart is acquired during a cardiac cycle at high frame rate, e.g., higher than 100 fps, although frame rates of about 56 fps and 170 fps, etc., yield useful results (202). The selected frame rate should be commensurate with the speed of the propagation of the movement, such as the wave, being studied. The electrocardiogram (EKG) can also be recorded. The raw data can be digitized and stored in real-time in the scanner memory.

In a subsequent stage, the data can be transferred to a computer for processing (204). In an exemplary embodiment, the transfer can occur using a protocol such as Ethernet TCP IP. This is optional, as the computer can be integrated with the scanner 104.

At 206, the raw data received from the image acquisition equipment is processed. In the exemplary embodiment, the data processing computes an estimation of the displacement of particular objects in the images, such as the myocardium, between consecutive frames. Typically this processing occurs off-line; however, it is understood that this procedure can occur sequentially subsequent to receiving two consecutive frames. According to the exemplary embodiment, axial displacements (in the direction of the transducer) are computed. Lateral, or elevational, displacements (perpendicular to the transducer) can also be computed using a similar technique, for example, as disclosed in Konofagou E. E. and Ophir, J., (1998), A New Elastographic Method for Estimation and Imaging of Lateral Strains, Corrected Axial Strains and Poison's Ratios in Tissues," *Ultrasound in Medicine and Biology* 24(8), 1183-1199 (1998); Konofagou et al. (1998), Three-dimensional Motion estimation in Elastography, IEEE Proceedings of the Symposium of Ultrasonics, Ferroelectrics and Frequency Control in Sendai, Japan, 1745-1748. Korteweg, D. Uber die Fortpflanzungsgeschwindigkeit des Schalles in elastichen Rohren. Ann. Phys. Chem. (1879) 5: 525-37., the contents of which are incorporated herein.

N−1 displacement 2D maps (also referred to as correlation matrices) are computed through the correlation of two consecutive frames i and i+1 (1<i<N−1). Each frame is represented by a matrix of pixel values. The displacement maps provide an indication of the local axial movements between frames. Estimation of the axial displacements from the two consecutive frames is performed using a speckle tracking algorithm. In this algorithm, the time-shifts in the backscattered signals are determined between two consecutive frames through cross-correlation of small sliding windows over the entire ultrasound image. For each window, the signal of the frame i and the frame i+1 are cross-correlated. The maximum of the correlation coefficient gives an estimation of the time-shift between the two signals. This time-shift can be converted to a spatial displacement by assuming a constant speed of sound for the tissue. This technique can detect displacements on the order of 10 μm. Using small correlation windows of 7.5 mm, the resolution of the displacement maps is in the millimeter range. The cross-correlation algorithm suitable for estimating displacement between consecutive image frames is described in U.S. Provisional Patent Application No. 60/619,247, filed Oct. 15, 2004, which is incorporated by reference herein. In the exemplary embodiment, a Matlab program Multiframe is used to compute the displacement maps for the complete sequence of frames obtained at 202, above. Multiframe calls the Matlab routine FunCalculDispl to compute the displacements for the sequence of frames. FunCalculDispl in turn calls the routine Correlation2D.cpp which is a C program that computes the displacement map between consecutive frames. As discussed above, Correlation2D.cpp uses small sliding windows to find the displacement which maximizes the correlation coefficient for each part of the image. In accordance with other embodiments of the present disclosure, auto-correlation calculations or coherence calculations, as are known in the art, can be performed.

Two optional threshold procedures can be executed in the procedure 200. At 208, a threshold can be applied on the energy of the signal, in order to remove the noise that is below a predetermined signal-to-noise ratio. Low energy ultrasound signals (e.g., noise in the cavity of the heart) can be removed from the displacement map according to this method. At 210, a threshold can be applied on the correlation coefficient to remove erroneous estimates in the displacements. In the exemplary embodiment, the noise threshold and correlation-coefficient threshold can be implemented within the routine Correlation2D.cpp. The levels of the thresholds are determined experimentally and can be stored in an input data file 110 for processing on the CPU 108. Procedures 206, 208 and 210 are illustrated sequentially; however, it is understood that they can occur simultaneously or any other order to appropriately process the data. Moreover, one or more of these procedures can be omitted from the process described herein.

A video of the sequence of N−1 displacement maps can be assembled to create a video of the displacements of the body structure or tissue (212). In the exemplary embodiment, a video of the myocardium displacements is created by this technique.

The video of the displacement map of the myocardium will depict the propagation of the electromechanical wave. Next, an observation and tracking of the wave propagation (214). Although such tracking can be done manually, it can be difficult to discern the wave by visual observation and thus make accurate measurements. Accordingly, wave tracking can be performed by an algorithm, such as TrackPositionWave, a Matlab program which locates the position of the wave front by performing a zero-crossing calculation on consecutive displacement maps.

Figure 3:
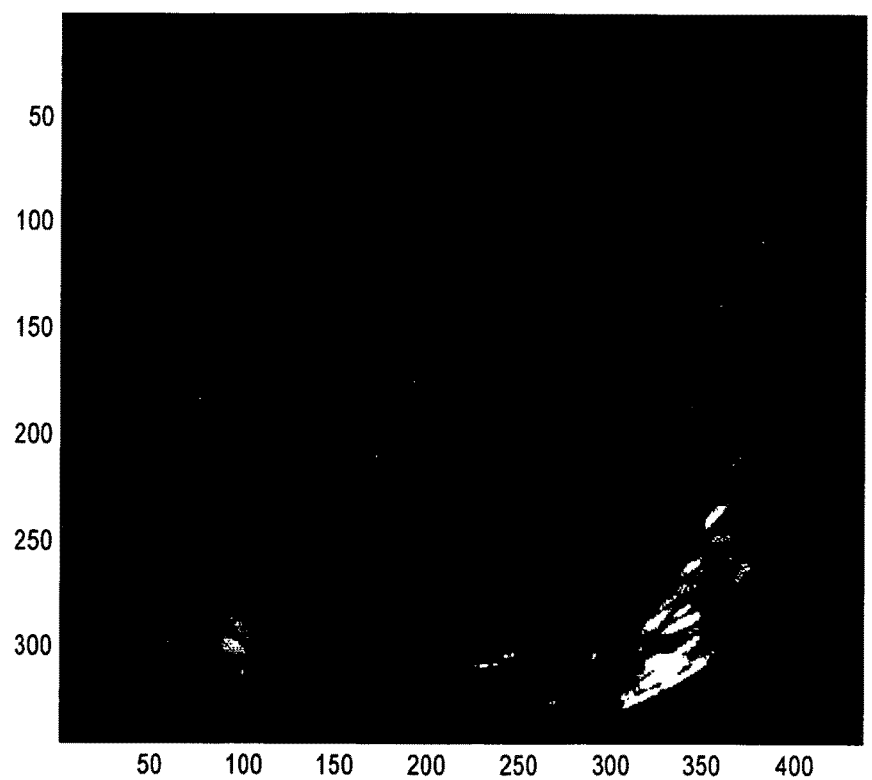
FIG. 3 is a diagram illustrating a technique for measuring movement of structures within an image in accordance with the present disclosure.
Figure 4:
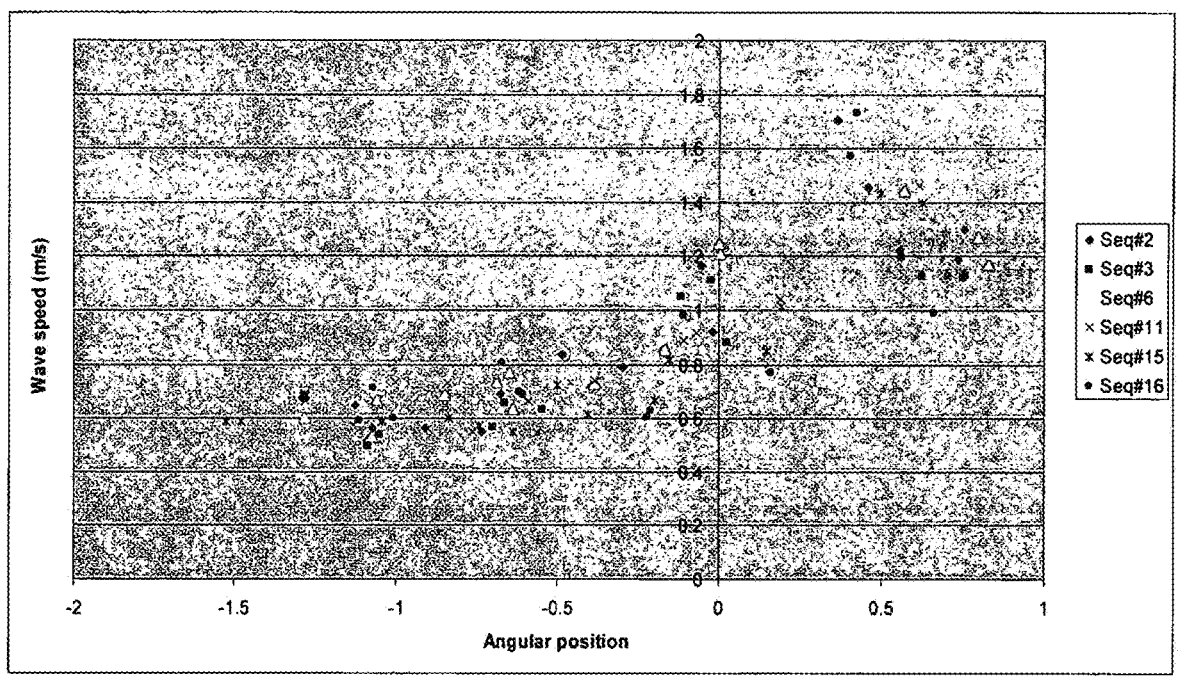
FIG. 4 is a chart representing the velocity of structures within an image in accordance with the present disclosure.

The parameters of the electromechanical wave, e.g., velocity, amplitude, attenuation, frequency, etc., can be analyzed at 216. For example, the velocity of the electromechanical wave can be computed as a function of its position in the myocardium. As illustrated in FIG. 3, the wall of the myocardium is approximated as circular with a radius R, and the origin of the spherical coordinate system was chosen at the center of the cavity. The wavefront of the electromechanical wave was then tracked by its angular coordinate θ. The Matlab function Overlay can be used to compute the transformation of the raw image into polar coordinates. This routine can also display the displacement map superimposed on the ultrasound grayscale data. As an example, the speed of the electromechanical wave is shown on the FIG. 4 as a function of the angular position.

Figures 5, 6:
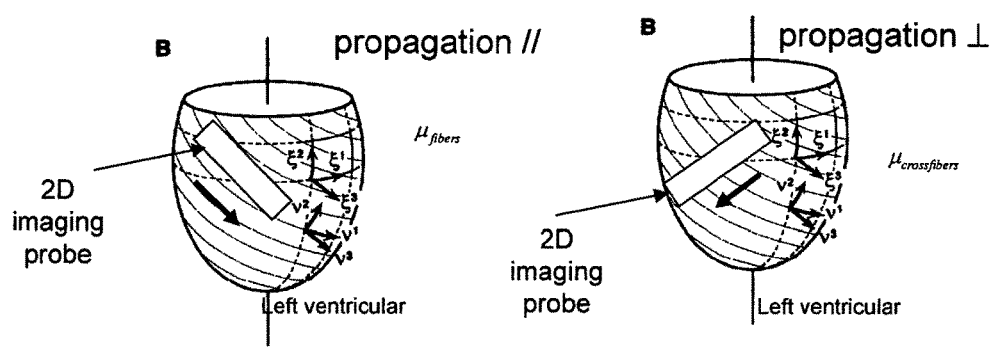
FIG. 5 illustrates a technique of detecting wave propagation in accordance with a further embodiment of the present disclosure.
FIG. 6 illustrates a technique of detecting wave propagation in accordance with yet another embodiment of the present disclosure.
Figure 7A:
Figure 7B:
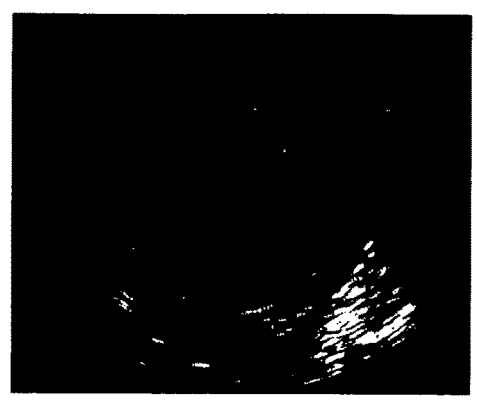
Figure 8A:
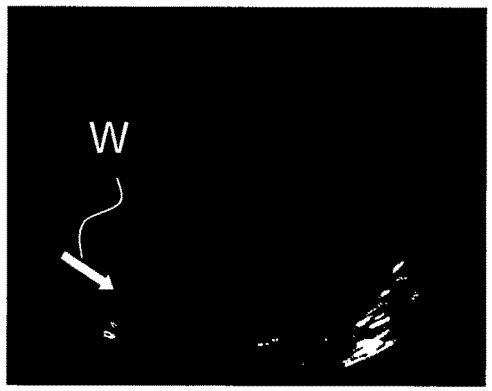
Figure 8B:
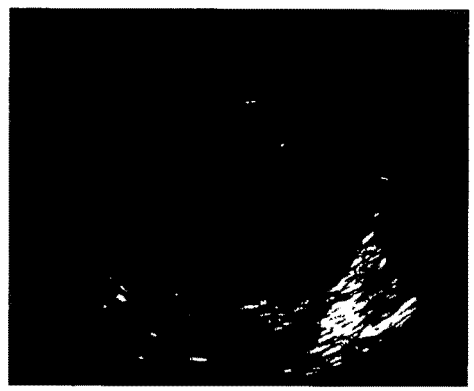
Figure 12A:
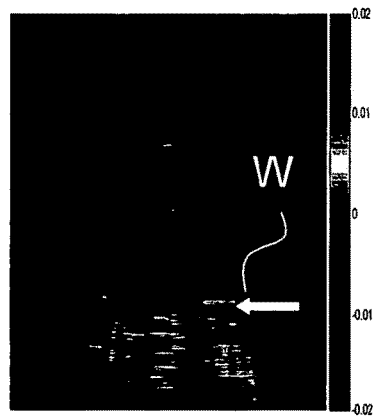
Figure 12B:
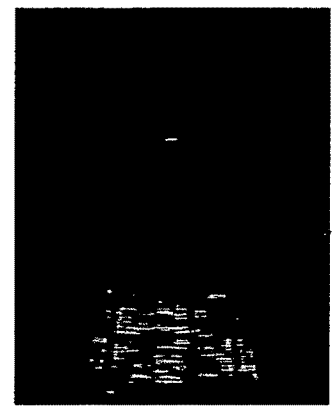
Figure 13A:
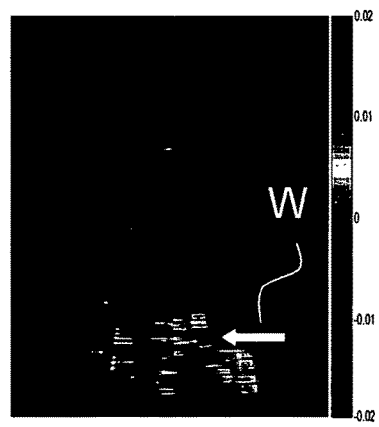
Figure 13B:
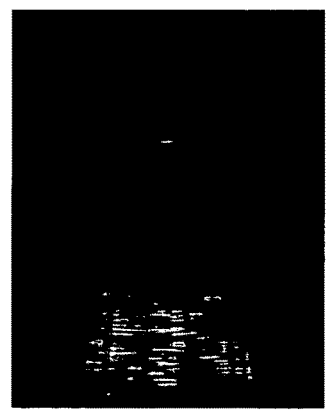
Figure 14A:
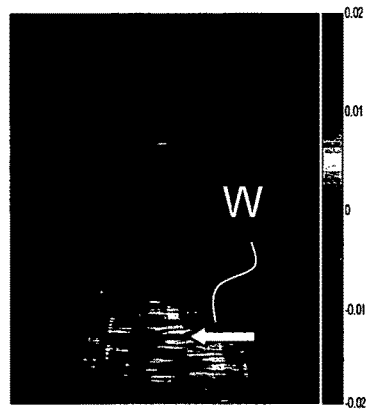
Figure 14B:
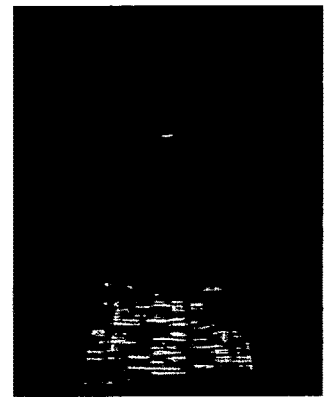
Figure 15A:
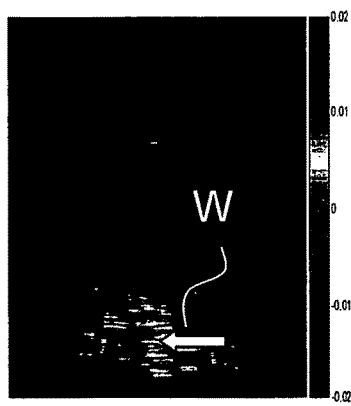
Figure 15B:
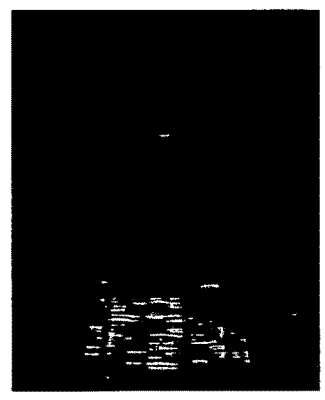

The ultrasound imaging method described herein has the advantage of being completely non-invasive. In an exemplary embodiment, the system described herein can be implemented in real-time on commercial scanners. It has been shown that the electrical conductivity is transversely isotropic with respect to fiber direction, with a longitudinal velocity of about 0.6 m/s and a transverse velocity of about 0.2 m/s (Roth, B. J. (2000), Influence of a perfusing bath on the foot of the cardiac action potential. *Circulation Research* 86, E19-E22; Spach, M. S., Heidlage, J. F., Dolber, P. C., and Barr, R. C. (1998), Extracellular discontinuities in cardiac muscle—Evidence for capillary effects on the action potential foot. *Circulation Research* 83, 1144-1164). The electromechanical wave velocity noted herein was very close to the longitudinal velocity of the mechanical wave. The transverse velocity can be measured by using ultrasound imaging and displacement estimation using a 3D imaging probe or a rotational 2D imaging probe. FIG. 5 illustrates a transducer setup for 2D imaging of the longitudinal waves, and FIG. 6 illustrates a transducer setup for 2D imaging of transverse waves.

The mechanical component of the electromechanical wave is related to the viscoelastic properties of the soft tissue. The elastic properties of the myocardium have been widely investigated. The stiffness of the myocardium has been shown to increase during ischemia and recovers after reperfusion. Thus, early detection of cardiovascular diseases such as ischemia and infarction can be strongly improved through non-invasive characterization of the local myocardial elasticity.

Low frequency shear (mechanical) waves propagate in soft tissue at low velocity (0.5 to 50 m/s). For an isotropic and infinite medium, it has been shown that the velocity of the shear wave is related to the shear modulus $\mu$ and the density $\rho$ by:

$$V_S = \sqrt{\frac{\mu}{\rho}} \tag{1}$$

(Bercoff, J., Tanter, M., and Fink, M. (2004), Supersonic shear imaging: A new technique for soft tissue elasticity mapping. *IEEE Transactions on Ultrasonics Ferroelectrics and Frequency Control* 51, 396-409; Sarvazyan, A. P., O. V. Rudenko, S. D. Swanson, J. B. Fowlkes and S. Y. Emelianov, Shear wave elasticity imaging: A new ultrasonic technology of medical diagnostics. Ultrasound Med Biol (1998) 24(9): 1419-1435.) According to another exemplary embodiment of the disclosed subject matter, a system can be implemented to provide early detection of ischemia through the measure of the velocity of the mechanical wave.

However, the myocardium has also anisotropic mechanical properties and can be considered as a transverse isotropic medium. As a consequence, two shear waves of different velocities can propagate in the myocardium. Fast mechanical (shear) waves propagate in the direction of the fibers, and slow mechanical (shear) waves propagate in the direction perpendicular to the fibers. The measure of the two wave velocities can be achieved by using 3D Ultrasound imaging systems or multiple acquisitions of 2D images with a rotation of the transducer (see FIGS. 5-6). The wave velocities are related to two elastic constants, $\mu_\parallel$ the shear modulus in direction of the fibers and $\mu_\perp$ the cross-fiber shear modulus.

$$V_\parallel = \sqrt{\frac{\mu_\parallel}{\rho}} \tag{2}$$

$$V_\perp = \sqrt{\frac{\mu_\perp}{\rho}} \tag{3}$$

The systems and methods described herein can potentially have different applications in the field of early detection of cardiovascular diseases and cardiac imaging.

For example, the measure of the electrical excitation propagation is of high interest in cardiology for early detection of heart diseases but also for pacing the heart when heartbeat is too slow or irregular. The purpose of an artificial pacemaker is to stimulate the heart when either the heart's natural pacemaker is not fast enough or if there are blocks in the electrical conduction system preventing the propagation of electrical impulses. Thus, in order to implant the artificial pacemaker at the correct location, the electrical propagation must be determined accurately. In vivo imaging of the electrical propagation in the heart can require implanting an electrode matrix (up to 500 electrodes) to measure extracellular potentials at the surface of the heart. This invasive and potentially precarious surgical procedure cannot be performed on human patients for diagnostic purposes. The present disclosure provides a means for determining electrical propagation in the myocardium of a subject, in the context of achieving an effective position of a pacemaker in the subject. Other methods known in the art involve optically-based techniques which also require invasive procedures, such as open-chest surgery.

The present disclosure can be further used to create images and thereby detect myocardial ischemia in a subject either having symptoms (e.g., chest, arm, or chin pain, nausea, shortness of breath, and/or sweating) or a subject subjectively lacking such symptoms (e.g., "silent ischemia"), whereby a finding of increased electromechanical wave velocity (relative to control values) in a region of the myocardium of a subject is consistent with and supportive of a diagnosis of myocardial ischemia in that region. The present disclosure can also be used to diagnose, or assist in surgical intervention in, (i) conduction disturbances, such as re-entry phenomena, or associated with pharmaceutical agents, such as antidepressants or hyperkalemia, (ii) arrhythmias and dysrhythmias (e.g., surgical treatment of ventricular dysrhythmias, diagnosis of low-amplitude atrial fibrillation); and (iii) tissue abnormalities associated with cardiomyopathies or trauma, etc.

Example A

Imaging of Canine Heart

The procedure described hereinabove was performed in an anesthetized open-chested dog. The transducer was placed on the anterior wall of the left ventricle of the heart, to obtain a short axis view. Approximately every two minutes, a sequence of three cardiac cycles was acquired during the experiment, with a frame rate of 56 fps. The 2D displacement maps were estimated using the cross-correlation method (window size: 5 mm, 90% overlap). The axial displacements were processed for the different sequences. On the displacement video, two electromechanical waves were clearly detected, propagating in the posterior wall of the left ventricular, from the septum (left side of the images) to the lateral wall (right side). The propagation of the mechanical wave corresponds to the electrical activity shown on an associated EKG.

The first electromechanical wave is found at the end-diastolic phase of the cardiac cycle (which corresponds to the beginning of the contraction). FIG. 5(a) through 9(a) show five consecutive frames of the propagation of the wave. The location of the electromechanical wavefront is indicated by arrow W in each of FIGS. 7(a)-11(a). The displacements maps are overlaid to the grayscale ultrasound images (see, FIGS. 7(b)-11(b)). Blue displacements are in the direction of the transducer (top of the image), and red displacements are in the opposite direction. As shown in these images, the contraction of the myocardium starts on the left side (septum) and propagates to the right side of the image. In the figures, the blue region appears on the left side of the images (behind the wavefront), and the red region appears on the right side of the image (in front of the wavefront). The maximum displacements shown are 75 μm (dark blue and dark red), and the wave propagates within a few milliseconds. Therefore it is impossible to visually detect this electromechanical wave on the grayscale images. The wave speeds as measured using the techniques described above are represented in FIG. 4. The wave velocity was found to be approximately 0.6 m/s in the posterior wall, which was corroborated by invasive electrophysiological measurements using a matrix of electrodes. Temporary regional ischemia was then induced by coronary artery ligation. The velocity of the electromechanical wave was found to increase up to approximately 1.7 m/s in the ischemic region. Although not entirely understood, this strong increase is believed to be due to an increase of the shear modulus in the ischemic region or a change in the conduction velocity, or both. (A second electromechanical wave has also been detected at the end-systole phase. However, due to its high propagation speed (related to the high contraction of the myocardium), the propagation was not caught with a sufficiently high frame rate. Some evidences of its propagation are detected in the human experiments, described herein.)

Example B

Imaging of Human Heart

The procedure 200 described hereinabove was performed on a young healthy patient. The transducer was placed on the patient's thorax in order to image the heart in the short axis view. A sequence of approximately four cardiac cycles was acquired at a very high frame rate of 170 fps using a Vingmed System Five for RF image acquisition. In order to reach such a high frame rate, only a small part of the heart (the left ventricle) was imaged (80×40 mm). The axial displacements were processed for each frame. On the displacement video, 2 electromechanical waves were clearly seen, propagating in the posterior wall of the left ventricular (not shown). FIGS. 12(a)-18(a), which are consecutive displacement maps superimposed on the grayscale images (FIGS. 12(b)-18(b)), illustrate the propagation of the electromechanical wave at the end-systole phase. The speed was found to be 0.65 m/s in the posterior wall. The location of the electromechanical wavefront is indicated by arrow W in each of FIGS. 12(a)-18(a).

Example C

Imaging of Cardiovascular Tissue in Mice

Animal Preparation

The procedure described hereinabove was performed on anesthetized mice. The mice were anesthetized with tribromoethanol. The hair was removed using potassium thioglycolate and the mouse was placed in the supine position on a heating stage (VisualSonics, Toronto ON, Canada) in order to keep the body temperature steady. ECG signal was obtained from the extremities. The ultrasound probe was placed on the chest or the abdominal wall using degassed ultrasound gel (Aquasonic 100, Parker Laboratories Inc., Fairfield N.J., USA) as a coupling medium.

RF Signal Acquisition

An ultrasound scanner specifically developed for imaging small animals (Vevo 770, Visualsonics, Toronto ON, Canada) was used in this exemplary embodiment. The high frequency ultrasound probe was composed of a single focused transducer working at 30 MHz, with a focal depth of 12.7 mm. The transducer was mechanically rotated and real-time 2D images could be acquired at a frame rate of up to 60 Hz. The field of view was 12×12 mm, the axial resolution was 50 microns, and the lateral resolution was 100 microns.

A digitizer (2 channels, 200 MS/s, 14 bits, CS 14200, Gage Applied Technologies, Lachine QC, Canada) mounted on a PC computer slot was connected to the analog RF-output of the ultrasound scanner. In addition, two TTL outputs were used to trigger the digitizer on the 2D frames. This setup allows the real-time acquisition of more than one thousand 2D RF-data, e.g., images.

In the exemplary embodiment, the ultrasound probe was placed on the chest in the parasternal position to obtain a longitudinal (long-axis) view of the left ventricle of the heart. The probe could also be positioned over the abdomen to obtain a longitudinal view of the abdominal aorta.

Frame Rate Acquisition

In addition to the real-time scanning mode, a high frame rate acquisition mode (EKV) was provided on the scanner in the exemplary embodiment in order to allow detailed visualization of the heart contraction. The equipment can operate as quickly as 8000 frames per minute, although the user can see 1000 frames per minute due to dropped calls. Using this technique, the ultrasound acquisition of each RF-line was triggered on the mouse ECG. The transducer was slowly rotated and for each position of the transducer, ultrasound echo signals were recorded with a pulse repetition frequency (PRF) of 8000 pulses/s during several cardiac cycles. The ECG was simultaneously recorded and thus allowed for the synchronization of the RF-lines based on the R-wave peak, a reliable peak of the ECG during the cardiac cycle. The complete acquisition duration was approximately 5 min.

To compute the tissue motion, RF-signals and ECG signals were digitized during the EKV acquisition and transferred to the computer in real-time. The data were then processed off-line, RF-lines were synchronized using the R-wave peak of the ECG signal, and a complete set of 2D ultrasound RF-data was reconstructed at 8000 fps for one complete cardiac cycle (approximately 150 ms).

Motion Estimation

The motion of the tissue was estimated off-line using a well-known classical speckle tracking algorithm (Bonnefous, O. and P. Pesque. Time domain formulation of pulse-Doppler ultrasound and blood velocity estimation by cross correlation. Ultrason Imaging (1986) 8(2): 73-85.). This technique was based on detecting the small local displacements of the tissue that occur between two consecutive frames. With the current method, only axial displacements (in the direction of the transducer) were computed. In this algorithm, the time-shifts in the backscaterered signals were determined between the two consecutive frames through cross-correlation of small sliding windows over the entire ultrasound image. This technique allowed the detection of very small displacements on the order of 1 μm or less (correlation windows of 150 μm, overlapping 90%). Finally, the movie of the axial displacements was processed at a frame rate up to 8000 frame/s for the entire cardiac cycle. It is understood the lateral displacement can be obtained using the same technique.

Frequency Analysis

The axial displacements were analyzed in the frequency domain as a function of the time. A sliding Blackman window (100 points, 25 ms) as is known in the art, was moved along the displacement variation at a fixed depth, in steps of 2 ms. The windowed signals were zero-padded to 8192 points and their FFT was calculated. The frequency content of the displacements was evaluated graphically by plotting these spectra as a function of time. Based on this frequency analysis, the transient and the slow motions of the tissues were separated using a digital filter. The displacement estimates were temporally filtered using an FIR band-pass filter with cut-frequencies of $f_1=50$ Hz and $f_2=500$ Hz, which allows the removal of the low frequency components but also the high frequency noise.

Wave Velocity

To analyze the propagation of the mechanical waves, the phase velocity of the vibration was determined for an angular frequency $\omega$. The wave was assumed to propagate with a velocity c in a direction r that was arbitrarily determined on the image by the direction of the wall, and a set of measurement points was selected on this direction. The wave number is $k=\omega/c$, and the phase of the wave is $\varphi(r)=kr$ along the direction of propagation. The phase was measured as a function of the propagation distance r, using the Fourier Transform of the temporal displacements at the location r computed at the angular frequency $\omega$. Finally, the derivative of the phase of the wave with respect to distance was estimated using a linear regression fit on the set of measurements points, and the velocity of the wave at the frequency f was calculated:

$$c(f)=2\pi f/(\partial\varphi/\partial r) \quad (4)$$

Modulus Estimation

The theory of elastic wave propagation in soft biological tissue was considered in order to derive the Young's modulus of the tissue. Assuming that the medium is infinite and isotropic, the speed of shear waves propagation could be derived from general equations of the dynamic theory of elasticity. However, it is understood that the propagation of elastic waves in the myocardium can optionally take into account additional characteristics such as the active properties of the muscle fibers, the strong anisotropy of the tissue, and/or the geometry of the ventricles.

For the transverse wave on the artery wall, a simple model of the propagation of a pressure wave in a viscoelastic infinite thin conduit filled with an incompressible fluid is well described by the Moens-Korteweg equation:

$$c = \sqrt{\frac{Eh}{2R\rho}} \quad (5)$$

where c is the velocity of the wave, E is the Young's modulus of the conduit wall, h is the wall thickness, $\rho$ is the density of the fluid and R the radius of the tube. According to this equation, the elasticity of the vessel wall can be derived from the measurement of the pulse wave velocity in the artery.

Results of Example C

In Vivo Cardiac Imaging

Figure 19:
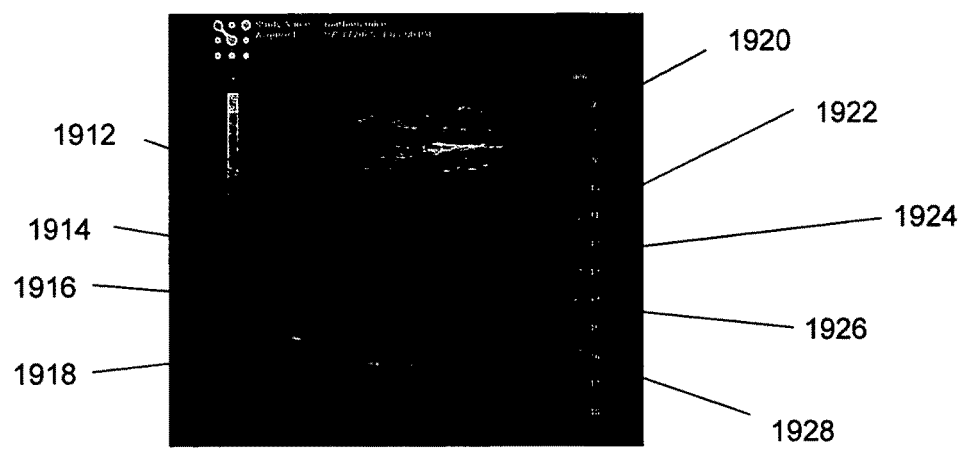
FIG. 19 is an ultrasound image of a mouse left ventricle in a parasternal long-axis view.

FIG. 19 shows a B-mode image 1910 of a typical parasternal long-axis view obtained in a normal mouse. Image 1910 shows the main structures of the left ventricle: the intraventricular septum 1912, the cavity of the left ventricle 1914, the papillary muscle inside the cavity 1916 and the posterior wall 1918 which is visible due to strong reflections at the epicardium-lung interface. Also shown in image 1910 is the right ventricle 1920, aortic valve 1922, aorta 1924, mitral valve 1926, and left atrium 1928. In this embodiment, the duration of the average cardiac cycle was 138 ms. Axial displacements were estimated for the complete set of data. In order to keep the displacements at appropriate magnitudes for the estimation (on the order of 1 μm and to reduce the amount of data, the number of frames was halved, which also reduced the frame rate to 4000 fps.

FIGS. 20(a) and 20(b) show the color-coded axial displacements overlaid onto the grayscale B-mode image for two different phases of the cardiac cycle. During the systolic phase, the contraction of the myocardium is shown by positive displacements (red region) of the posterior wall 2018 and negative displacements of the septum 2012 (blue region) (FIG. 20(a)). In the diastolic phase, the directions of the displacements of the posterior wall 2018 and the septum 2012 (and the colors associated with the direction of movement) are reversed during the relaxation (FIG. 20(b)). It should be noted that even if a large part of the myocardium of the posterior wall is not visible, the motion of the epicardium undergoes similar motion. The time of acquisition of FIG. 20(a) is indicated at point t of FIG. 20(c). The time of acquisition of FIG. 20(b) is indicated at point t of FIG. 20(d).

A temporal analysis of the motion was performed for single RF lines of the image. The axial displacement along one central line of the image (indicated by the white, dotted vertical line 2050 on FIG. 20(b)) is shown as a function of time in FIG. 21(a) with the corresponding ECG signal (FIG. 21(d)). (FIGS. 2(a)-(d) are aligned on a temporal basis.) On this line 2050, the displacements of the septum, the papillary muscle and the posterior wall are shown in a M-mode format over two cardiac cycles. It shows the successive main phases of the cardiac cycle: the contraction of the myocardium (systole) indicated by arrow 2120 initiated at the R-wave peak of the ECG, followed by the relaxation phase (diastole) indicated by arrow 2130. The duration of the active contraction was approximately 50 ms, and that of the relaxation 35 ms. In addition to this slow and large motion, some rapid transient variations of a few ms were observed at the beginning and at the end of the systolic phase, in the septum and the posterior wall.

In order to separate the electromechanical wave from other mechanical waves generated by vibrations resulting from valve functions or blood flow, high-pass filtering was performed. The frequency content of the tissue displacements resulting from vibrations in the septum (at depth of 12.5 mm) was analyzed as a function of time and is shown in FIG. 21(b). During the contraction and the relaxation of the heart, the motion of tissue was found to be in the low frequency range of up to 60 Hz. However, during the transient motion at the end of systole, much larger frequency components were found that ranged between 50 Hz and 500 Hz. The same effect was found for the transient motion at the beginning of systole, but the frequency range was limited between 50 Hz and 250 Hz. Thus, it was possible to almost completely separate the transient part of the displacement by filtering out the low frequency component of the motion. After filtering the displacements using a FIR band-pass filter with cut-off frequencies $f_1=50$ Hz and $f_2=500$ Hz, the two vibrations were clearly visible and are shown on FIG. 21(c) as regions 2150 and 2152. These rapid variations occurred within less than 3 ms around the beginning of systole and end-systole.

End of Systole

Figure 22A:
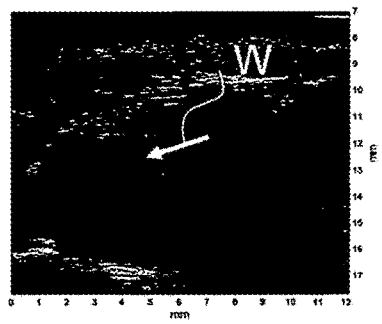
FIGS. 22(a)-22(d) illustrate a sequence of axial displacement maps overlaid to the grayscale B-mode image of the left ventricle around end-systole taken every 0.6 ms showing the propagation of a first mechanical wave front in the septum in accordance with the present disclosure. The arrows indicate the progression of the wave front in the septum.
Figure 22B:
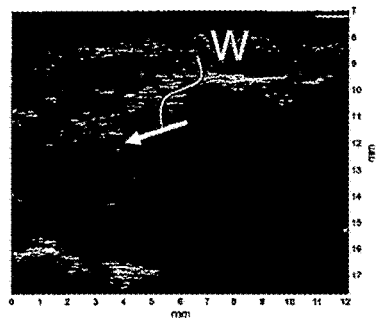
Figure 22G:
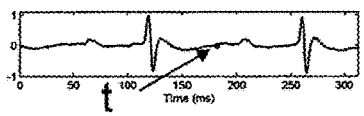
FIGS. 22(g)-22(l) illustrate the ECG signal plotted below each respective image of FIGS. 22(a)-22(f) indicating the time t of the acquisition during the cardiac cycle in accordance with the present disclosure.
Figure 22H:
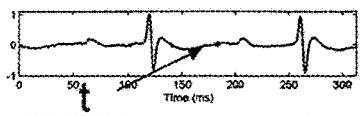
Figure 22C:
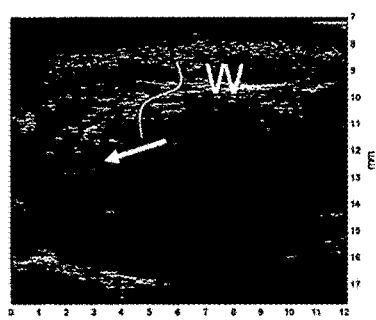
Figure 22D:
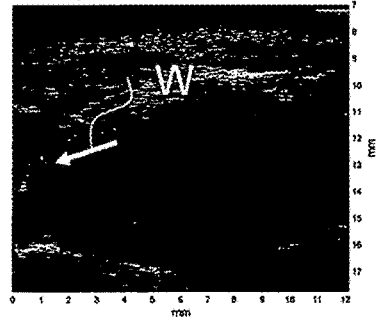
Figure 22I:
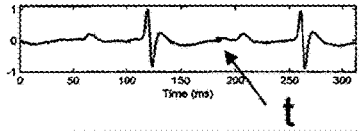
Figure 22J:
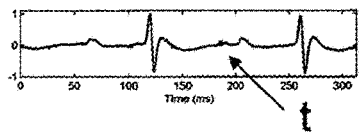
Figure 22E:
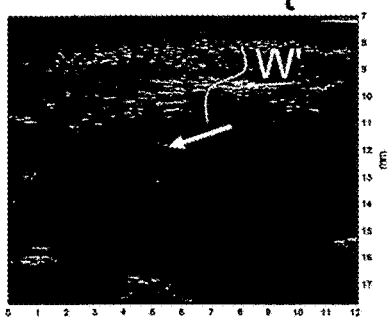
FIGS. 22(e) and 22(f) illustrate a sequence of axial displacement maps overlaid to the grayscale B-mode image of the left ventricle around end-systole taken every 0.6 ms showing the propagation of a second mechanical wave front in the septum in accordance with the present disclosure. The arrows indicate the progression of the wave front in the septum.
Figure 22F:
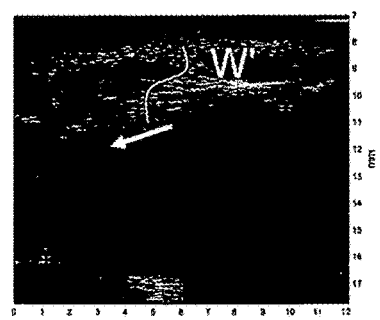
Figure 22K:
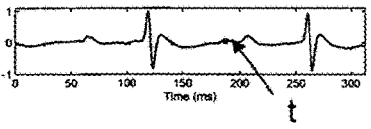
Figure 22L:
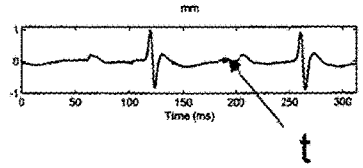

In order to analyze spatially the vibration around end-systole, we considered the data between 52 ms and 70 ms after the peak of the R-wave. FIGS. 22(a)-(d) show a sequence of axial displacements overlaid onto the grayscale B-mode images every 0.6 ms around end-systole. This sequence uncovers a strong mechanical wave W propagating in the longitudinal direction of the ventricle along the myocardium, from the base (right side of the images) to the apex (left side). In other words, as the tissue locally vibrates along the axial direction of the beam (i.e., along the beam axis), a transverse wave propagates along the lateral direction (i.e., in-plane, perpendicular to the beam axis). A second wave W' is shown in FIGS. 22(e)-(f).

Figure 23:
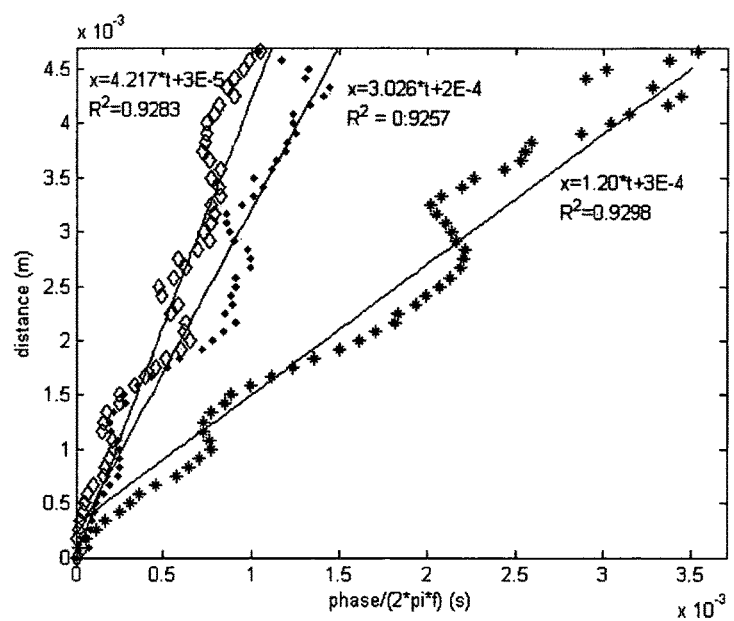
FIG. 23 is a plot illustrating the distance of propagation as a function of the phase of the end-systolic wave at three frequencies in accordance with the present disclosure.
Figure 24A:
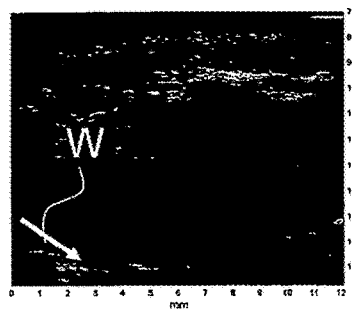
FIGS. 24(a)-24(f) illustrate a sequence of axial displacement maps overlaid to the grayscale B-mode image of the left ventricle around the beginning of systole taken every 2.8 ms, showing the propagation of a strong mechanical wave in the posterior wall in accordance with the present disclosure. The arrows indicate the progression of the wave front in the posterior wall.
Figure 24B:
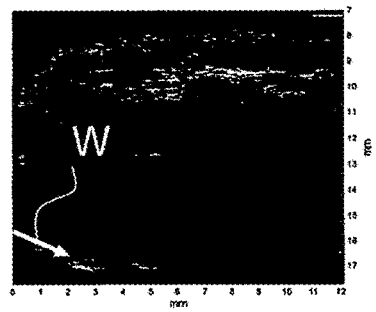
Figure 24G:
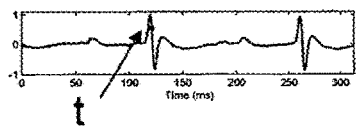
FIGS. 24(g)-24(l) illustrate the ECG signal plotted below each respective image of FIGS. 24(a)-24(f) indicating the time t of the acquisition during the cardiac cycle in accordance with the present disclosure.
Figure 24H:
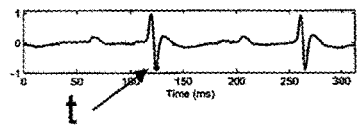
Figure 24C:
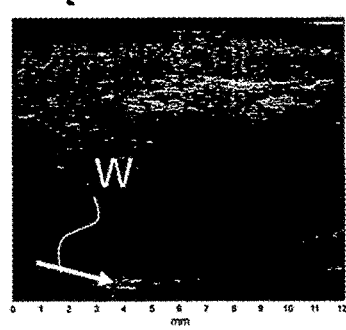
Figure 24D:
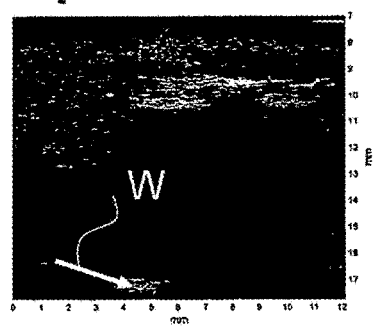
Figure 24I:
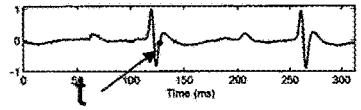
Figure 24J:
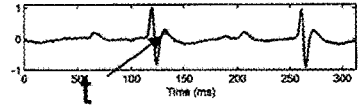
Figure 24E:
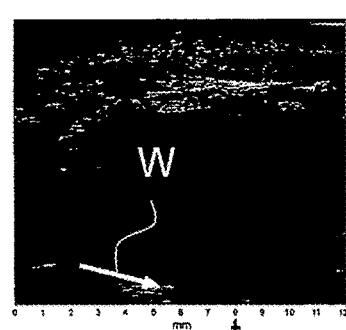
Figure 24F:
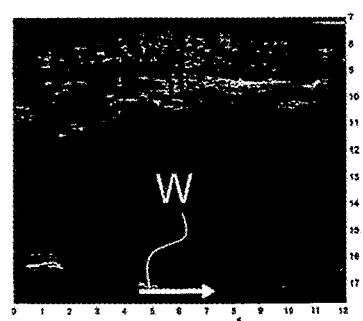
Figure 24K:
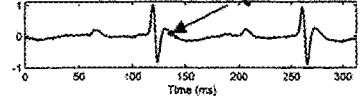
Figure 24L:
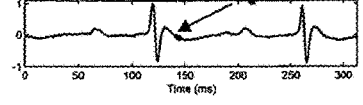

The mechanical wave, i.e., generated by localized vibrations in the muscle (FIG. 21(c)), was visible both in the posterior wall and the septum. Its amplitude was found to be eight times higher in the septum. Only the mechanical wave propagating in the septum is described herein. A set of 60 samples was selected in the septum along the propagation direction (lateral direction of the image), and the phase of the wave was computed at different frequencies. Three frequencies were selected for which the displacement amplitude was large enough to detect, e.g. with respect to noise level: (*) 82 Hz (●) 246 Hz (♦) 410 Hz. The phase velocity of the wave was computed for these frequencies and a large dispersion was found. The distance of propagation was plotted in FIG. 23 as a function of the phase of the wave divided by the angular frequency. The phase velocity was found to be 1.20 m/s at 82 Hz, 3.02 m/s at 246 Hz and 4.21 m/s at 410 Hz.

Beginning of Systole

The same analysis was performed at the beginning of systole. The filtered data were processed between 0 ms and 20 ms from the peak of the R-wave. FIGS. 24(a)-(f) show a sequence of axial displacements overlaid to the grayscale B-mode images every 2.8 ms around the beginning of systole. A strong vibration was found in the septum, but no wave propagation was visible in the image plane. Therefore, a mechanical wave can propagate in the perpendicular direction, but was not being observed with the equipment described herein.

Figure 25:
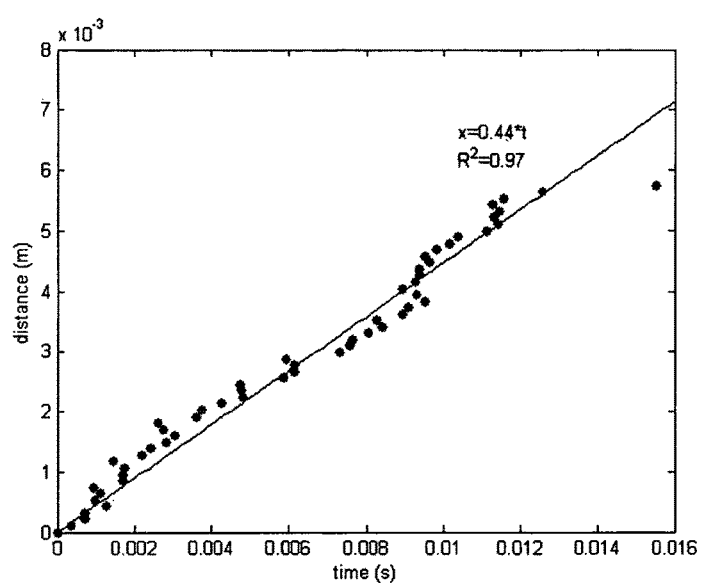
FIG. 25 is a plot illustrating the distance of propagation as a function of the phase of the wave at the frequency of 80 Hz during the beginning of systole transient motion in accordance with the present disclosure.
Figure 26A:
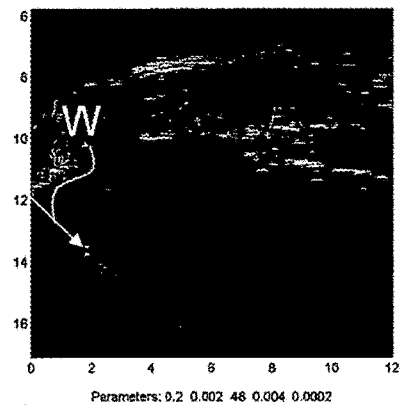
FIGS. 26(a)-26(e) illustrate a sequence of axial displacement maps overlaid to the grayscale image (0.12 ms between successive frames) indicating an electromechanical wave propagating in the posterior wall of the mouse from the apex towards the base during pacing in the right atrium close to the sinoatrial node in accordance with the present disclosure.
Figure 26B:
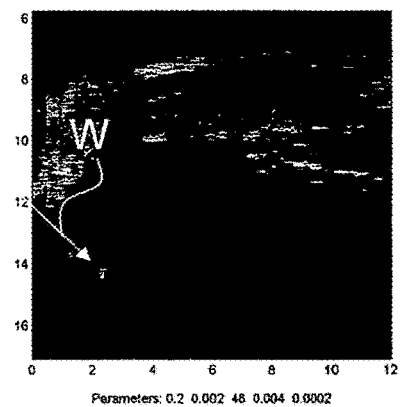
Figure 26F:
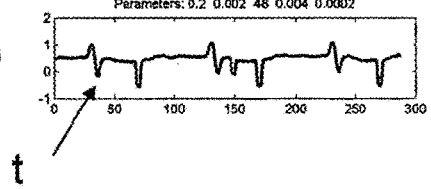
FIGS. 26(f)-26(j) illustrate the ECG signal plotted below each respective image of FIGS. 26(a)-26(e) indicating the time t of the acquisition during the cardiac cycle in accordance with the present disclosure.
Figure 26G:
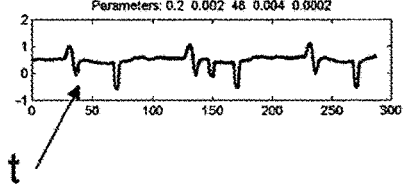
Figure 26C:
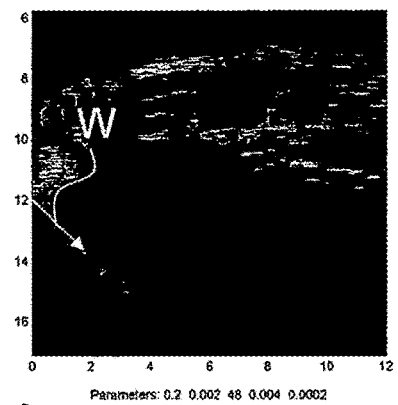
Figure 26H:
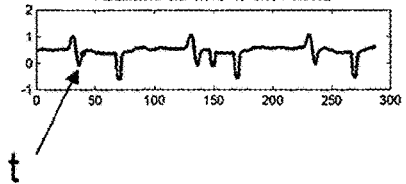
Figure 26D:
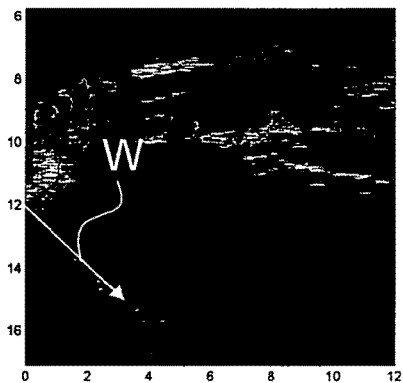
Figure 26I:
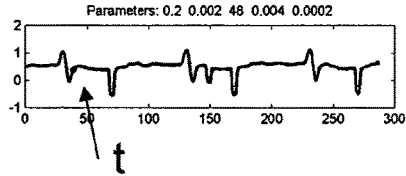
Figure 26E:
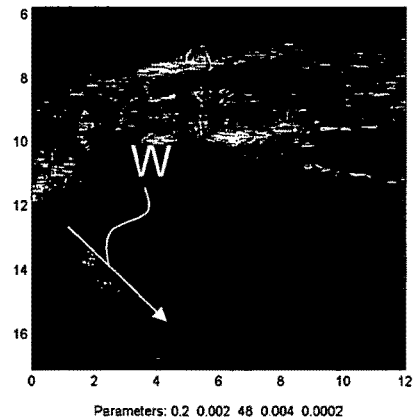
Figure 26J:
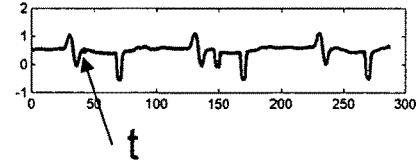
Figure 27A:
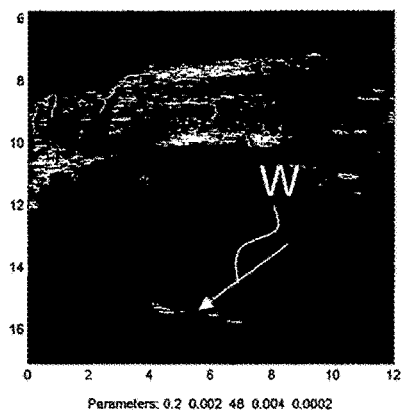
FIGS. 27(a)-27(e) illustrate a sequence of axial displacement maps overlaid to the grayscale image (0.07 ms between successive frames) indicating an electromechanical wave propagating in the posterior wall of the mouse from the base towards the apex during pacing in the right ventricle close to the base in accordance with the present disclosure.
Figure 27B:
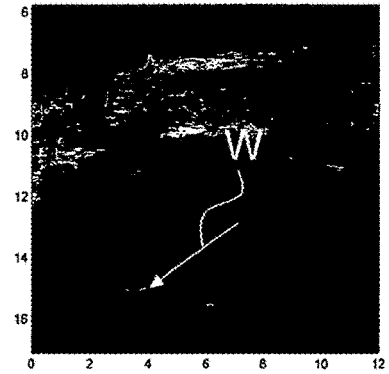
Figure 27F:
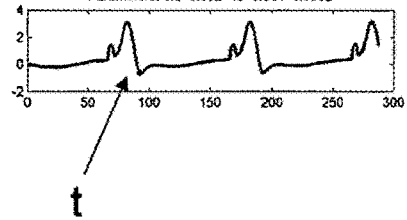
FIGS. 27(f)-27(j) illustrate the ECG signal plotted below each respective image of FIGS. 27(a)-27(e) indicating the time t of the acquisition during the cardiac cycle in accordance with the present disclosure.
Figure 27G:
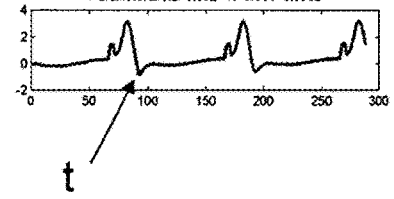
Figure 27C:
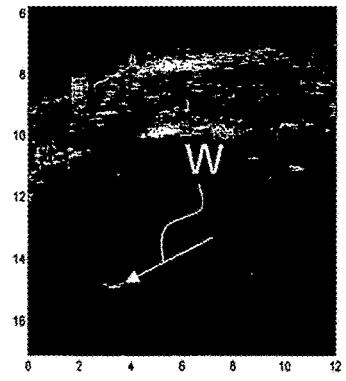
Figure 27H:
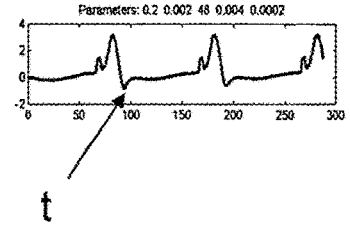
Figure 27D:
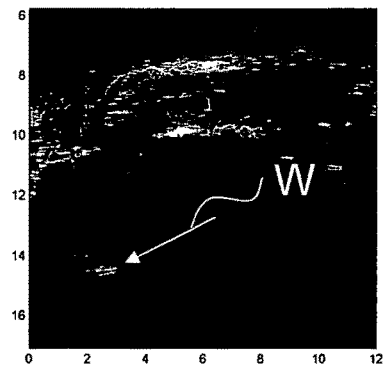
Figure 27I:
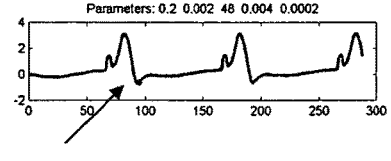
Figure 27E:
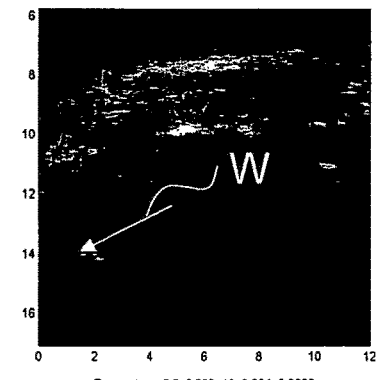
Figure 27J:
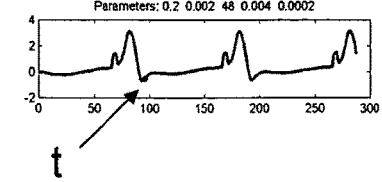
Figure 28A:
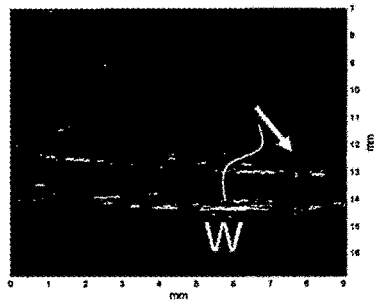
FIGS. 28(a)-28(f) illustrate a sequence of axial displacement maps overlaid to the grayscale B-mode image of the aorta taken every 0.7 ms. Sequence of images showing the propagation of the pulse wave in the aorta. The arrows indicate the progression of the wave front in the aorta
Figure 28G:
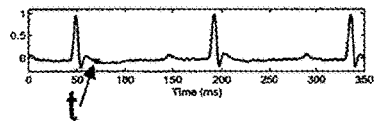
FIGS. 28(g)-28(l) illustrate the ECG signal plotted below each respective image of FIGS. 26(a)-26(f) indicating the time t of the acquisition during the cardiac cycle in accordance with the present disclosure.
Figure 28C:
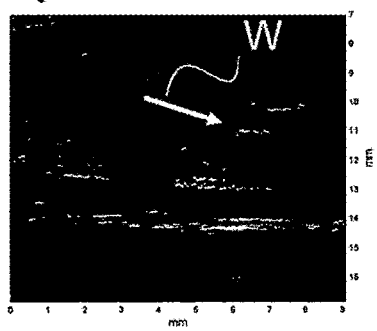
Figure 28I:
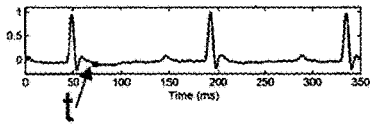
Figure 28E:
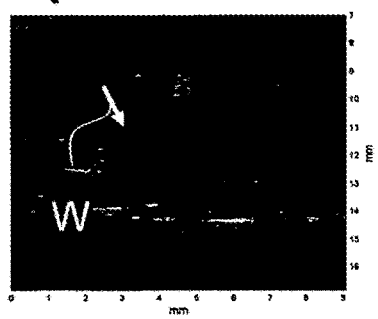
Figure 28K:
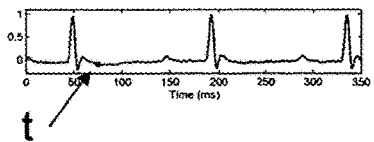
Figure 28B:
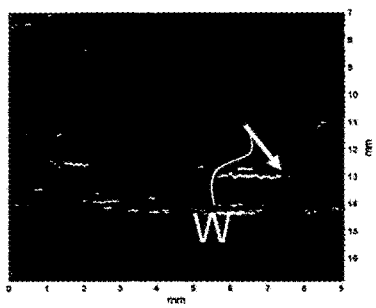
Figure 28H:
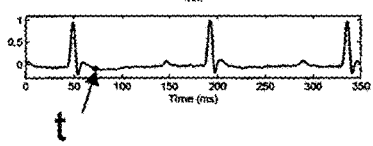
Figure 28D:
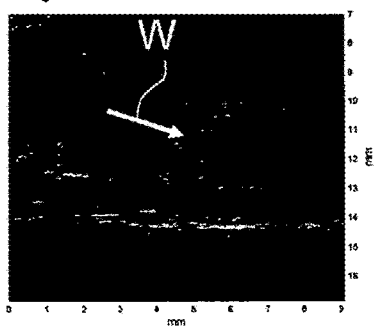
Figure 28J:
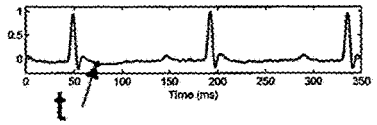
Figure 28F:
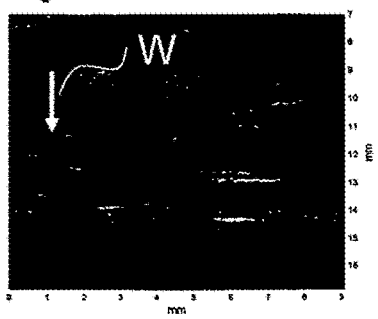
Figure 28L:
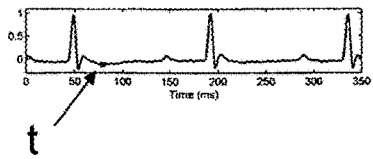

However, the FIG. 24 shows a wave propagating in the posterior wall (see the white arrows W). The displacements were initiated at the apex (left side of the images) and then propagated towards the base (right side). The phase velocity was determined using the method previously described at the frequency of 80 Hz. The distance of propagation was plotted in FIG. 25 as a function of the phase of the wave divided by the angular frequency. The phase velocity of the wave was obtained using a linear regression fit and was estimated to be 0.44 m/s.

Imaging Under Different Electrical Pacing Conditions

In order to determine that the origin and direction of the wave W were electrically induced and driven, mice were also scanned during right-atrial pacing (at 90 ms corresponding to a heart cycle at sinus rhythm of 100 ms period; FIGS. 26(a)-(e)) and right-ventricular pacing (also at 90 ms; FIGS. 27(a)-(e)). Pacing was achieved using catheterization through the right side of the heart, in which the catheter carried nine electrodes that could be separately activated for varying the pacing location. In some of the scans, the catheter C was within the imaging field-of-view and allowed for imaging of the pacing wave during ventricular pacing (FIGS. 26(c) and 27(c)).

The most pronounced wave propagating during atrial pacing was the contraction wave, or wave originating at the isovolumic contraction phase, that propagated along the longitudinal direction of the myocardium initiating radial thickening (or, positive (red) displacement) in its path. At atrial pacing (FIGS. 26(a)-(e)), the contraction wave was very similar to the one during sinus rhythm (FIGS. 24(a)-(f)), starting at the apex right at the QRS peak and then propagating along the posterior wall (generally from right to left in the figure.) Right-ventricular pacing (FIGS. 27(a)-(e)) induced a reverse direction on the contraction wave that now started from the tip of the catheter (close to the base) with two waves propagating from base to apex, one along the septum and one along the posterior wall (generally from left to right in the figure) (FIGS. 27(a)-(e)). Since pacing occurred using the same mouse, same sonographic view and without affecting the function of the valves or the blood flow, the reverse direction of the propagation of the wave is concluded to be induced by the change in the origin of the electrical stimulus; thereby, confirming that the wave measured is electrically induced.

In Vivo Vascular Imaging

A longitudinal view of the abdominal aorta of a mouse was imaged using the high frame rate technique. Axial displacements were calculated, and the movie of the motion was processed at 8000 fps for a complete cardiac cycle. During the cardiac cycle, the displacements of the artery wall were found to be very small except after the beginning of systole. Strong displacements of the wall started 10.3 ms after the R-wave peak of the ECG. FIGS. 28(a)-(f) show a sequence of the axial displacements in color overlaid onto the grayscale B-mode image. A transverse wave W started propagating on the right side of the images (heart side) and then propagated towards the left side in less than 3 ms. This transverse wave was generated from the sudden pressure change of the blood bolus traveling through the vessel, known as the arterial pulsive wave (Nichols, W. and M. F. O'Rourke (1998). Vascular impedance. In McDonald's: blood flow in arteries: theoretical, experimental and clinical principles. E. Arnold. London).

Figure 29:
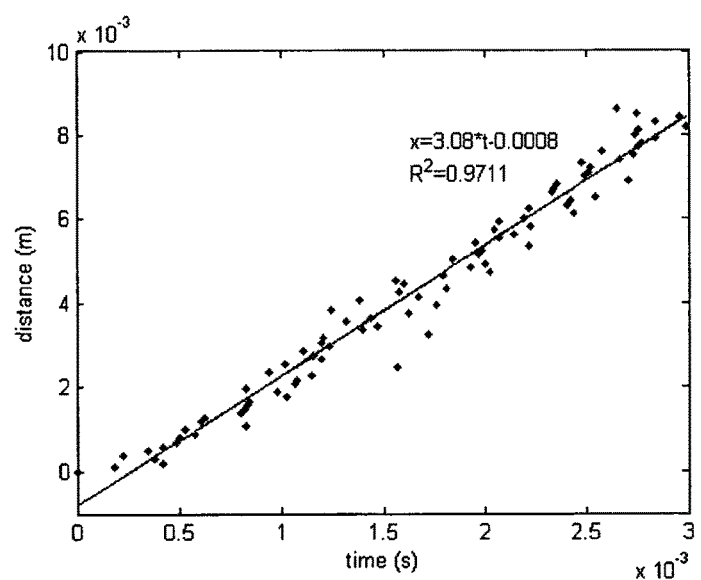
FIG. 29 illustrates the distance of propagation as a function of the phase of pulse wave at the frequency of 80 Hz. The slope of the curve gives the pulse wave velocity in accordance with the present disclosure.

The phase velocity of the pulse wave was computed at the frequency of 200 Hz. The distance of propagation was plotted in FIG. 29 as a function of the phase of the wave divided by the angular frequency, the phase velocity was obtained using a linear regression fit and was found to be 3.08 m/s. The radius of the vessel R=0.47 mm and the wall thickness h=0.12 mm were approximately estimated from the B-mode images, and the blood density was assumed to be 1060 kg/m$^3$ (Cutnell, J. and W. Kenneth (1998). Physics, Fourth Edition. New York). Using these parameters, the Young's modulus of the aorta wall E=78.8 kPa was derived from the Moens-Korteweg equation (Eq. 5), which is what has been typically reported for thoracic aorta moduli in biomechanics literature (Fung, Y. C. (1993). Biomechanics—Mechanical Properties of Living Tissues. New York).

Electromechanical Activation of Arrhythmias

According to another aspect of the disclosed subject matter, systems and techniques are provided for electromechanical activation of arrhythmias, including non-transient electromechanical activation of paroxysmal and periodic arrhythmias in humans in vivo.

Certain treatments of cardiac arrhythmias, such as radiofrequency ablation, can be utilized in clinical practice but can lack a suitable noninvasive imaging modality to provide insight into the source or focus of an arrhythmia. Cardiac deformations can be imaged at high temporal and spatial resolution to elucidate electrical activation sequences in normal and paced human subjects non-invasively. In this manner, such imaging can be used to improve planning and monitoring of ablation-based arrhythmia treatments.

Aspects of the disclosed subject matter include techniques to quantitatively characterize focal and reentrant arrhythmias. For purpose of illustration and not limitation, and as embodied herein, spatio-temporal maps of a full-view of the atrial and ventricular mechanics can be obtained in a single heartbeat. Such maps can illustrate with suitable detail the electromechanical patterns of atrial flutter, fibrillation, and tachycardia. For example and without limitation, during focal arrhythmias, such as premature ventricular complex and focal atrial tachycardia, the electromechanical wave imaging techniques can be utilized to identify the location of the focal zone and the subsequent propagation of cardiac activation. For purpose of illustration and not limitation, exemplary electromechanical wave imaging techniques are described in International Application No. PCT/US13/64377, filed Oct. 10, 2013, which is incorporated by reference herein in its entirety. Additionally or alternatively, and as embodied herein, during reentrant arrhythmias, such as atrial flutter and fibrillation, Fourier analysis of the strains can show correlated mechanical and electrical cycle lengths and propagation patterns.

For purpose of illustration and application of the disclosed subject matter, high frame rate ultrasound imaging of the heart can be used non-invasively and in real time to characterize lesser-known mechanical aspects of atrial and ventricular arrhythmias. Such techniques can also be used to assist treatment planning for intraoperative and longitudinal monitoring of arrhythmias.

Certain imaging systems, such as software-based systems can allow ultra-high frame rates, and thus ultrasound imaging can be used to allow unprecedented temporal resolution. For example, such ultrasound imaging systems can provide a five-fold improvement in the signal-to-noise ratio of cardiac motion and deformation mapping. For example and without limitation, as embodied herein, frame rates up to 2000-5000 frames/s can be achieved by using defocussed transmissions, which can be suitable for depths utilized in transthoracic cardiac applications. According to exemplary embodiments of the disclosed subject matter, ultrasound imaging techniques described herein can be used to map transient strains occurring in response to the electrical activation, (e.g., the electromechanical wave). For example and without limitation, and as embodied herein, such techniques can be used to map transmural activation sequences of normal and abnormal hearts and to locate pacing sites in patients undergoing cardiac resynchronization therapy.

According aspects of the disclosed subject matter, systems and techniques are provided to analyze and characterize the mechanical behavior of the atria. For purpose of illustration and not limitation, and as embodied herein, systems and techniques disclosed herein can be utilized to analyze and characterize the atria during certain types of cardiac arrhythmia, including and not limitation to, premature ventricular complex, focal tachycardia, atrial flutter, and atrial fibrillation. While Electromechanical Wave Imaging (EWI) can be suitable to characterize focal rhythms such as premature ventricular complex and focal tachycardia, EWI can have difficulty describing and/or characterizing reentrant rhythms such as atrial flutter and fibrillation. Accordingly, systems and techniques described herein are provided to characterize electromechanical strains, including and without limitation, during reentrant rhythms based on Fourier analysis. Exemplary embodiments of the disclosed subject matter can include a single acquisition sequence of electromechanical activation mapping that can be used for standard EWI and/or for Fourier analysis of electromechanical strains. Electromechanical activation mapping can characterize electromechanical strain propagation patterns during both focal and reentrant arrhythmias. In this manner, systems and techniques described herein can determine that local deformations of the atria can be closely correlated with their electrical activation. As such, systems and techniques described herein can be used to determine characteristics of cardiac mechanics in arrhythmia, to plan ablation treatments, and to monitor the efficacy of such treatments non-invasively, longitudinally and in real-time.

Example D

Imaging Electromechanical Activity During Arrhythmia

For purpose of illustration and confirmation of the disclosed subject matter, exemplary techniques for imaging electromechanical activation of arrhythmias are described. The systems and techniques described herein can be performed, for purpose of illustration and not limitation, on human subjects. The human subjects can undergo a diagnostic ultrasound scan, and as embodied herein, can occur a few minutes to a few hours prior to electroanatomic mapping and ablation. The cardiac arrhythmias of the patients can be confirmed during electroanatomic mapping and ablation to be, for example and without limitation, one or more of premature ventricular complex (n=1), atrial flutter (n=5), focal atrial tachycardia (n=1), and atrial fibrillation (n=1). Additionally, a normal human subject can be imaged as a control for purpose of comparison.

Additionally, and as embodied herein, strain maps can be generated, for example and without limitation using similar techniques as described herein for single-heartbeat electromechanical wave imaging (EWI). For example and without limitation, as embodied herein, a Verasonics system with a 2.5-MHz probe can be calibrated and customized to adhere to FDA standards, including measurements of mechanical index and of peak spatio-temporal-average intensity. The Verasonics system can be calibrated to have an acoustic power output that is similar to conventional clinical scanners. Such calibration can be performed by measuring the peak pressure and/or intensity (e.g., spatial-peak temporal average intensity, also referred to as Ispta) of the Verasonics system to ensure that its mechanical index (MI) is within FDA guidelines. The ultrasound scan can include two sequences. As embodied herein, in a motion-estimation sequence, a circular ultrasonic wave can be emitted with a virtual focus of 10.2 mm behind the probe at 2000 fps during 2 seconds. Additionally or alternatively, as embodied herein, a standard B-mode acquisition can be performed during 1.5 seconds to depict the heart anatomy. Frames from the motion-estimation sequence can be reconstructed by generating a plurality of beams, for example and as embodied herein 128 beams, in post-processing using a delay-and-sum algorithm with a reconstructed sampling frequency of 20 MHz. As embodied herein, the motion-estimation rate and the motion-sampling rate can be set to 1000 and 2000 fps, respectively. The window for motion-estimation can be 9.2 mm with an overlap of 95.8% (window shift of 0.3 mm), and the kernel strain estimation can be set to 4.9 mm. For purpose of illustration and not limitation, and as embodied herein, the techniques described herein for beamforming, motion-estimation, strain estimation, spatial moving-average of the strains (12 mm by 10 lines), and the automated contour tracking technique can be performed off-line on a graphics processing circuit (embodied herein as a Tesla graphics processing unit) and a Matlab parallel processing toolbox at a computing speed of 2.4 frames/s.

Figures 30A, 30B, 30C:
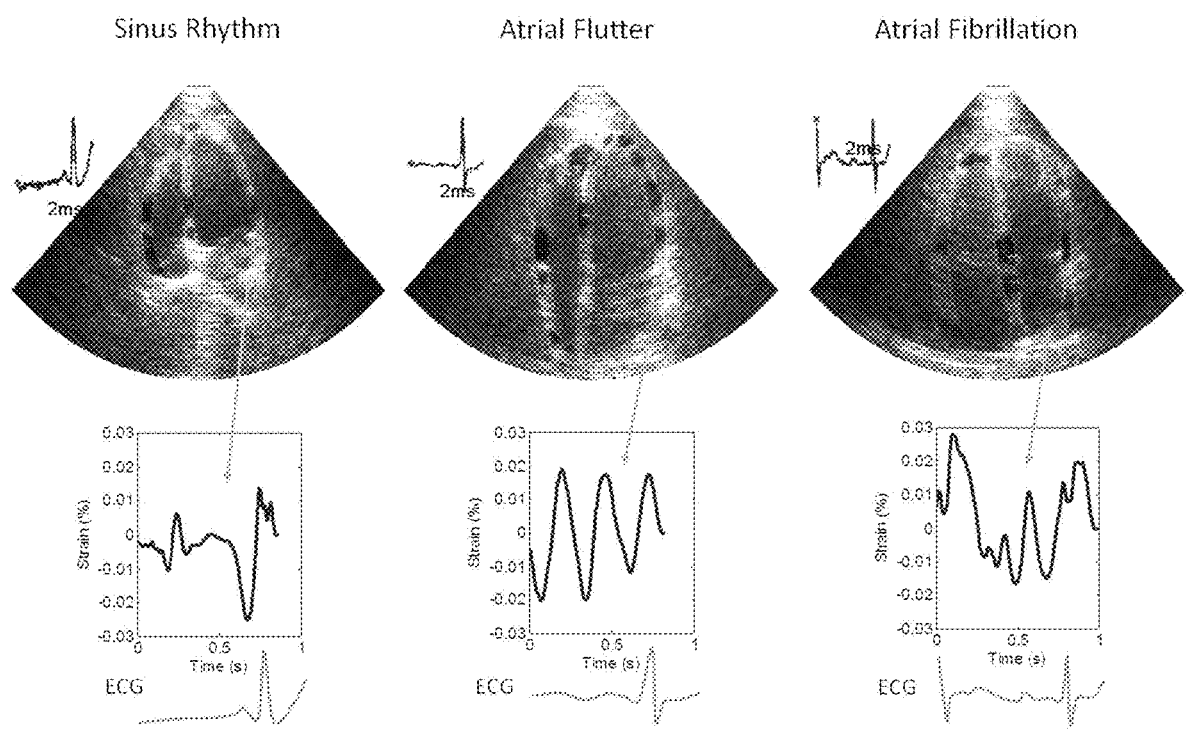
FIGS. 30(a)-30(c) illustrates examples of high temporal resolution strains during different types of arrhythmia in accordance with the present disclosure.

Furthermore, and as embodied herein, focal and reentrant arrhythmias can be analyzed differently for patients with different types of rhythms. For purpose of illustration and not limitation, FIG. 30A illustrates strains mapped in subjects having sinus rhythm. FIG. 30B illustrates strains mapped in subjects having atrial flutter. FIG. 30C illustrates strains mapped in subjects having atrial fibrillation.

As illustrated for example in FIG. 30(a), for subjects with sinus rhythm, the strains in one location, (e.g., one pixel in the left atrium) can present two representative events over time that correspond approximately to the beginning and the end of systole: end-systole, and end-diastole. By tracking the onset (e.g., the first zero-crossing) of these representative events for each pixel of the heart walls, isochrones maps can be generated. Isochrones correlated to electrical isochrones can be obtained, for example and without limitation, by tracking the propagation front of the end-diastole electromechanical activation. As illustrated for example in FIG. 30(b), for atrial flutter patients, a similar location in the left atrium (LA) illustrates that strains can be periodic, which, in some cases, can be represented by a single frequency. Alternatively, as illustrated for example in FIG. 30(c), a plurality of frequencies can be observed in a patient with atrial fibrillation, and as such, analysis based on the Fourier transform might can be utilized. During atrial fibrillation, the strains can be chaotic and no period of zero strains, similar to the one in FIG. 30(a), can be observed.

In addition, and as embodied herein, the onset of contraction can be determined, for example in subjects who have focal rhythms such as sinus rhythm and focal tachycardia, as the first zero-crossing of the incremental strains occurring after the onset of the P-wave on the electrocardiogram (ECG), which can utilize the EWI techniques described herein. Additionally or alternatively, as embodied herein, in atria with reentrant arrhythmia, during flutter and fibrillation, a high-resolution Fourier transform can be performed using a generalized Goertzel algorithm for interpolation in Fourier space on 1.5-second long incremental strains signals for each individual pixel in the atria. For purpose of illustration and comparison with conventional ECG measurements, and without limitation, frequencies can be converted to cycle lengths, hereinafter referred to as mechanical cycle length (MCL). As embodied herein, peak MCL maps can be generated by selecting the MCL with the highest amplitude within the physiologically-relevant 100-330 ms range for each pixel. Additionally or alternatively, and as embodied herein, peak cycle lengths histograms can be constructed and compared to the electrical cycle length measured directly during the electroanatomic mapping and ablation.

Focal Rhythms

FIG. 31 illustrates an EWI ciné-loop and isochrones during focal rhythms. FIG. 31(a) illustrates the atria of a normal subject, with propagation from the right atrium (RA) to the LA. The electromechanical activation regions 3110 can originate in the right atrium and propagate towards the left atrium as illustrated in the exemplary EWI ciné-loop in FIG. 31A.

FIG. 31(b) illustrates an EWI cine-loop depicting the atria of a subject undergoing a focal atrial tachycardia, which can have a focus located high in the left atrium (LA). With reference to FIG. 31(b), as embodied herein, electrical mapping of this patient has not been completed in the LA. The EWI in FIG. 31(b) illustrates electromechanical activation 3120 originating high in the LA and propagating into both atria, and further activation can be detected in the ventricles.

FIGS. 31(c) and 31(d) each illustrate isochrones obtained from a patient with ventricular tachycardia. FIG. 31(c) illustrates an isochrone of the ventricular tachycardia patient during sinus rhythm. FIG. 31(d) illustrates an isochrone of the ventricular tachycardia patient during premature ventricular complex. EWI was performed during sinus rhythm and during pre-ventricular contraction. The EWI isochrones obtained during sinus rhythm, as shown for example in FIG. 31(c), depict propagation from the RA, into the LA and into the ventricles, as previously shown for purpose of illustration and comparison in normal patients. When this patient underwent premature ventricular complex, as illustrated for example in FIG. 31(d), the region that was activated early in the ventricle during sinus rhythm (e.g., from the ventricles to the atria) triggered the entire electromechanical activation sequence. During premature ventricular complex, electromechanical activation can originate from the lateral wall, and can propagate toward the atria and into the atria. Early activation of the septum can indicate a potential recruitment of the Purkinje network.

Reentrant Rhythms

FIG. 32 illustrates the electromechanical behavior of a heart undergoing atrial flutter, including the analysis of reentrant arrhythmias using a single frequency flutter case. FIG. 32(a) illustrates an exemplary peak MCL map, and as depicted, a single MCL is representative. The peak cycle length map of FIG. 32(a) indicates, for each pixel of the atria, which cycle length is representative in the Fourier spectrum. FIG. 32(b) illustrates a histogram of the cycle length which can be used to determine, among all the pixels of the atria, which cycle length represents atrial contraction. With reference to FIG. 32(b), as embodied herein, one peak cycle length of 294 ms can be identified. FIG. 32(c) illustrates a phase map analyzing the phase of the MCL of FIG. 32(b) in Fourier space. As shown for example in FIG. 32(c), as embodied herein, a propagation pattern originates from the right atrium (RA) near the tricuspid valve towards the LA. The phase corresponding to the 294 ms cycle length can be retrieved from the Fourier spectrum and used to map the propagation of the mechanical oscillation at 294 ms. In this manner, the propagation direction can be determined. With reference to FIG. 32(c), as embodied herein, the electromechanical activation propagated from the RA to the LA. FIG. 32(d) illustrates the corresponding intracardiac electrograms obtained a few hours after the imaging procedure. With reference to FIG. 32(d), as embodied herein, the electrical cycle length was 283 ms.

Additionally or alternatively, and as embodied herein, atrial flutter cases can exhibit different patterns. Indeed, certain cases presented with two dominant frequencies can be separated between the left and right atria, whereas certain electrophysiological data can indicate that only one reentrant circuit was present.

FIG. 33(a) illustrates two examples of such atrial flutter cases. FIG. 33(a) illustrates peak MCL maps of two exemplary atrial flutter patients. As shown for example in FIG. 33(a), two representative frequencies can be identified in each patient, with the shorter cycle length located in the RA. A relationship between the MCL and the electrical cycle length can be obtained, for example and as embodied herein, by performing this analysis in multiple patients, and choosing the peak cycle length closest to the electrical cycle length. For purpose of illustration and confirmation of the disclosed subject matter, such an analysis of MCL and electrical cycle length was conducted for five exemplary patients. FIG. 33(b) is a graph illustrating the results of the five exemplary patients. With reference to FIG. 33(b), and as embodied herein, at least one representative MCL was very close to the electrical cycle length. FIG. 33(b) illustrates that electromechanical cycle length and/or MCL can be correlated with the electrical cycle length with a correlation of 0.96 and a slope of 1.1.

FIGS. 33(c) and 33(d) together illustrate results from one exemplary patient undergoing atrial fibrillation. FIG. 33(c) illustrates a peak MCL map depicting multiple clustered dominant frequencies. For purpose of illustration and not limitation, the separation into these dominant frequencies is illustrated by the histogram shown in FIG. 33(d). With reference to FIG. 33(d), the peak cycle length map during atrial fibrillation depicts further spatial fragmentation of the peak cycle length.

Aspects of the present disclosed subject matter illustrate electromechanical activation mapping to identify the site of cardiac rhythm mechanisms during arrhythmia in humans and to characterize such cardiac rhythm mechanisms, which can lead to improved treatments and clinical management. Certain clinical practices utilize minimally invasive techniques to obtain precise maps of the activation of the atria and ventricles. Such techniques can be costly, time-consuming, and carry some degree of risk, and hence can be challenging to provide complete activation maps before and after treatment, as well as during catheter procedures.

Aspects of the present disclosed subject matter illustrate methods for electromechanical activation mapping during reentrant and focal arrhythmias. For purpose of illustration and not limitation, and as embodied herein, exemplary techniques are provided for imaging spatiotemporal mechanics of arrhythmias with high accuracy and spatial and temporal resolutions in a full field of view in humans. These exemplary techniques can provide for characterization of an electromechanical propagation pattern and/or representative mechanical cycle lengths, which can correspond with their electrophysiological equivalents.

For purpose of illustration and not limitation, and as embodied herein, focal rhythms can behave similarly to paced rhythms. For example and without limitation, focal rhythms can have a single source of electromechanical activation located in the vicinity of the earliest electrical activation. As embodied herein, EWI can be used to characterize the propagation of electromechanical activation, which can propagate from an atria's sinus node and from the bundle branch and which can terminate in the ventricles during ventricular pacing. Electromechanical activation propagation patterns similar to pacing can occur in a patient during premature ventricular complexes. The electromechanical activation sequence of the same patient during sinus rhythm can be similar to that of normal subjects. For example, and as embodied herein, in a patient with atrial tachycardia, the electromechanical activation propagation pattern can indicate a source located near the roof of the LA, in accordance with electrical mapping. As such, an exemplary application of non-invasive, ultrasound-based, electromechanical activation mapping is provided, which can be performed during or prior to invasive procedures. For purpose of illustration and not limitation, prior knowledge of an electromechanical source located in the LA can allow for clinical preparation. For example, and as embodied herein, such prior knowledge can be used to determine whether transseptal access would be obtained during treatment and to perform risk-benefit analysis to determine the best course of treatment (e.g., pharmacological vs. ablation treatment).

Additionally, and as embodied herein, the electromechanical activation maps can be correlated with their electrical counterpart, at least in part of the atrial tissue, during atrial flutter. For example, and as embodied herein, a single representative frequency can be identified, and the phase of that frequency can indicate a propagation direction from the cavotricuspid isthmus region to the RA and LA, which can occur during typical atrial flutters. Additionally or alternatively, and as embodied herein, other behaviors can be identified in the atria, including and without limitation, one part of the atria that contracts with the same frequency as the electrical activation and another region that does not contract with the same frequency. As such, mapping the mechanics of the heart can identify regions of the heart in which the mechanical and electrical activities appear to be decoupled. Further spatial fragmentation of the periodicity of the mechanics of the atria can be observed during fibrillation. Such techniques can determine characteristics of the atrial mechanics during arrhythmia, including in the progression from flutter to fibrillation and vice versa.

For purpose of illustration and not limitation, deformation of the atria caused by the onset of ventricular contraction and relaxation can affect certain aspects of the techniques described herein. For example, and as embodied herein, such a deformation can affect frequency analyses based on multiple activation cycles, which can be due at least in part to the relatively short acquisition time of these processes. Filtering and the development of longer acquisition sequences can inhibit or prevent such atrial deformation.

Certain non-invasive electrical mapping techniques can be utilized to examine the epicardium, and can assume an immobilized heart function. A mechanical assessment of the atria can be utilized, for example, by electrophysiologists or interventional cardiologists to achieve the advantages described herein. According to certain clinical practices, echocardiograms can be performed on arrhythmia patients. Other non-invasive electrical mapping techniques can utilize on time-consuming and costly high resolution CT or MRI scans. The electromechanical activation mapping systems and techniques described herein can be obtained separately from, or in conjunction with, echocardiograms.

As embodied herein, mapping the electromechanical activity during arrhythmias non-invasively with real-time feedback can be used determine characteristics of atrial mechanics in the evolution and perpetuation of arrhythmias. Furthermore, and as embodied herein, such a mapping can be used to predict the origin site of arrhythmias and the mechanism and monitoring of intervention outcomes.

It will be understood that the foregoing is only illustrative of the principles of the present disclosure, and that various modifications can be made by those skilled in the art without departing from the scope and spirit of the present disclosure.

What is claimed is:

1. A method for mapping electromechanical activity during an arrhythmia, comprising:
    obtaining image information of a heart of a subject using an imaging device;
    generating a strain map of the heart from the image information;
    determining from the strain map occurrences of a first electromechanical event of the heart and a second electromechanical event;
    generating a spatio-temporal map of atrial and ventricular mechanics of the heart by tracking an onset of the first and second events for each pixel of a heart wall of the subject identified from the image information, wherein an onset of ventricular contraction is identified by determining a zero-crossing of an incremental strain occurring after an onset of a P-wave;
    identifying, using the spatio-temporal map, a representative mechanical cycle associated with a contraction of the heart; and determining a focal rhythm and a type of cardiac arrhythmia present in the heart using the spatio-temporal map.

2. The method of claim 1, wherein the first electromechanical event corresponds to a beginning of a systole of the heart and the second electromechanical event corresponds to an end of the systole.

3. The method of claim 1, wherein the mapping electromechanical activity characterizes propagation patterns of electromechanical strains during focal and reentrant arrhythmias of the heart.

4. The method of claim 1, further comprising identifying regions in which the mechanical and electrical activities are decoupled by mapping the electromechanical activity of the heart.

5. The method of claim 1, wherein generating the spatio-temporal map further comprises obtaining isochrones correlated to electrical isochrones by tracking a propagation front of an end-diastole electromechanical activation of the heart.

6. The method of claim 1, further comprising determining that the cardiac arrhythmia present in the heart is a type of reentrant arrhythmia, wherein generating the spatio-temporal map further comprises performing a high-resolution Fourier transform using a generalized Goertzel algorithm to interpolate strain signals in Fourier space for each individual pixel in an atrium of the heart.

7. The method of claim 1, further comprising generating a peak mechanical cycle length (MCL) map by selecting a MCL having a highest amplitude within the physiologically-relevant time range for each pixel of the ultrasound scan of the heart, wherein the MCL map identifies, for each pixel of an atrium, which cycle length is greatest in a Fourier spectrum of cycle lengths.

8. The method of claim 7, further comprising:
   determining a cycle length representing an atrial contraction of the heart; and
   determining a phase corresponding to the determined cycle length to map a propagation of a mechanical oscillation of the heart at the determined cycle length.

9. The method of claim 1, further comprising performing the ultrasound scan of the heart, wherein performing the ultrasound scan further comprises:
   emitting a circular ultrasonic wave to instruct an ultrasound apparatus to perform a motion estimation sequence;
   performing a B-mode acquisition to capture heart anatomy of the heart;
   generating a plurality of beams to reconstruct frames from the motion estimation sequence using a delay-and-sum algorithm with a reconstructed sampling frequency.

10. A system for mapping electromechanical activity during an arrhythmia comprising:
    a processor adapted to:
       obtain image information of a heart of a subject using an imaging device;
       generate a strain map of the heart from the image information;
       determine, from the strain map occurrences of a first electromechanical event of the heart and a second electromechanical event;
       generate a spatio-temporal map of atrial and ventricular mechanics of the heart by tracking an onset of the first and second events for each pixel of a heart wall of the subject, wherein an onset of ventricular contraction is identified by determining a zero-crossing of an incremental strain occurring after an onset of a P-wave;
       identify, using the spatio-temporal map, a representative mechanical cycle associated with a contraction of the heart; and
       determine a focal rhythm and a type of cardiac arrhythmia present in the heart using the spatio-temporal map.

11. The method of claim 10, wherein the first electromechanical event corresponds to a beginning of a systole of the heart and the second electromechanical event corresponds to an end of the systole.

12. The system of claim 10, wherein the processor generates the spatio-temporal map by obtaining isochrones correlated to electrical isochrones by tracking a propagation front of an end-diastole electromechanical activation of the heart.

13. The system of claim 10, wherein the processor determines that the cardiac arrhythmia present in the heart is a type of reentrant arrhythmia, and wherein the processor generates the spatio-temporal map by performing a high-resolution Fourier transform using a generalized Goertzel algorithm to interpolate strain signals in Fourier space for each individual pixel in an atrium of the heart.

14. The system of claim 10, wherein the processor is further configured to generate a peak mechanical cycle length (MCL) map by selecting a MCL having a highest amplitude within the physiologically-relevant time range for each pixel of the ultrasound scan of the heart, wherein the MCL map identifies, for each pixel of an atrium, which cycle length is greatest in a Fourier spectrum of cycle lengths.

15. The system of claim 14, wherein the processor is further configured to:
    determine a cycle length representing an atrial contraction of the heart; and
    determine a phase corresponding to the determined cycle length to map a propagation of a mechanical oscillation of the heart at the determined cycle length.

16. The system of claim 10, wherein the processor is further configured to perform the ultrasound scan of the heart, wherein the processor performs the ultrasound scan by:
    emitting a circular ultrasonic wave to instruct an ultrasound apparatus to perform a motion estimation sequence;
    performing a B-mode acquisition to capture heart anatomy of the heart;
    generating a plurality of beams to reconstruct frames from the motion estimation sequence using a delay-and-sum algorithm with a reconstructed sampling frequency.

* * * * *